United States Patent
Chao et al.

(10) Patent No.: US 9,308,011 B2
(45) Date of Patent: Apr. 12, 2016

(54) SURGICAL DEVICE AND METHODS

(75) Inventors: Kevin Zi Jun Chao, Palo Alto, CA (US); John Avi Roop, Menlo Park, CA (US); Greg Magee, Menlo Park, CA (US); Ronald Jou, Cupertino, CA (US); Reuben Brewer, Millbrae, CA (US); Christopher Steven Pell, San Rafael, CA (US); Bryan J. Duggan, Ortonvilled, MI (US); Zhi Chen Dong, Stanford, CA (US); Thomas Ruby, Mountain View, CA (US)

(73) Assignee: THE BOARD OF TRUSTEES OF THE LELAND STANFORD JUNIOR UNIVERSITY, Palo Alto, CA (US)

( * ) Notice: Subject to any disclaimer, the term of this patent is extended or adjusted under 35 U.S.C. 154(b) by 51 days.

(21) Appl. No.: 13/251,265

(22) Filed: Oct. 2, 2011

(65) Prior Publication Data

US 2012/0083826 A1    Apr. 5, 2012

Related U.S. Application Data

(63) Continuation of application No. PCT/US2010/001036, filed on Apr. 5, 2010.

(60) Provisional application No. 61/166,654, filed on Apr. 3, 2009, provisional application No. 61/187,078, filed on Jun. 15, 2009, provisional application No. 61/314,595, filed on Mar. 17, 2010.

(51) Int. Cl.
*A61B 17/00* (2006.01)
*A61B 17/29* (2006.01)
(Continued)

(52) U.S. Cl.
CPC ........... *A61B 17/29* (2013.01); *A61B 17/00234* (2013.01); *A61B 17/0218* (2013.01);
(Continued)

(58) Field of Classification Search
CPC .............. A61B 17/00234; A61B 17/0218; A61B 17/29; A61B 18/1482; A61B 2017/00464; A61B 2017/00477; A61B 2017/2931; A61B 2017/294; A61B 2017/2391; A61B 2017/2941; A61B 2017/2901; A61B 2017/2908; A61B 2019/4868; A61B 2017/00473; A61B 2017/00486; A61B 2017/2926; A61B 2017/2929; A61B 2017/2932; A61B 2017/2933; A61B 2017/2934; A61B 2017/2936; A61B 2017/2937; A61B 2017/2938; A61B 19/026; A61B 19/0256; A61B 2019/0263; A61B 2019/027; A61B 2019/0283; A61B 2019/4831

See application file for complete search history.

(56) References Cited

U.S. PATENT DOCUMENTS

| 4,572,038 A | 2/1986 | Graham |
| 5,308,358 A | 5/1994 | Bond et al. |

(Continued)

FOREIGN PATENT DOCUMENTS

WO    2011089565 A1    7/2011

OTHER PUBLICATIONS

International Search Report for corresponding International Application No. PCT/US2010/001036, Applicant: The Board of Trustees of the Leland Stanford Junior University, Form PCT/ISA/210: dated Jun. 4, 2010, 2 pages.

(Continued)

*Primary Examiner* — Jonathan W Miles
*Assistant Examiner* — Kendra Obu
(74) *Attorney, Agent, or Firm* — William A. English; Vista IP Law Group LLP

(57) ABSTRACT

A system and method for abdominal surgery is disclosed. The system can have one or more end effectors that can be attached to an introducer and/or tray and inserted into the abdomen through a large puncture through the patient's umbilicus. The end effector can have a surgical tool, such as a grasper. The system can have a manipulatable control arm that can be inserted into the abdomen through a small puncture through the patient's body wall. The end effector can be attached to the control arm and simultaneously or concurrently detached from the introducer or tray. The control arm can then manipulate the end effector to perform the surgery.

30 Claims, 40 Drawing Sheets

(51) Int. Cl.
*A61B 17/02* (2006.01)
*A61B 17/122* (2006.01)
*A61B 17/128* (2006.01)
*A61B 18/14* (2006.01)

(52) U.S. Cl.
CPC ........... *A61B17/122* (2013.01); *A61B 17/1285* (2013.01); *A61B 18/1482* (2013.01); *A61B 2017/00464* (2013.01); *A61B 2017/00477* (2013.01); *A61B 2017/294* (2013.01); *A61B 2017/2931* (2013.01); *A61B 2018/1422* (2013.01)

(56) References Cited

U.S. PATENT DOCUMENTS

| | | | |
|---|---|---|---|
| 5,336,238 A | 8/1994 | Holmes et al. | |
| 5,352,219 A | 10/1994 | Reddy | |
| 5,368,606 A | 11/1994 | Marlow et al. | |
| 5,441,059 A | 8/1995 | Dannan | |
| 5,593,402 A | 1/1997 | Patrick | |
| 5,618,303 A | 4/1997 | Marlow et al. | |
| 5,782,748 A | 7/1998 | Palmer et al. | |
| 5,792,165 A | 8/1998 | Klieman et al. | |
| 5,893,875 A | 4/1999 | O'Connor et al. | |
| 6,074,408 A | 6/2000 | Freeman | |
| 6,309,397 B1 | 10/2001 | Julian et al. | |
| 6,558,318 B1 | 5/2003 | Daniel et al. | |
| 6,607,475 B2 | 8/2003 | Doyle et al. | |
| 6,723,043 B2 | 4/2004 | Kleeman et al. | |
| 6,916,314 B2 | 7/2005 | Schneider et al. | |
| 7,122,028 B2 | 10/2006 | Looper et al. | |
| 7,241,290 B2 | 7/2007 | Doyle et al. | |
| 7,429,259 B2 | 9/2008 | Cadeddu et al. | |
| 7,699,835 B2 | 4/2010 | Lee et al. | |
| 7,862,553 B2 | 1/2011 | Ewaschuk | |
| 2003/0060687 A1 | 3/2003 | Kleeman et al. | |
| 2003/0130693 A1 | 7/2003 | Levin et al. | |
| 2005/0165449 A1 | 7/2005 | Cadeddu et al. | |
| 2008/0015552 A1 | 1/2008 | Doyle et al. | |
| 2008/0243106 A1 | 10/2008 | Coe et al. | |
| 2008/0287926 A1 | 11/2008 | Abou El Kheir | |
| 2010/0249700 A1 | 9/2010 | Spivey | |
| 2010/0298774 A1 | 11/2010 | Igov | |
| 2011/0087265 A1 | 4/2011 | Nobis et al. | |
| 2011/0087266 A1 | 4/2011 | Conlon et al. | |
| 2011/0208007 A1* | 8/2011 | Shohat ............... | A61B 17/3403 600/227 |

OTHER PUBLICATIONS

PCT International Preliminary Report on Patentability for PCT/US2010/001036, Applicant: The Board of Trustees of the Leland Stanford Junior University, Forms PCT/IB/373 and PCT/ISA/237; dated Oct. 4, 2011, 9 pages.

Office Action for corresponding Singapore National Patent Application No. 201107119-8 including Search Report and Written Opinion, Applicant: The Board of Trustees of the Leland Stanford Junior University; dated Oct. 18, 2012, 15 pages.

* cited by examiner

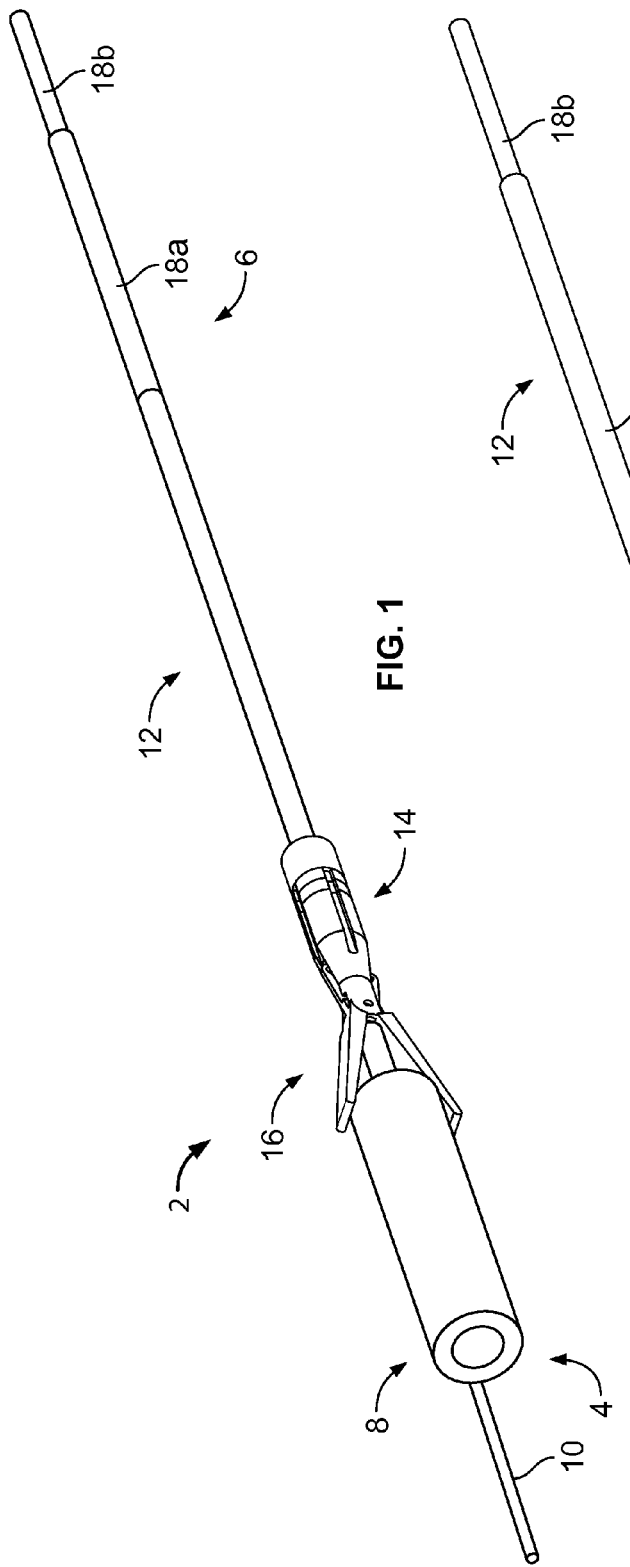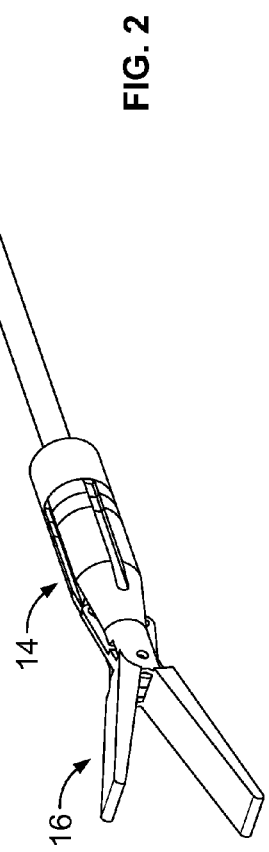

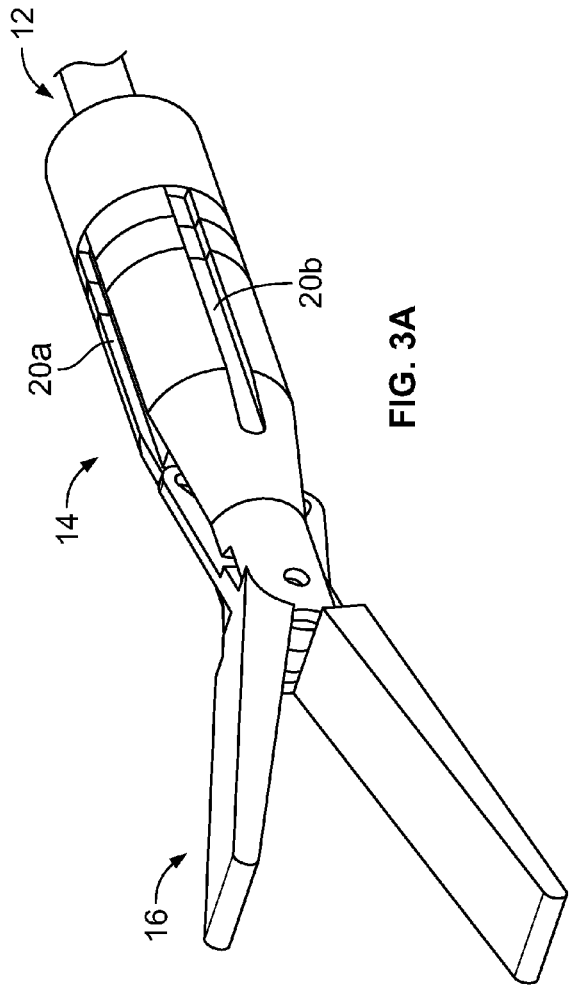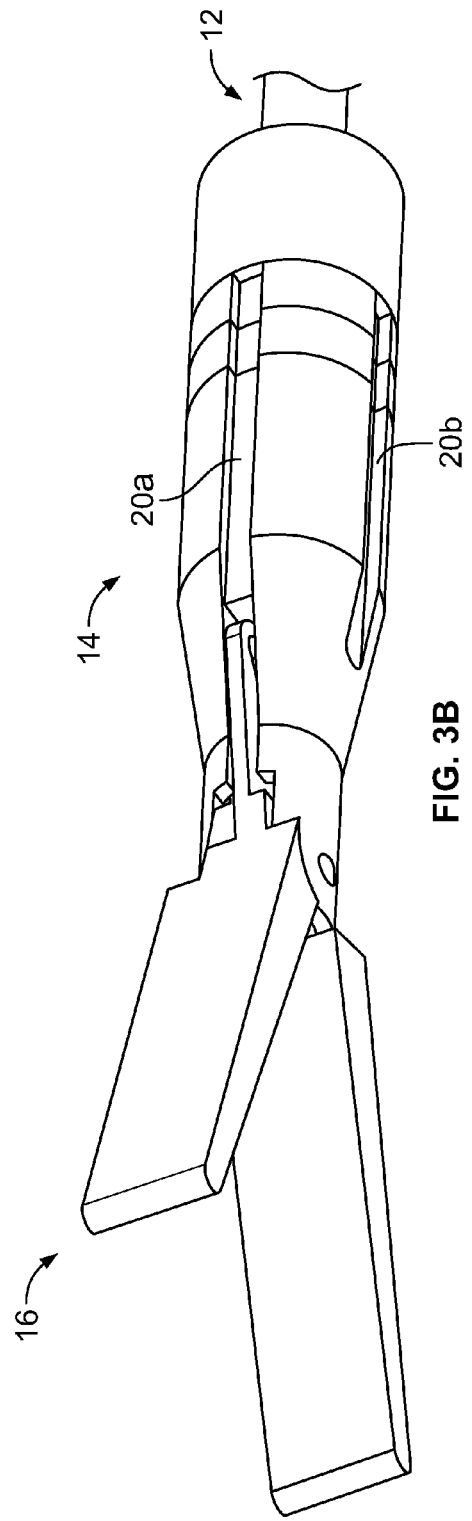

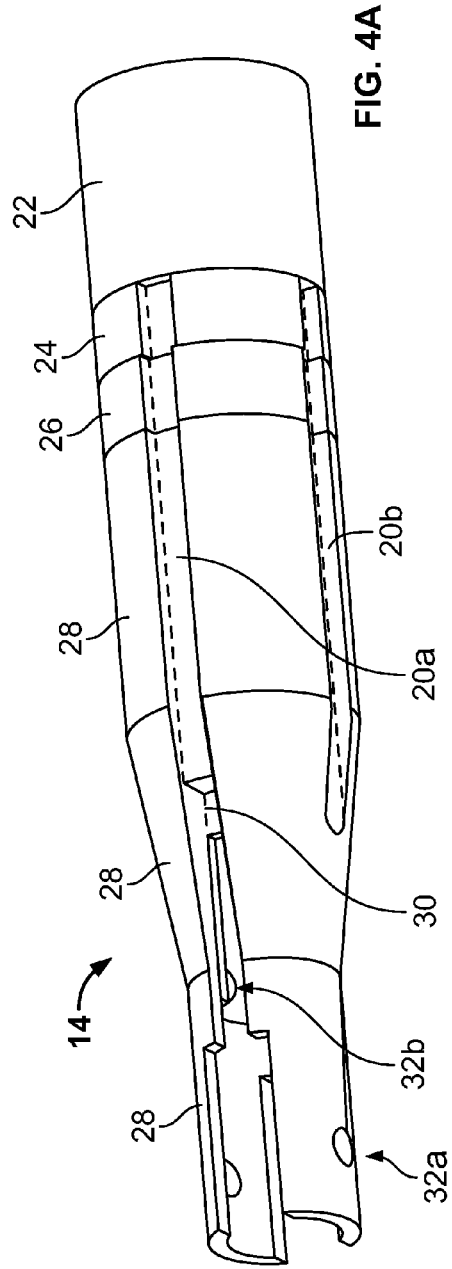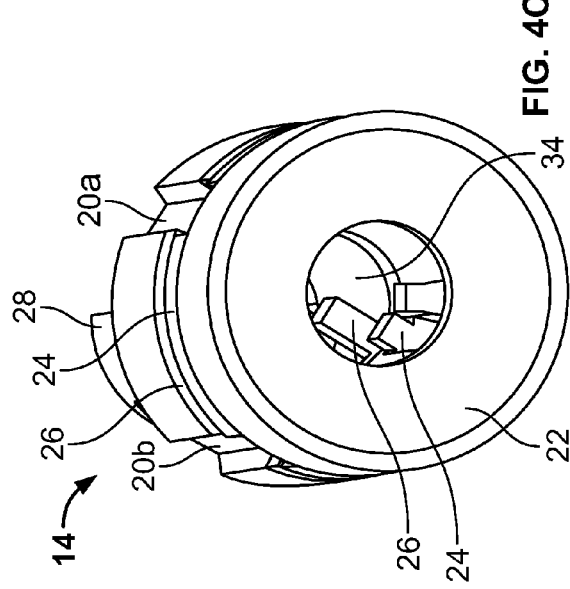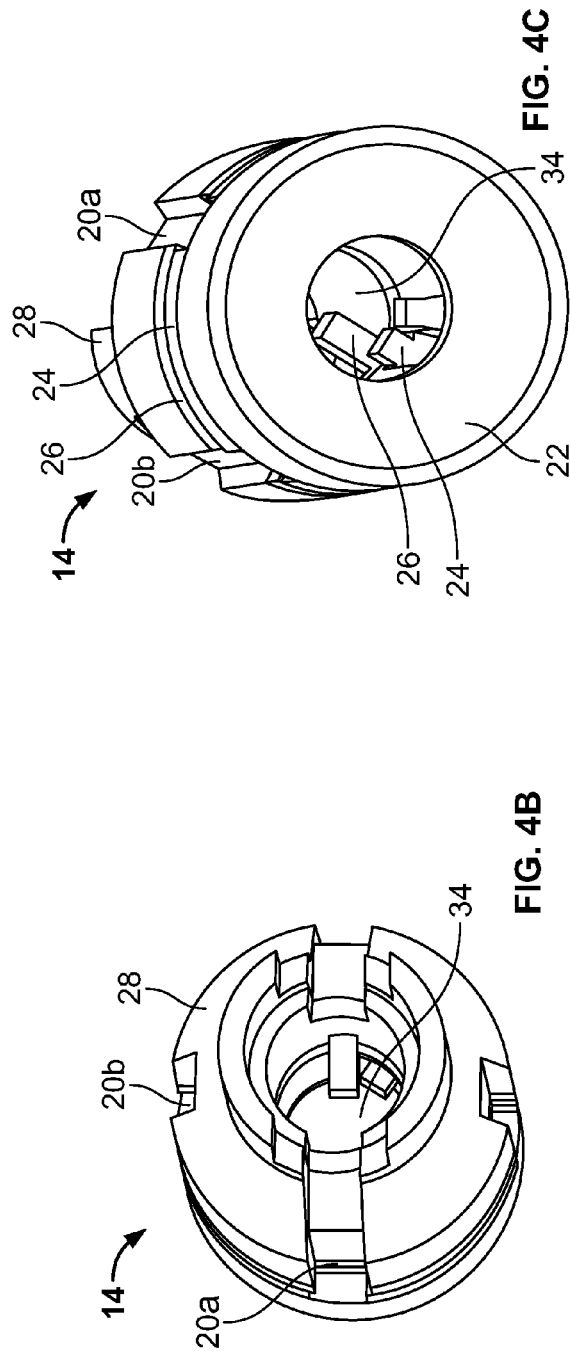

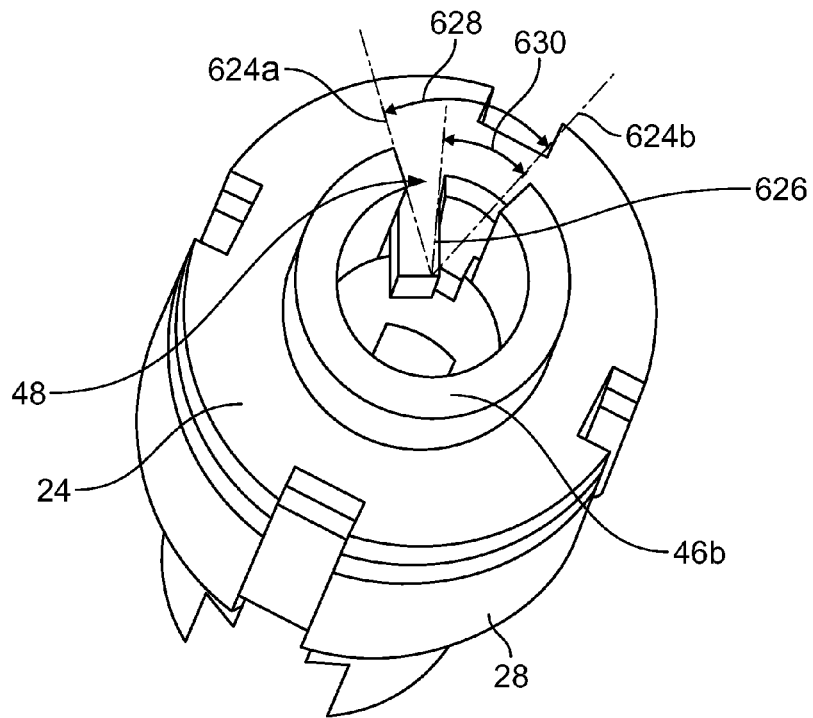
FIG. 4D
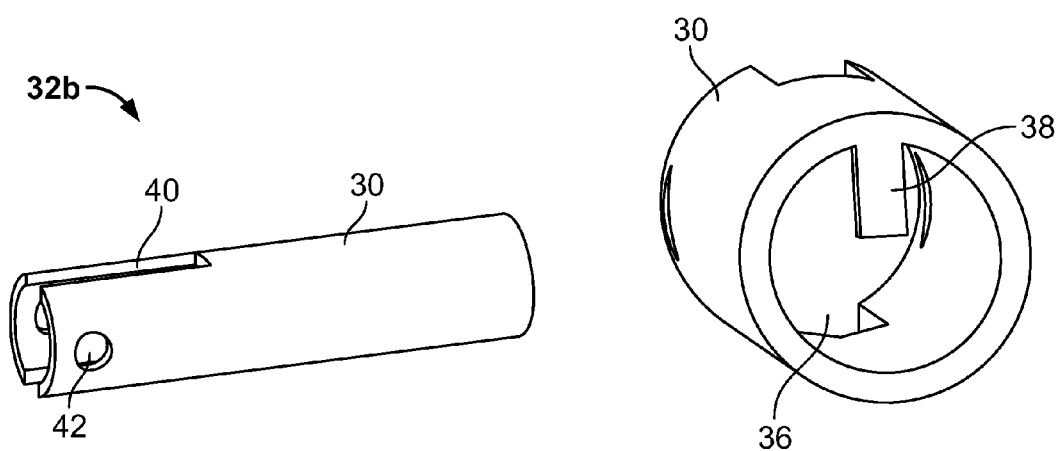
FIG. 5
FIG. 6

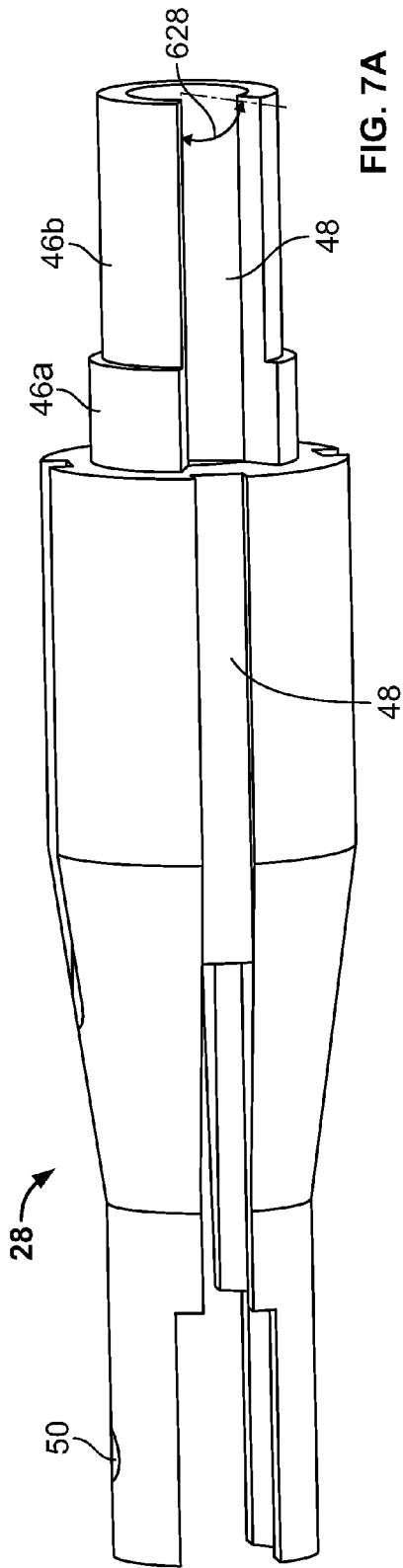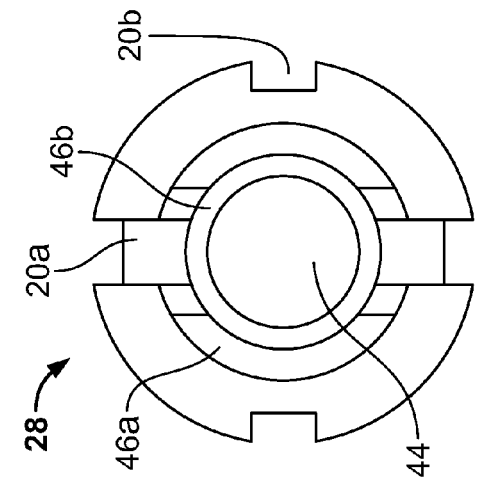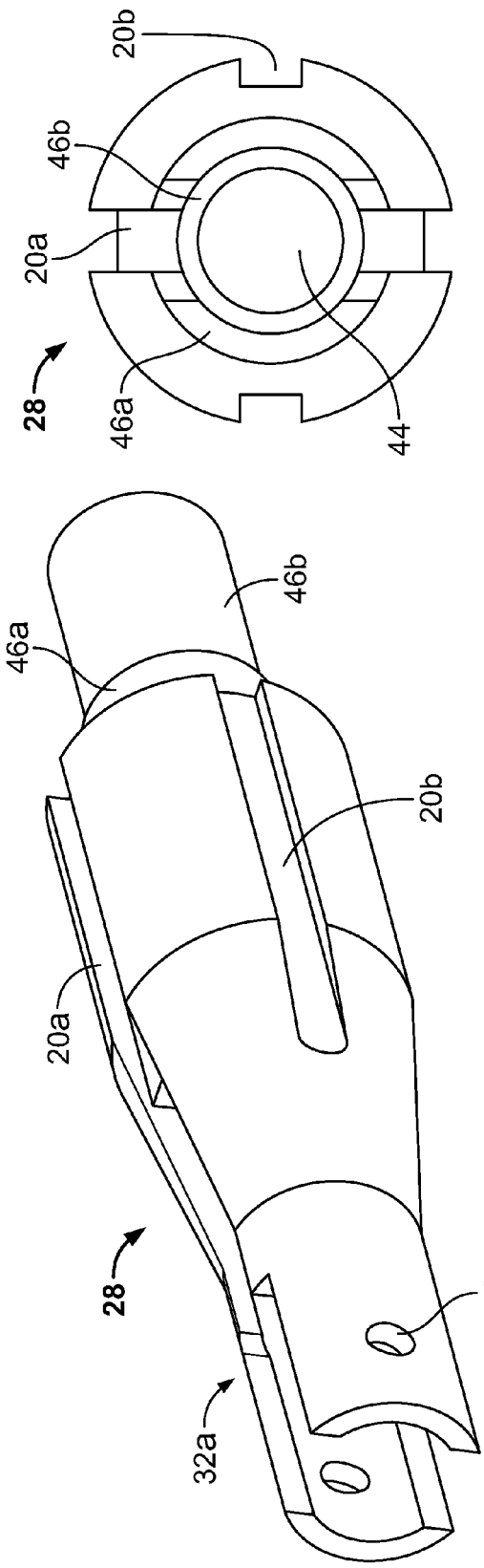

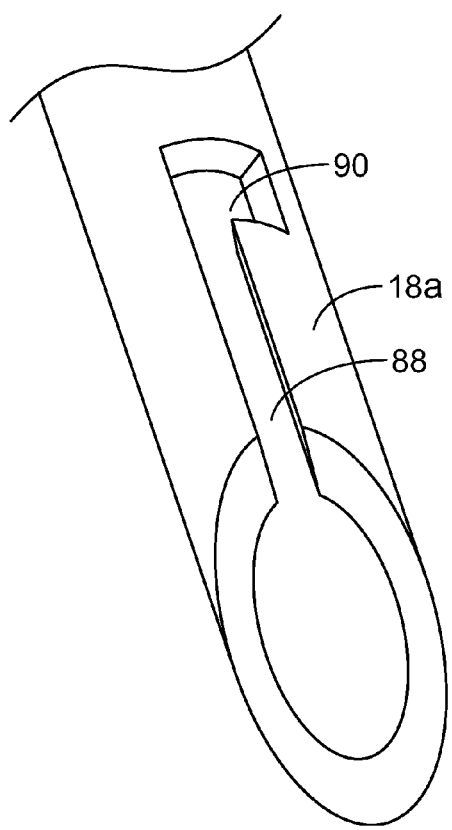
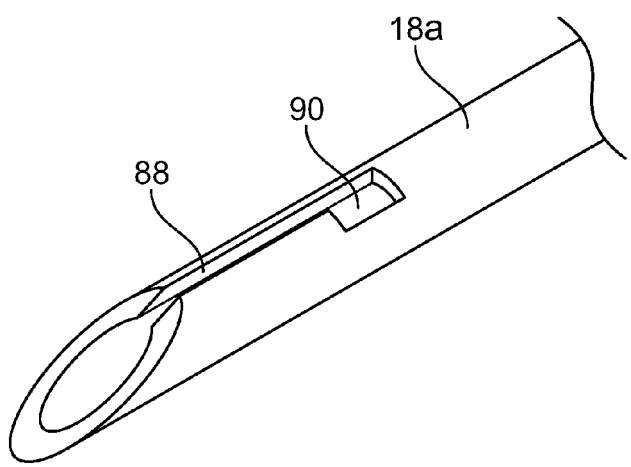
FIG. 12A    FIG. 12B
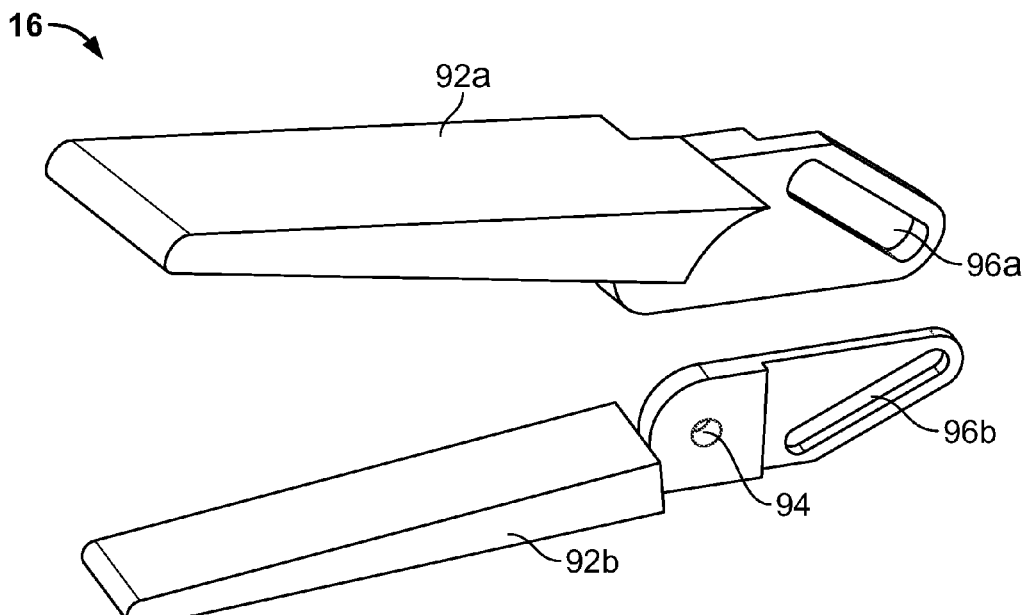
FIG. 13

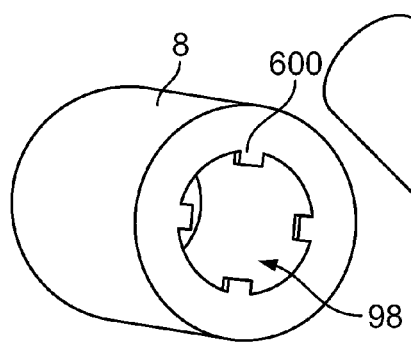
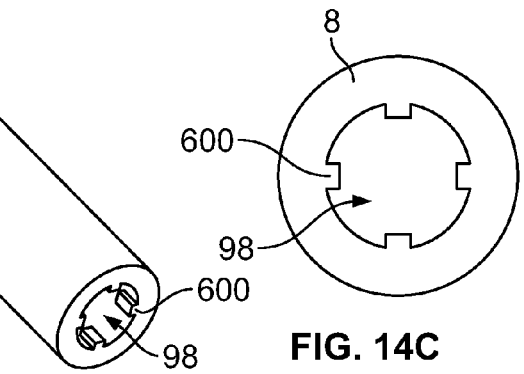
FIG. 14A  FIG. 14B  FIG. 14C
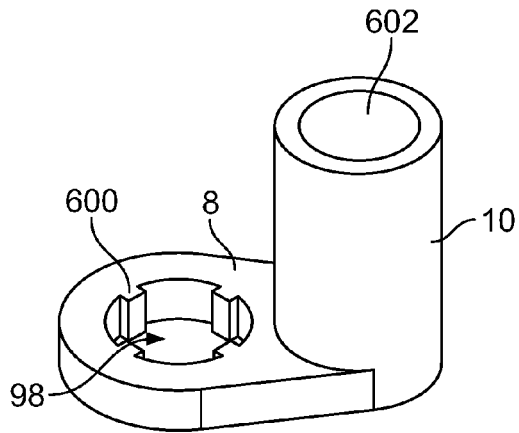
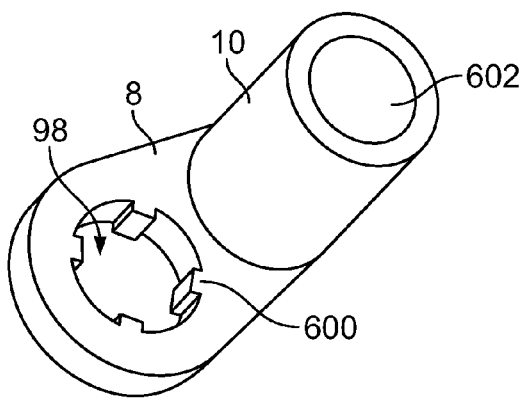
FIG. 15A  FIG. 15B
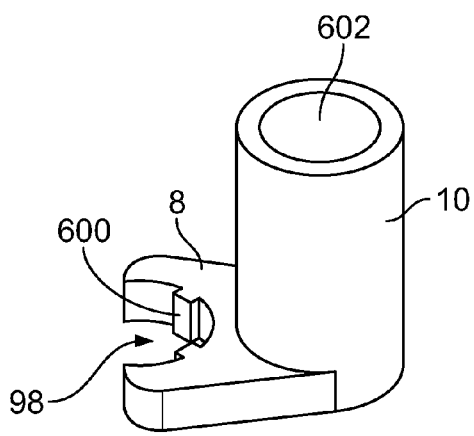
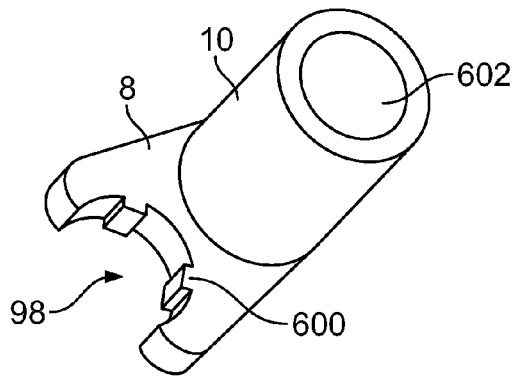
FIG. 16A  FIG. 16B

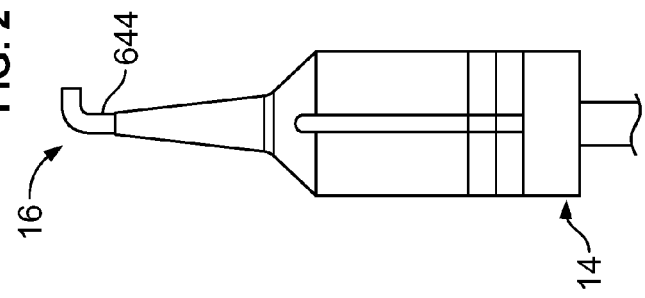
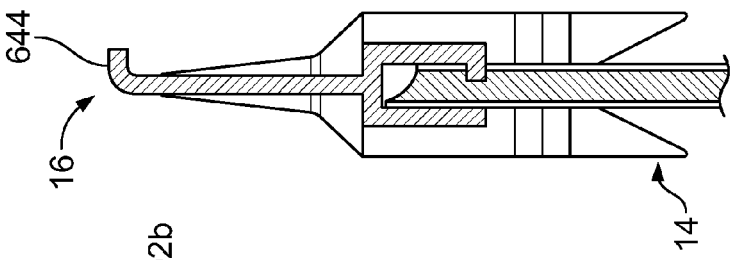
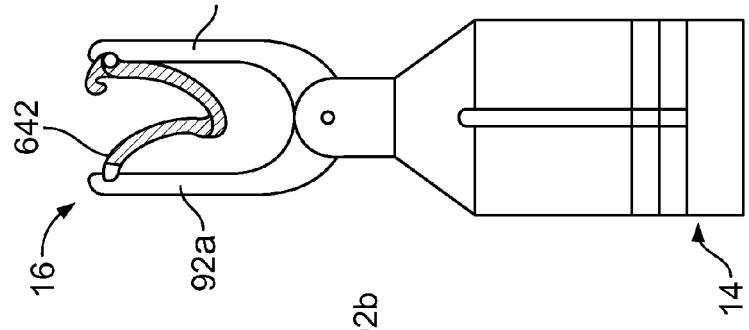
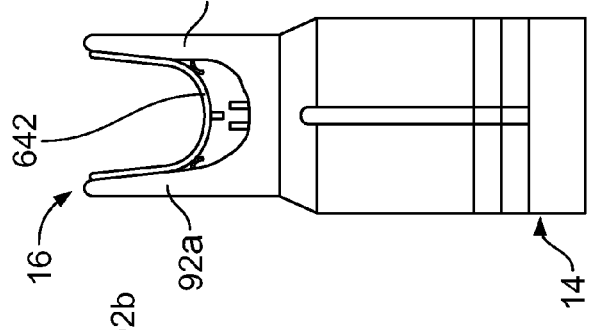
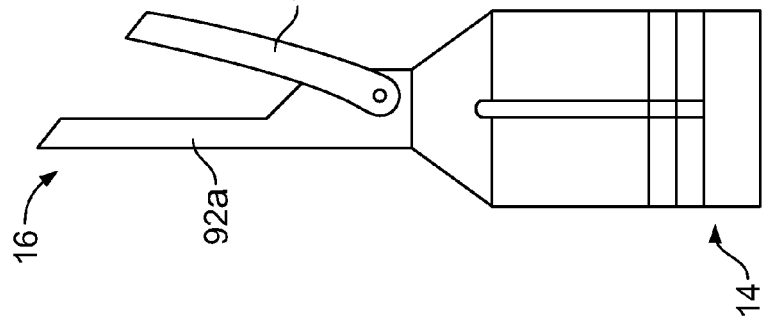

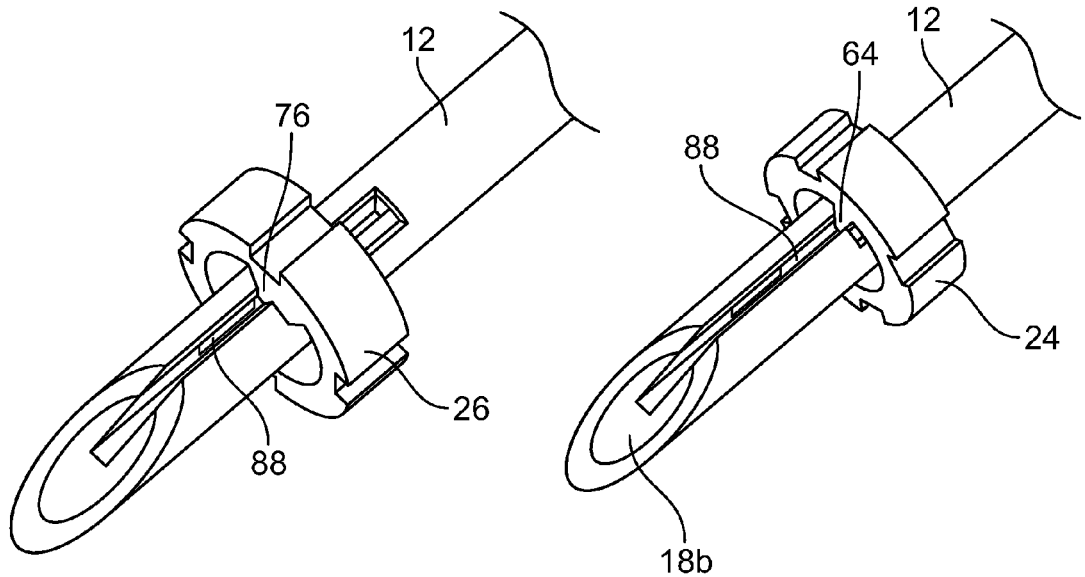
FIG. 25C
FIG. 25D
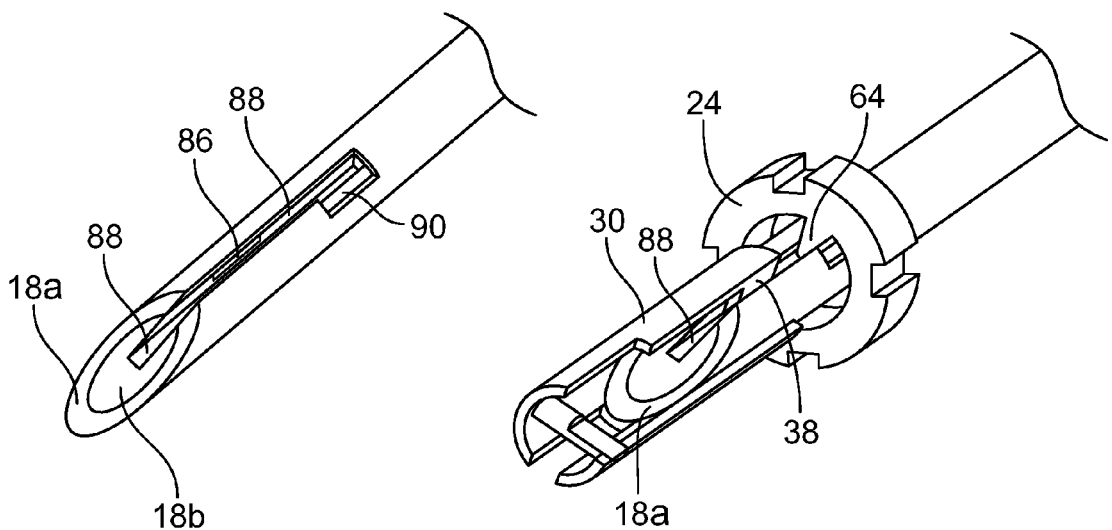
FIG. 25E
FIG. 25F

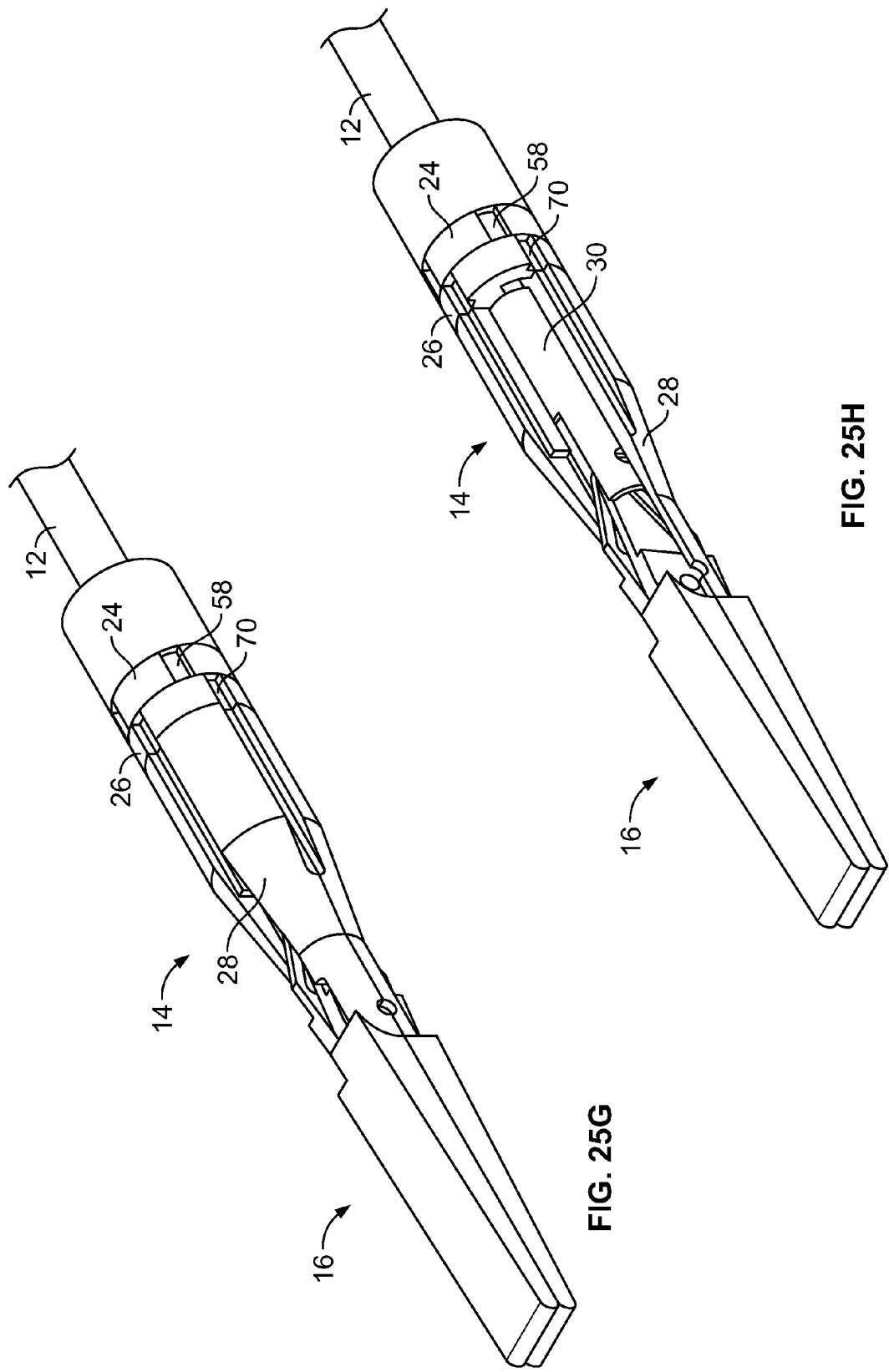

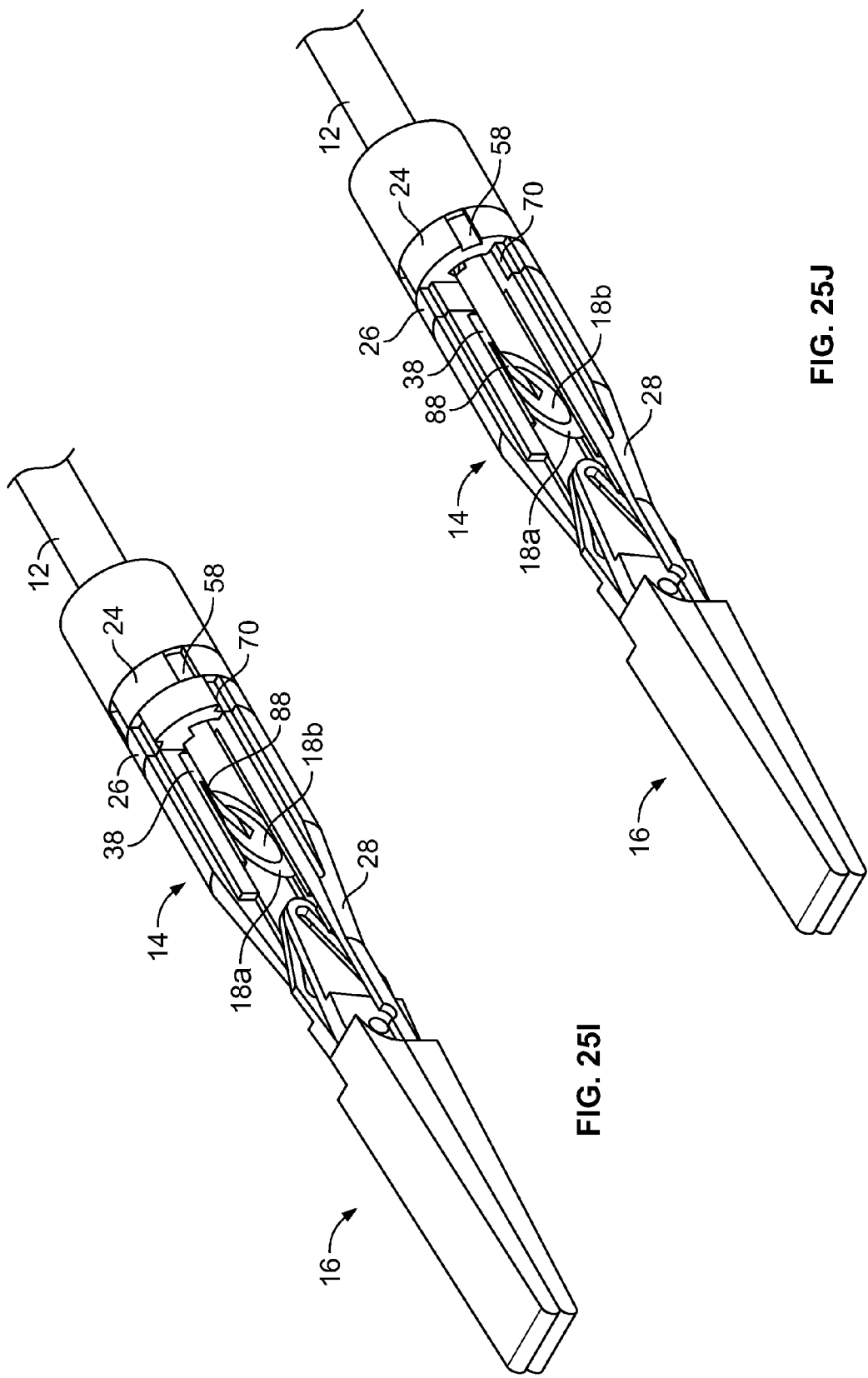

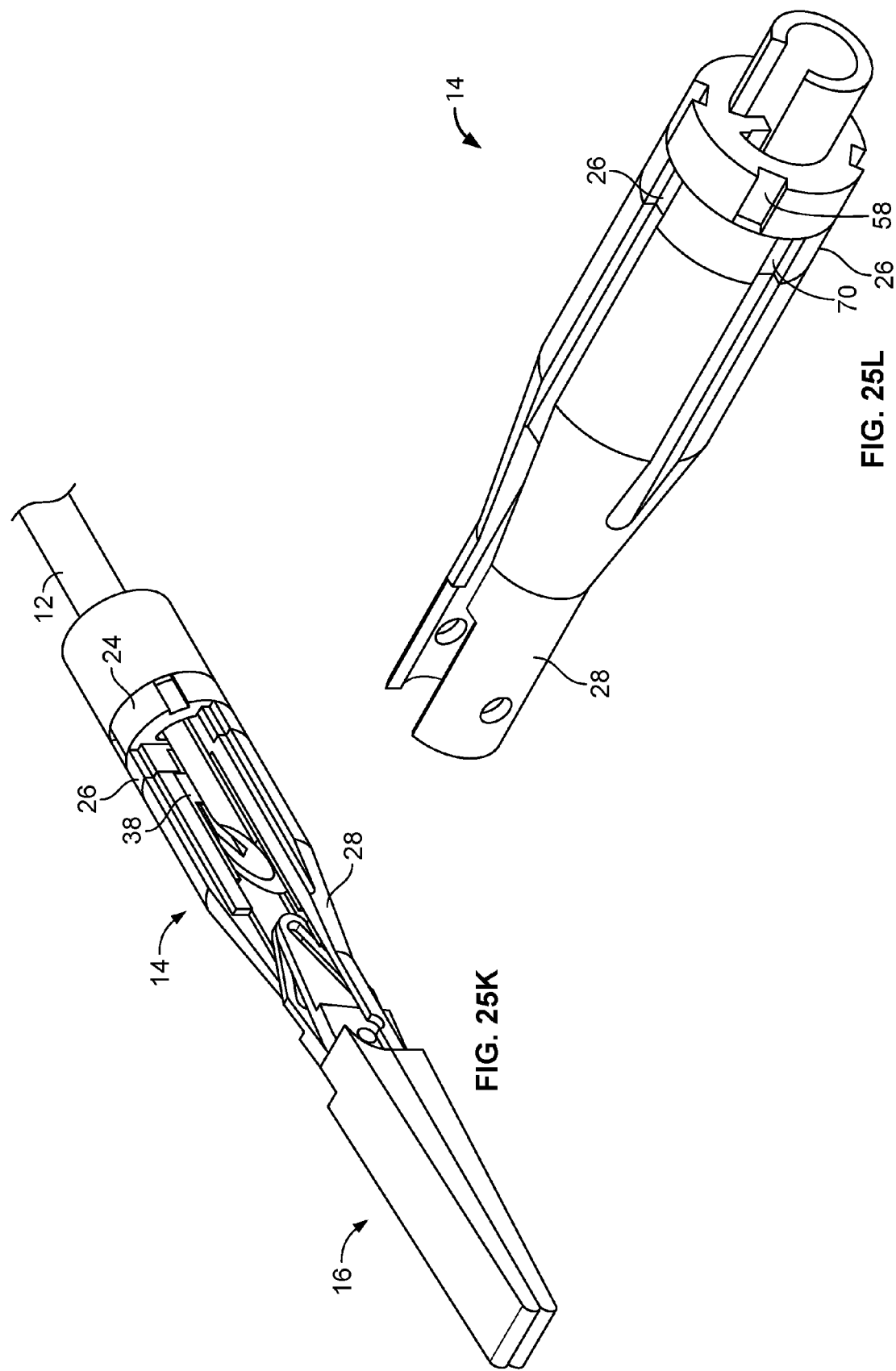

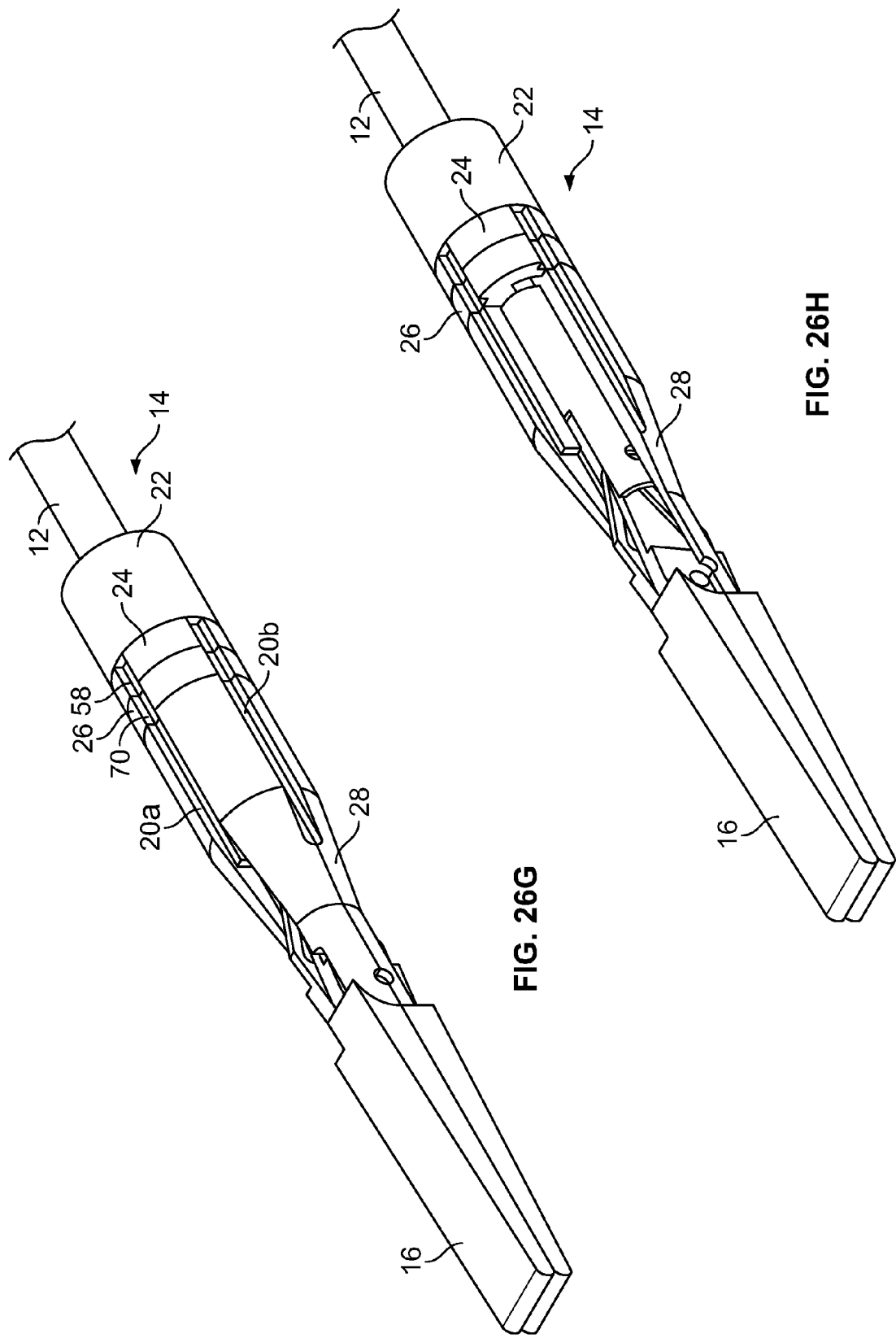

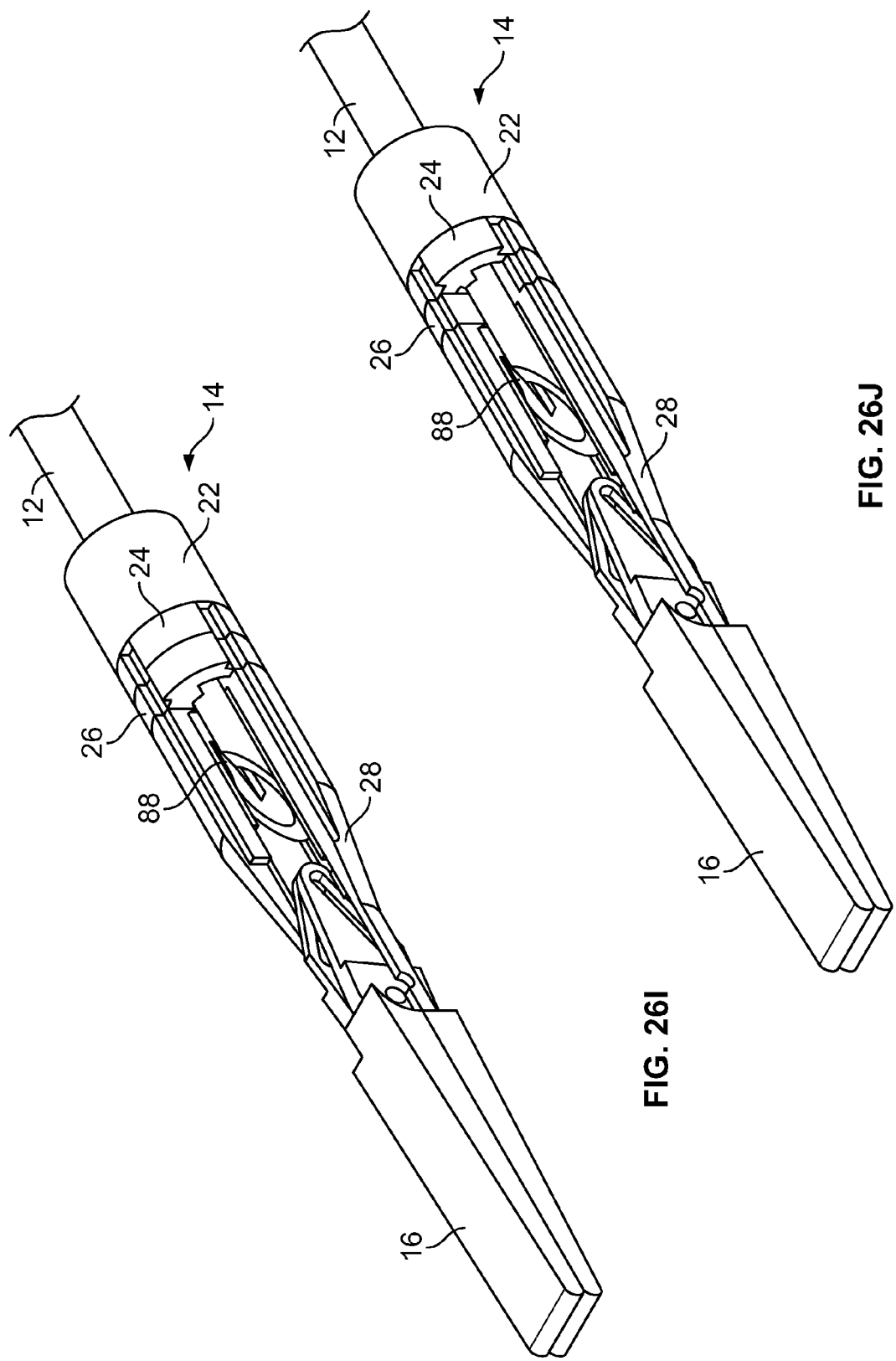

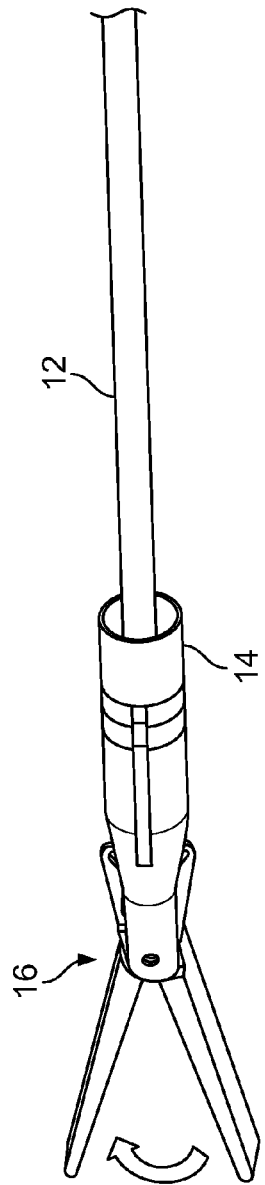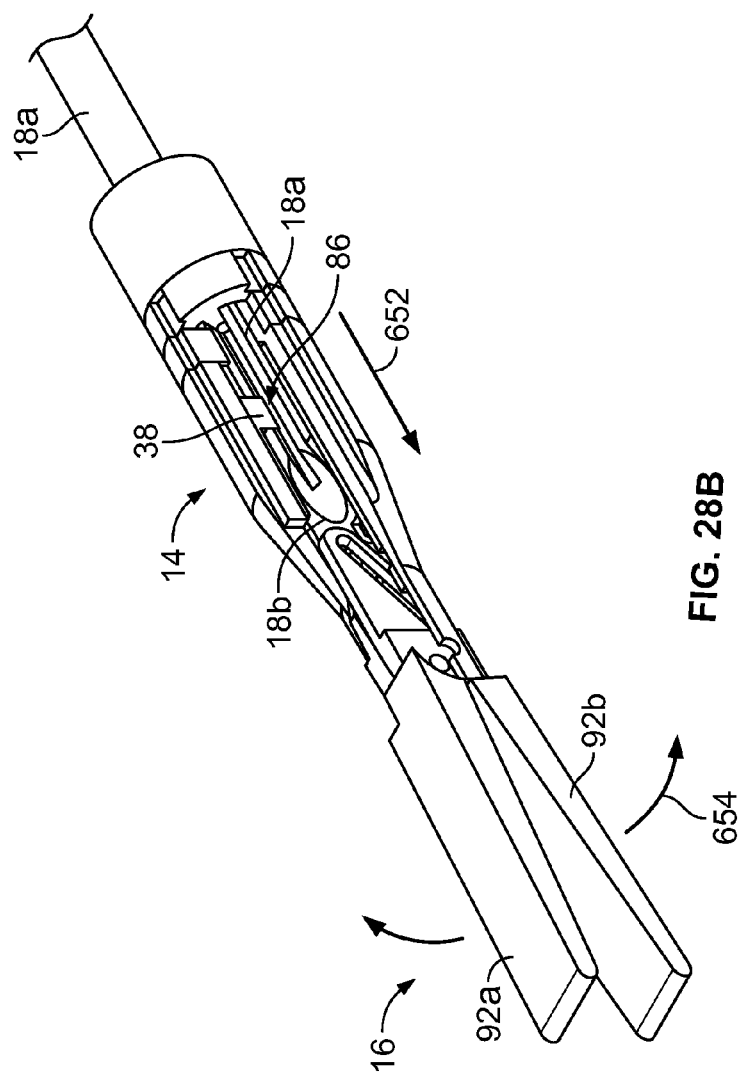
FIG. 28A
FIG. 28B

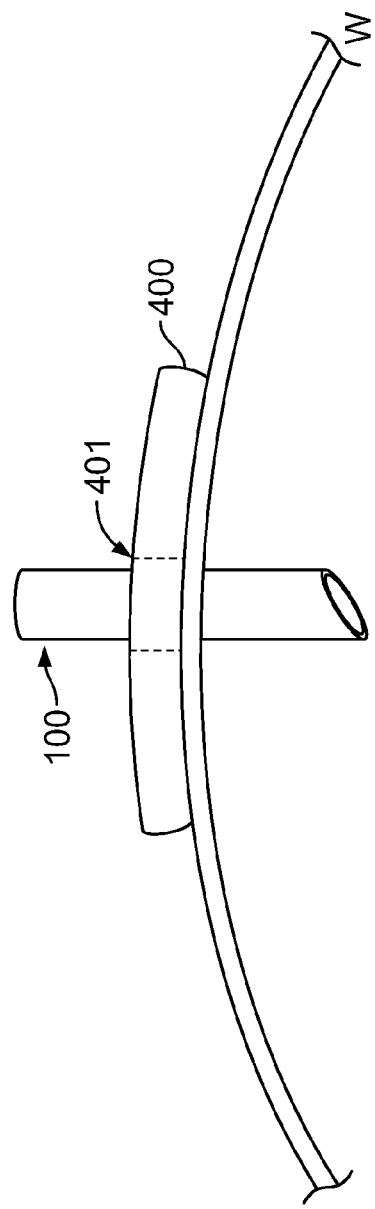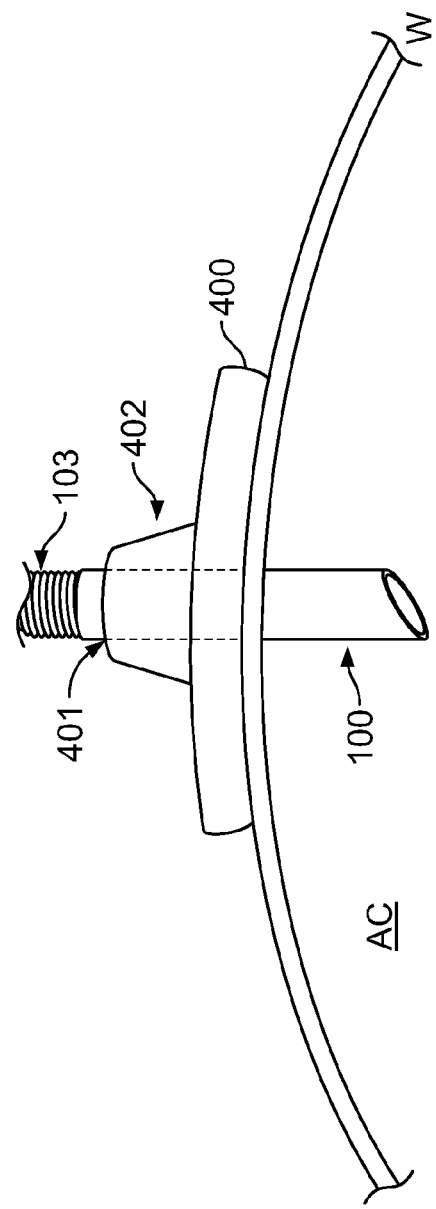

SURGICAL DEVICE AND METHODS

CROSS-REFERENCE TO RELATED APPLICATIONS

This application is a continuation of co-pending International Application No. PCT/US2010/001036, filed Apr. 5, 2010, which claims the benefit of U.S. Provisional Application Nos. 61/166,654 filed 3 Apr. 2009; 61/173,147, filed 27 Apr. 2009; 61/187,078, filed 15 Jun. 2009; and 61/314,595, filed 17 Mar. 2010, all of which are herein incorporated by reference in their entireties.

BACKGROUND

Surgery has become increasingly less invasive thanks to advances in medical technology. Laparoscopy is the dominant minimally invasive surgical (MIS) approach used today and has replaced many traditional "open" approaches. In laparoscopic surgery, trocars (typically 3-5) are placed at separate points in the surgical field. These trocars serve as ports into a body cavity (such as the abdomen) through which special long and thin instruments can be inserted. Manipulation of these tools from outside the body mechanically translates into motion within the body cavity. Depending on the tool head design, different instruments have different functions. The right instrument is selected based on what the surgeon needs for that step of the procedure.

Minimally Invasive Surgery (MIS) offers the advantages of minimal trauma to the abdominal wall and hence less post-operative pain, fewer wound complications, earlier patient mobilization and shorter length of stay. Laparoscopic access to the peritoneal space is the dominant MIS approach when performing minimally invasive abdominal operations.

Recent clinical studies show that further reduction of the size and number of incisions offers a wealth of added benefits such as faster recovery, less pain, reduced operative time, and improved cosmetic result. Such benefits have physical and psychological impact.

A recent wave of scar-free techniques, including natural orifice transluminal endoscopic surgery ("NOTES") and single-port surgery, have emerged to meet the need to further reduce the incisions required for surgical procedures. Ample information explaining the details of these new approaches exists in the public domain. Of the two, single-port surgery is thought among the surgery community to be the more feasible approach given available technology today.

Single-port surgery involves a multi-channel port that is typically placed in the belly button. This results in hidden scar post operatively. Through these channels, standard laparoscopic tools can be inserted. However, manipulation is more challenging because the tight aperture of the belly button and strong connective tissue in the abdominal wall forces all the instruments to move dependent on one another. The surgeon's hands are crowded together because of these constraints. Triangulation is largely lost. This makes the procedure frustrating to perform compared to the standard approach.

A number of commercially available tools have been designed to circumvent some of these limitations. Some are variations of standard laparoscopic instruments but have articulating tool heads. Such design is aimed for re-enabling triangulation. However, constraints of the belly button port forces these articulating tools to cross, thus reversing the left-right motion between what the surgeon does with his hands and what he sees on the video monitor. Also, the complex mechanics behind the articulation drives the cost up significantly.

The need exists for a revised laparoscopic technique and tools that reduce surgery-induced trauma but preserves the ergonomics and visualization that surgeons have become accustomed to. This makes such an approach safer for patients. A scar free result may appeal more to young adults, but the potential health benefits of a less traumatic approach is much higher for children and the elderly.

The first step during a laparoscopic surgical procedure is to insufflate the body cavity with a harmless gas (such as carbon dioxide) to increase the working space for these tools. The trocars are inserted across the abdominal wall and are designed to prevent excessive leak of the insufflation gas, which invariably happens with incisions greater than three millimeters (3 mm).

In endoscopic and laparoscopic surgical procedures, a trocar device is used to puncture the patient's body in order to provide an access port through the abdominal wall to allow for the introduction of surgical instruments. A typical trocar requires a one-centimeter incision. Typically, a first trocar is placed above the umbilicus to introduce a camera to allow the surgeons to view the surgical site. The camera view is projected on a screen outside the body, which the surgeon and his or her assistants watch in order to appropriately manipulate the instruments inside the body cavity. Additional trocars are used to introduce surgical instruments, such as grasping tools, scissors, clips and electrosurgical instruments. Typically, the laparoscopic instruments extend toward the surgical target from either side of the video camera. This "triangulation" of the instruments provides the most ergonomic and intuitive set up for the surgeon.

Patients who undergo laparoscopic surgery benefit from shorter hospital stays and reduced surgery-inflicted morbidity compared to those who undergo open surgery. But, the number of trocar ports used in an operation is trauma-limited. For many cases, surgeries requiring more than five to seven (5-7) ports may be better performed using an open approach. Surgeons often hesitate to place more ports, even if it would mean making the procedure easier to do, because of the increased risk of wound complications with each additional incision (such as infection, dehiscence, or hernia).

SUMMARY OF THE INVENTION

The present invention relates to laparoscopic surgical tools designed to not leave a visible scar. These laparoscopic surgical tools are comprised of a handle, a trans abdominal drive system and a tool head/tip. The trans abdominal drive system is intended to transmit motion, energy, and data across a patient's body cavity wall without leaving a permanent scar. The trans abdominal drive system can be applied to laparoscopic surgical procedures including but not limited to appendix removal, gall bladder removal, hernia repair and uterus removal. Current laparoscopic tools require a port or trocar to be placed across the patients body cavity wall. Said ports or trocars are large and leave a scar. The trans abdominal drive portion of the laparoscopic tool allows the surgeon to use laparoscopic tools across a body cavity wall without leaving a scar.

A modular surgical instrument that enables standard laparoscopic techniques through small puncture holes in the body wall and methods of using the same are disclosed. The assembled modular instrument has a handle, a small diameter needle-like cannular shaft (e.g., less than or equal to about 2.5 mm diameter), and a tool head. The tool head is initially inserted through a trocar port at a separate location (such as the umbilicus). This step relies on a secondary introducer device. The cannular shaft unit is actually two coaxial shafts that move relative to one another. It is pierced through the body wall into the body cavity. The cannular shaft attaches to the tool head inside the body. The handle is attached to the external part of the cannular shaft. This step can be done before or after insertion of the cannular shaft into the body cavity. Once the modular instrument is fully assembled, the tool head is manipulatable through the puncture hole at any desired site. There is a coaxial locking mechanism between the cannular shaft and the tool head that locks both the external shaft and the internal "active" shaft. The locking mechanism utilizes a series of channels and keyways so that the tool tip is fully constrained to the cannular shaft with redundant locking for tool head retention. The tool head can only be unlocked from the cannular shaft using a complementary/corresponding component attached to an introducer or remover device tool. The tool head may have a variety of forms and functions, selected by the operator specifically for the task relevant to the procedure. The mechanisms used to drive the tool head may be simple mechanical (e.g., through coaxial movement), powered (e.g., torquing power drill), energized (e.g., electrocautery), pneumatized (e.g., vacuum suction), or combinations thereof.

Another embodiment of the trans abdominal drive system is made up of a needle, a drive trocar, an external plate, an internal plate, an external supporting member, an internal supporting member, an attachment mechanism between the plates, an attachment mechanism between the internal supporting member and the internal plate, an attachment mechanism between the external supporting member and the external plate, a suspension system between the external supporting mechanism and the outer housing, a suspension system between the internal supporting mechanism and the internal plate or a suspension system between the internal supporting mechanism and the end-effecter of the surgical tool, and an outer housing. The trans abdominal drive system could be magnetically coupled to eliminate the need to cross the skin layer. The trans abdominal drive system could be hydraulically coupled to ensure only one violation of the skin at the umbilicus.

The trans abdominal drive system can transmit motion, energy, and data across a patient's body cavity wall without leaving a permanent scar. The trans abdominal drive system can be applied to laparoscopic surgical procedures including but not limited to appendix removal, gall bladder removal, hernia repair and uterus removal. The trans abdominal drive system allows the surgeon to use laparoscopic tools across a body cavity wall without leaving a scar.

The trans abdominal drive system can have a 14-gauge needle based drive system designed to mate to a handle on one end and mate to an end effecter on the other end. The trans abdominal drive system can have a needle, a drive trocar, an external plate, an internal plate, an external supporting member, an internal supporting member, an attachment mechanism between the plates, an attachment mechanism between the internal supporting member and the internal plate, an attachment mechanism between the external supporting member and the external plate, a suspension system between the external supporting mechanism and the outer housing, a suspension system between the internal supporting mechanism and the internal plate or a suspension system between the internal supporting mechanism and the end-effecter of the surgical tool, and an outer housing. The trans abdominal drive system could be magnetically coupled to eliminate the need to cross the skin layer. The trans abdominal drive system could be hydraulically coupled, for example, to ensure only one violation of the skin at the umbilicus.

The present disclosure relates to methods and equipment necessary to perform an elective surgical procedure to remove the gall bladder (Laparoscopic Cholecystectomy) with no visible scarring to the patient. The present invention achieves a no-scar result by using detachable instruments that result in only a needle point puncture through the abdomen.

BRIEF DESCRIPTION OF THE DRAWINGS

FIG. 1 illustrates a variation of the surgical device including a secondary introduction tool.

FIG. 2 illustrates the variation of the working portion of the device of FIG. 1.

FIGS. 3a and 3b are side perspective and top perspective views, respectively, of a variation of the working tool and end effector.

FIGS. 4a through 4c are side perspective, distal end perspective, and proximal end perspective views, respectively, of the locking ring assembly of the end effector.

FIG. 4d is a proximal end perspective view of the locking ring assembly of the end effector without the housing cap for illustrative purposes.

FIGS. 5 and 6 are side perspective and end perspective views, respectively, or a variation of the active shaft.

FIGS. 7a through 7c are side, side perspective and proximal end views, respectively, of a variation of the end effector.

FIGS. 12a and 12b are close-up end perspective and side perspective views, respectively, of a variation of the distal end of the outer sub-shaft.

FIG. 13 is an exploded view of a variation of the tool.

FIGS. 14a through 14c are front perspective, side perspective and end views, respectively, of a variation of the introducer.

FIGS. 15a and 15b are side perspective and top perspective views, respectively, of a variation of the introducer.

FIGS. 16a and 16b are side perspective and top perspective views, respectively, of a variation of the introducer.

FIGS. 21a through 21e illustrate variations of the end effectors and tools.

FIG. 28a demonstrates an assembled tool.

FIG. 28b demonstrates how manipulating the internal sub shaft manipulates grasping devices.

FIGS. 30 through 32 illustrate variations of methods of using the device as a means to suspend tissue inside a body cavity.

DETAILED DESCRIPTION

Figure 8A:
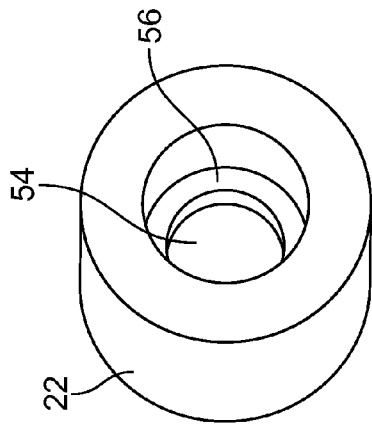
FIGS. 8a and 8b are perspective proximal and distal end views, respectively, of a variation of the housing cap.

FIGS. 1 and 2 illustrate that a surgical device 2 can have a delivery portion 4 and a working portion 6. The delivery portion 4 can have an introducer 8 rigidly or rotatably attached to an introducer rod 10 or delivery system 648. The working portion 6 can have a control element such as a control rod or shaft 12. The distal end of the control shaft 12 can be releasably attached to an end effector 14 attached to a working tool 16, such as a grasper.

During use, the introducer 8 can be releasably attached or connected to the end effector 14 outside of a target site, for example an inflated abdominal or peritoneal cavity. The introducer 8 can deliver the end effector 14 through a large access site, such as through a trocar or cannula through the umbilicus, to the distal end of the control shaft 12 in the target site, such as within the abdominal wall. The working tool 16 can be attached to the end effector 14. The introducer 8 and/or control shaft 12 can then be manipulated, for example by longitudinally translating and turning one or both the introducer 8 and/or control shaft 12, which can result in the separation or detachment of the end effector 12 from the introducer 8 and concurrent attachment or connecting of the end effector to the control shaft 12. The control shaft 12 can then manipulate the working tool 16 to perform a surgical task at or near the target site. The control shaft 12 can then re-engage and attach the end effector 14 to the introducer 8, releasing or detaching the end effector 14 from the control shaft 12. The introducer rod 10 can then remove the introducer 8, end effector 14 and working tool 16 through the large access site. The control shaft 12 can be introduced and removed from the target site through a smaller access site.

The introducer rod 10 can be a rigid or flexible elongated member that can be fixedly or articulably attached or integral with the lateral side or proximal end of the introducer 8. One or more introducers 8 can be attached to a single introducer rod 10. The one or more introducers 8 can be controllably or passively articulated with respect to the introducer rod 10.

The control shaft 12 can be an elongated member. The distal end of the control shaft 12 can controllably attach to and detach from the end effector 14. The control shaft 12 can be hollow or non-hollow. The control shaft 12 can have an outer diameter of from one to six millimeters (1-6 mm), for example about three millimeters (3 mm).

The control shaft 12 can have a single solid structure or have more than one sub-elements. For example, the control shaft 12 can have an outer sub-shaft 18a and one or more inner sub-shafts 18b. The outer sub-shaft 18a can be a rigid hollow cylinder. The inner sub-shaft 18b can be longitudinally slidably attached inside of the outer sub-shaft 18a. The inner sub-shaft 18b can be translated and/or rotated with respect to the outer sub-shaft 18a, for example to attach the control shaft 12 to and detach the control shaft 12 from the end effector 14 and/or to manipulate or otherwise activate the working tool 16.

The outer sub-shaft 18a can have a hollow lumen longitudinally extending throughout the length of the outer sub-shaft 18a. One or more inner sub-shafts 18b can be positioned inside of the hollow lumen of the outer sub-shaft 18a. The inner sub-shafts 18b can include optical fibers, conducting wires, fluid channels (e.g., catheters), or combinations thereof. The inner sub-shafts 18b can deliver to and receive from the working tool 16 power (e.g., electricity, laser, pneumatic, hydraulic, or combinations thereof), data (e.g., in the form of electricity and/or optical fiber signals), matter (e.g., fluids, gasses, morselized solids, or combinations thereof). For example, one of the inner sub-shafts 18b can have an endoscope and/or light source. Also for example, one of the inner sub-shafts 18b can be a conduit for delivering saline solution and/or compressed air.

The end effector 14 can be a rotating-locking element. The end-effector 14 can be configured to attach to the introducer 8 or control shaft 12 while concurrently detaching from the control shaft 12 or introducer 8, respectively.

The end effector 14 can have a first connector configured to releasably attach to or connect with the introducer 8. The end effector 14 can be configured to have a second connector configured to releasably attach to or connect with the control shaft 12.

The working tool 16 can be one or more cutters, graspers, dissectors, morselizers, drills, clips, energy delivery devices such as electro-cautery devices or pacemakers, drug delivery devices such as syringes or insulin or other drug pumps, implant delivery devices such as sheaths and/or angioplasty balloons for holding and deploying vascular stents or orthopedic screws, rods or grafts, anastomosis devices, excision devices, fluid pressure delivery and/or suction devices, biologic delivery devices, tissue sealing devices such as staplers or suturing needles, visualization devices such as endoscopes, cameras, and lights, or combinations thereof. The working tool 16 can be configured to manipulate or directly affect or alter tissue, and/or collect, receive, and/or transmit data and/or energy.

The tool 16 can deliver drugs or biologically compatible materials. The drugs or biologically compatible materials can may be used for diagnostic or therapeutic purposes. Drugs, implants, or biologics may be enclosed in housing that can be the tool 16 or attached to the tool 16. One example of a drug that can be delivered is insulin. One example of a biologically compatible implant is a metal cage used for anterior spinal fusion. One example of biologicals is stem cells.

The target sites for the use of the surgical device can include the abdominal cavity, the thoracic or chest cavity, a joint capsule, intra-cranial locations, intra-nasal locations such as the nasal sinus, or combinations thereof (e.g., during a procedure implanting a cerebral fluid shunt through the skull and leading to the peritoneal cavity).

FIG. 3a illustrates that the radially outer surface of the end effector 14 can have long and short receiving slots 20a and 20b. The receiving slots 20a and 20b can be configured to slidably receive a structural feature (e.g., a key) of the introducer 8. The receiving slots 20a and 20 can end before the proximal terminal end of the end effector 14. The long receiving slots 20a can extend to the distal terminal end of the end effector 14, for example, to accommodate the structure of the working tool 16.

FIGS. 4a through 4c illustrate that the terminal proximal end of the end effector 14 can have a housing cap 22. The housing cap 22 can be configured to receive the control shaft 12.

The end effector 14 can have a locking ring 24 immediately adjacent to and in rotatable contact with the housing cap 22 on the distal side of the housing cap 22.

The end effector 14 can have a groove ring 26 immediately adjacent to and in rotatable contact with the locking ring 24. The locking ring 24 can be configured to rotate with respect to the groove ring 26 to lock and unlock the end effector 14 from the introducer 8 and the control shaft 14.

The end effector 14 can have an integral housing 28 immediately adjacent to and in rotatable contact with the groove ring 26. The distal end of the integral housing 28 can have a housing working tool interface 32a. The tool 16 can attach to the working tool interface 32a.

The end effector 14 can have an active shaft 30. The active shaft 30 can be located radially inside of the integral housing 28.

The distal end of the active shaft 30 can have a shaft working tool interface 32b. The working tool interfaces 32a and 32b can attach to the working tool 16. The example, the working tool interfaces 32 can have clamps, collets, holes for receiving one or more pins or axles, or combinations thereof. The long receiving slots 20a can extend through the working tool interfaces 32.

The end effector 14 can have an end effector channel 34. The control shaft 12 can be slidably inserted into the end effector channel 34. The control shaft 12 can be rotated within the end effector channel 34 to unlock the end effector 14 from the introducer 8, and concurrently or simultaneously lock the end effector 14 to the control shaft 12.

FIG. 4d illustrates that the axle slot 48 can have a slot first edge axis 624a and a slot second edge axis 624b. An axle slot angle 628 can be formed between the slot first edge axis 624a and the slot second edge axis 624b. The axle slot angle 628 can be from about twenty to one hundred twenty degrees (20°-120°), for example about sixty degrees (60°).

The locking ring key 64 can have a tooth or key first edge axis 626 that can face the slot second edge axis 624b. A key rotation angle 630 can be formed between the tooth or key first edge axis 626 and the slot second edge axis 624b. The key rotation angle 630 can be from about five to ninety degrees (5°-90°), more narrowly from about ten to forty five degrees (10°-45°), for example, about thirty degrees (30°).

The locking key 64 can rotate within the axle slot 48, for example, along the key rotation angle 30. The locking key 64 can abut or interference fit the slot first edge and the slot second edge, limiting rotation of the locking ring 24 with respect to the integral housing 28.

FIGS. 5 and 6 illustrate that the active shaft 30 can have a hollow active shaft channel 36 inside the active shaft 30. The active shaft 30 can have an active shaft key 38 that can extend radially inward from the cylindrical wall of the active shaft 30.

The shaft working tool interface 32b can have one or two shaft slots 40 extending from the distal terminal end of the active shaft 30. The tool 16 can move into or through the shaft slots 40 during use and activation of the tool 16. The shaft working tool interface 32b can have one or two opposed shaft pin hole 42. A pin can be inserted through the shaft pin hole 42 to attach the active shaft 30 to the tool 16. For example, the pin can act as a rotational hinge for a tool 16 having grasping jaws. Also, for example, the pin can intersect control grooves on the jaws, controlling rotation of the jaws, shown in FIG. 13.

FIGS. 7a through 7c illustrate that the integral housing 28 can have a hollow integral housing channel 44. The control shaft 12 can be inserted through the integral housing channel 44.

The proximal end of the integral housing 28 can be a housing axle 46. The housing axle 46 can have an outer diameter less than the outer diameter of the integral housing 28 that is distal to the housing axle 46. The outer circumference of the integral housing 28 can discretely change, forming a sharp shoulder, at the housing axle 46. The housing axle 46 can have a distal housing axle 46a distal to a proximal housing axle 46b. The distal housing axle 46b can have a larger outer diameter than the proximal housing axle 46a. The groove ring 26, and/or locking ring 24 can be rotatable positioned on the distal housing axle 46a. The housing cap 22 and/or locking ring 24 can be positioned on the proximal housing axle 46b. The housing cap 22 can be fixed to or rotatably attached to the housing axle 46.

The groove ring 26, locking ring 24, and housing cap 22 can be located on the radially outer side of the axle 46 and can be rotationally fixed, or rotatable on the axle 46. For example, the axle 46 can have an axle slot 48. The respective keys extending radially inward from the groove ring 26 and locking ring 24 can extend into or through the axle slot 48. The rotation of the locking ring 24 and the housing cap 22 can be limited by the respective keys abutting and interfering with the side of the axle slot 48.

The housing working tool interface 32a can have one or more housing pin holes 50.

Figure 8B:
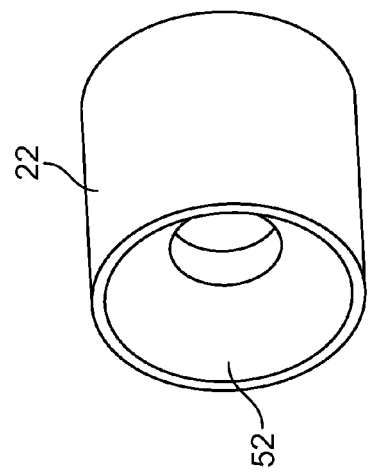

FIGS. 8a and 8b illustrate that the housing cap 22 can have a hollow housing cap channel 54 that can extend through the entire length of the housing cap 22. The proximal face of the housing cap 22 can have a housing cap receiving mouth 52 that can be slanted toward the housing cap channel, for example, to route the control shaft 12 into the housing cap channel 54. The housing cap 22 can have a housing cap shoulder 56 that can be a reduced inner diameter at the proximal end of the housing cap channel 54. The housing cap shoulder 56 can abut against and/or affix to the proximal terminal end of the integral housing 28.

Figure 9:
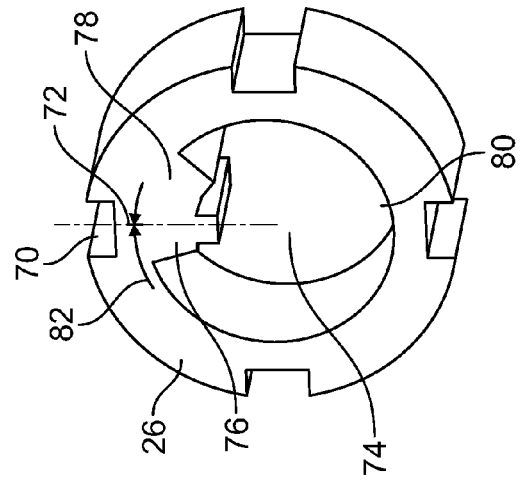
FIG. 9 illustrates a variation of the locking ring.

FIG. 9 illustrates that the locking ring 24 can have one, two, three, four or more locking ring slots 58. The locking ring slots 58 can be part of the length of the receiving slots 20. The locking ring slots 58 can be evenly or unevenly angularly distributed around the outer circumference of the locking ring 24. For example, a first locking ring slot 58 can be about 90° away from the adjacent locking ring slot 58.

The locking ring slots 58 can each have a locking ring slot axis 60. The locking ring slot axis 60 can extend from the center of the locking ring 24 through the center of the locking ring slot 58.

The locking ring 24 can have a hollow locking ring channel 62. The locking ring 24 can have a locking ring key 64 that can extend radially inward into the locking ring channel 62 from the inner wall of the locking ring 24.

The locking ring key 64 can have a locking ring key axis 66. The locking ring key axis 66 can extend from the center of the locking ring 24 through the center or most radially inward portion of the locking ring key 64.

A locking ring key angle 68 can be formed between the locking ring key axis 66 and the nearest locking ring slot axis 60. The locking ring key angle 68 can have an absolute value from about five to ninety five degrees (5°-95°), more narrowly from about five to forty five degrees (5°-45°), more narrowly from about for example about twenty degrees (20°) or about thirty degrees (30°).

Figure 10:
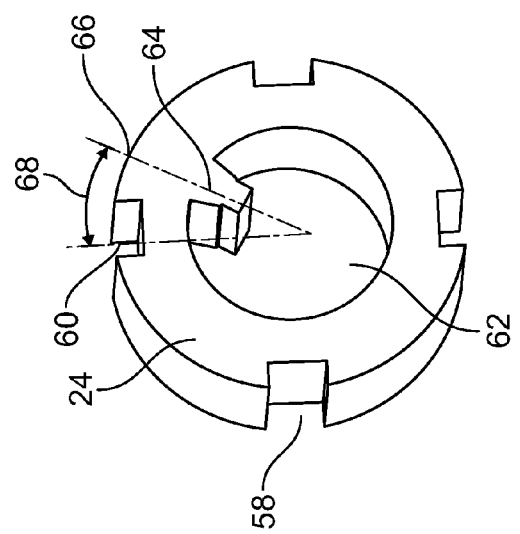
FIG. 10 illustrates a variation of the groove ring.

The locking ring key 64 can be inserted through the axle slot 48. The locking ring key 64 can be angularly smaller than the axle slot 48. For example, the locking ring can rotate from about to ninety five degrees (5°-95°), more narrowly from about five to forty five degrees (5°-45°), for example, twenty degrees (20°) or about thirty degrees (30°) within the axle slot 48. FIG. 10 illustrates that the groove ring 26 can have can have one, two, three, four, or more groove ring slots 70. The groove ring slots 70 can be part of the length of the receiving slots 20. The groove ring slots 70 can be evenly or unevenly angularly distributed around the outer circumference of the groove ring 26. For example, a first groove ring slot 70 can be about ninety degrees (90°) away from the adjacent groove ring slot 70.

The groove ring slots 70 can each have a groove ring slot axis 72. The groove ring slot axis 72 can extend from the center of the groove ring 26 through the center of the groove ring slot 70.

The groove ring 26 can have a hollow groove ring channel 74. The groove ring 26 can have a groove ring key 76 that can extend radially inward into the groove ring channel 74 from the inner wall of the groove ring 26.

The groove ring key 76 can have a groove ring key axis 80. The groove ring key axis 80 can extend from the center of the groove ring 26 through the center or most radially inward portion of the groove ring key 76.

A groove ring key angle 82 can be formed between the groove ring key axis 80 and the nearest groove ring slot axis 72. The groove ring key angle 82 can have an absolute value from about zero to forty five degrees (0-45°), more narrowly from about zero to five (0-5°), for example about zero degrees (0°).

The groove ring key 76 can be inserted through the axle slot 48. The groove ring key 76 can be angularly about equal to or smaller than the axle slot 48. For example, the groove ring 26 can be rotationally fixed to the axle slot 48, or can rotate about zero degrees (0°) within the axle slot 48.

Figure 11A:
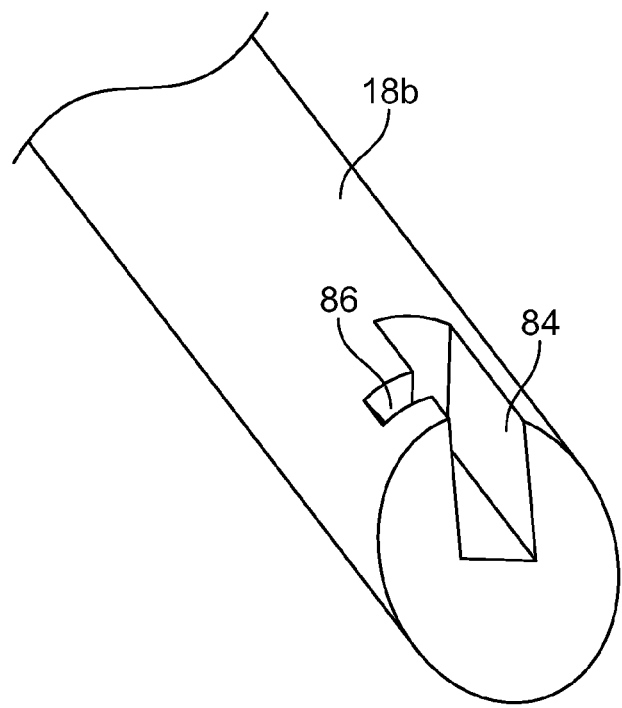
FIGS. 11a and 11b are close-up end perspective and side perspective views, respectively, of a variation of the distal end of the inner sub-shaft.
Figure 11B:
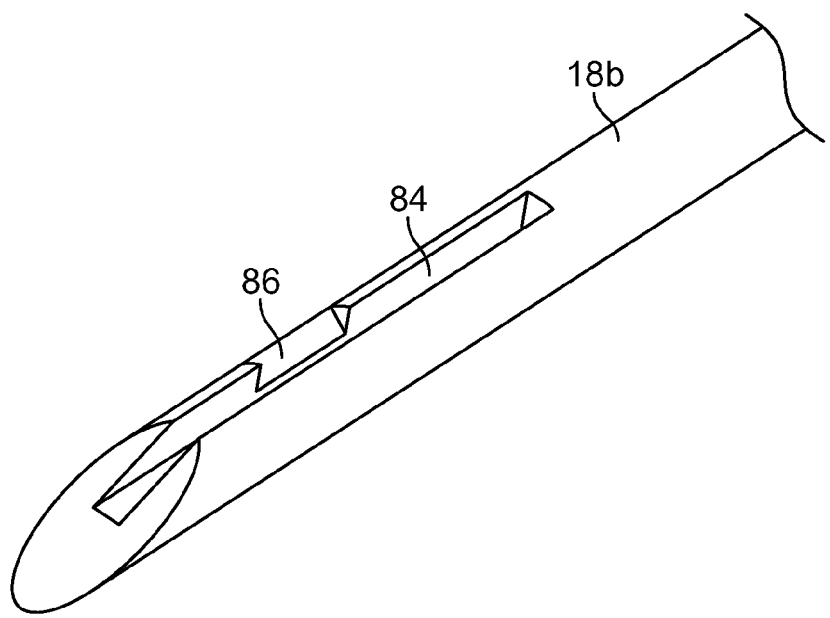

FIGS. 11*a* and 11*b* illustrate that the inner sub-shaft 18*b* can have an inner sub-shaft longitudinal slot 84 that can extend longitudinally to the distal terminal end of the inner sub-shaft 18*b*. The inner sub-shaft longitudinal slot 84 can extend radially from about the center of inner sub-shaft 18*b* to the circumference of the inner sub-shaft 18*b*. The inner sub-shaft 18*b* can have an inner sub-shaft angular notch 86 that can extend angularly from about half-way along the inner sub-shaft longitudinal slot 84. The radial inside of the inner sub-shaft angular notch 84 can have a slant or chamfer.

FIGS. 12*a* and 12*b* illustrate that the outer sub-shaft 18*a* can have an outer sub-shaft longitudinal slot 88 that can extend longitudinally to the distal terminal end of the outer sub-shaft 18*a*. The outer sub-shaft longitudinal slot 88 can extend radially from the inner circumference of the outer sub-shaft 18*a* to the outer circumference of the outer sub-shaft 18*a*. The outer sub-shaft 18*a* can have an outer sub-shaft angular notch 90 that can extend angularly from about half-way along the outer sub-shaft longitudinal slot 88.

FIG. 13 illustrates that the tool 16 can have a hinged tool head, such as a clamping grasper jaw. The tool 16 can have a first jaw 92*a* and a second jaw 92*b* opposed to the first jaw 92*a*. The jaws 92 can each have a jaw pin hole 94. A jaw pin or jaw axle can be inserted through the jaw pin holes 94. The first jaw 92*a* and second jaw 92*b* can be rotatably hinged to the jaw pin. The jaw pin can be rotatably or hingedly attached to the housing pin hole 50. The jaws 92 can rotate about the jaw pin.

The first jaw 92*a* can have a first control groove, guide or slot 96*a*. The second jaw 92*b* can have a second control groove, guide or slot 96*b*. A control pin can be slidably positioned through the first control groove 96*a* and the second control groove 96*b*. The control pin can be rotatably or hingedly attached to the shaft pin hole 42. The active shaft 30 can be translated proximally and distally with respect to the integral housing 28 in the integral housing channel 44. As the active shaft 30 translates, the control pin can slide through the control grooves 96, for example, forcing the jaws 92 to rotated about the jaw pin.

FIGS. 14*a* through 14*c* illustrate that the introducer 8 can have a hollow introducer channel 98. The introducer channel 98 can extend the entire length of the introducer. The introducer channel 98 can be as long or longer than the length from the distal end of the housing cap to the distal end of the working tool 16.

The introducer 8 can have one, two, three, four or more introducer keys 600. The introducer keys 600 can extend radially inward from the cylindrical wall of the introducer 8. The introducer keys 600 can be at the distal terminal end of the introducer 8. The introducer keys 600 can be equally or unequally angularly distributed around the introducer 8. For example, each introducer key 600 can be about ninety degrees (90°) away from the adjacent introducer key 600.

FIGS. 15*a* and 15*b* illustrate that the introducer 8 can be integral with or attached to the introducer rod 10. The introducer rod 10 can be beside or lateral to the introducer 8. A longitudinal axis through the center of the introducer channel 98 can be parallel with and offset from a longitudinal axis through the center of the introducer rod 10.

The introducer rod 10 can have an introducer rod channel 602. The introducer rod channel 602 can be configured to fixedly or releasably attach to an elongated member, such as a straight or articulating shaft or rod.

FIGS. 16a and 16b illustrate that the introducer 8 can have an open introducer channel 98. The introducer 8 can form an arc or incomplete boundary around the introducer channel 98. The introducer 98 can be laterally snapped or placed on and off the side of the end effector 14.

Figure 17A:
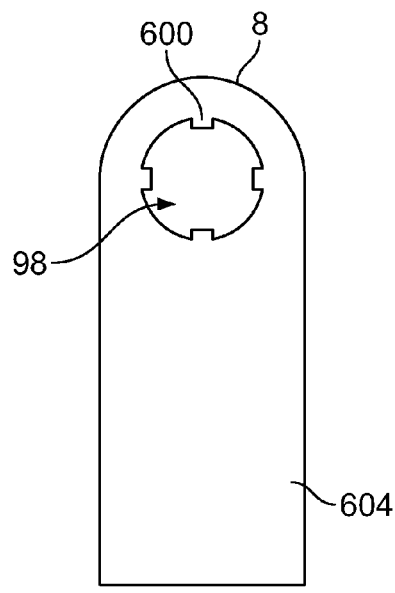
FIGS. 17a and 17b are end and perspective views, respectively, of a variation of the introducer.
Figure 17B:
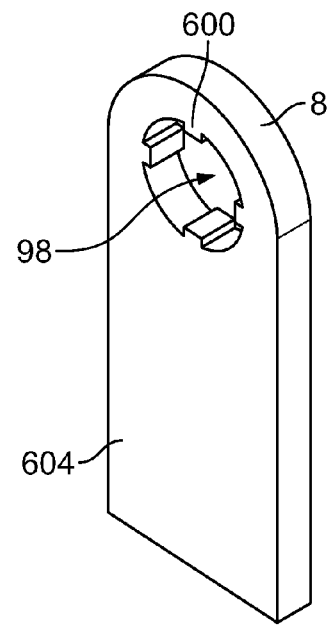

FIGS. 17a and 17b illustrate that the introducer 8 can have an introducer handle 604. The introducer handle 604 can be flat and extend from the wall of the introducer 8. The introducer handle 604 can be coplanar with the introducer keys 600.

Figure 17C:
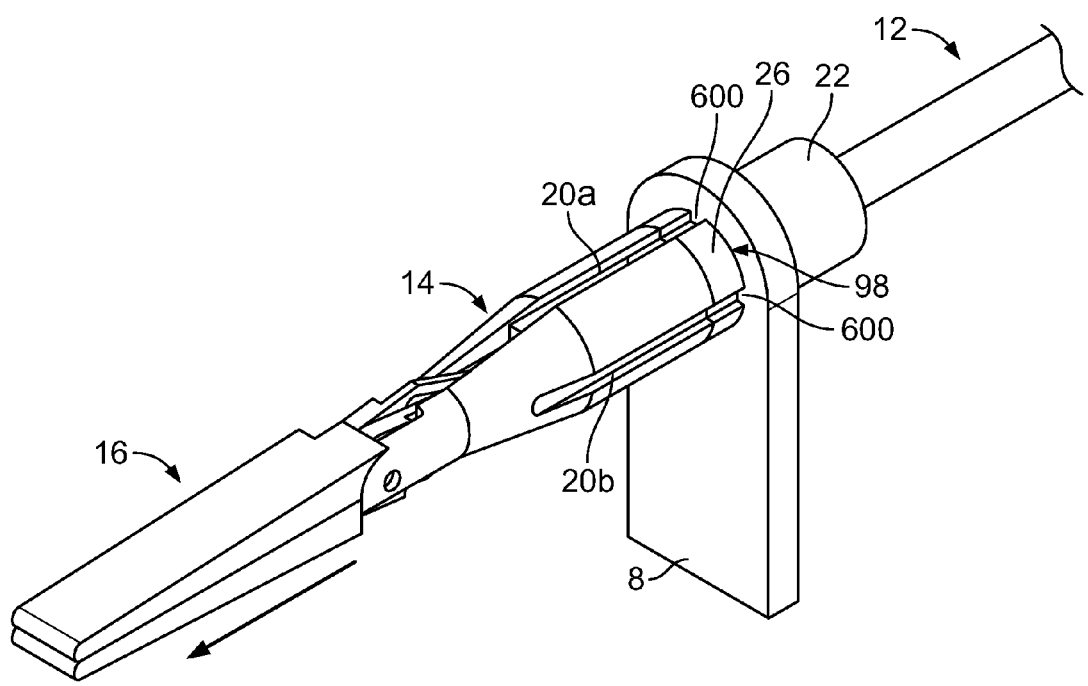
FIG. 17c is a perspective view of a method for sliding the introducer on the end effector.

FIG. 17c illustrates that the introducer 8 can be slid onto the end effector 14, and/or the end effector 14 can be translated or pushed, as shown by arrow, through the introducer channel. The introducer keys can abut the housing cap 22. The introducer keys can be equal to or less than the length of the locking ring 24. The groove ring 26 can be rotationally unobstructed by the introducer 8 when the introducer 8 is positioned with the introducer keys in the locking ring slots.

Figure 18A:
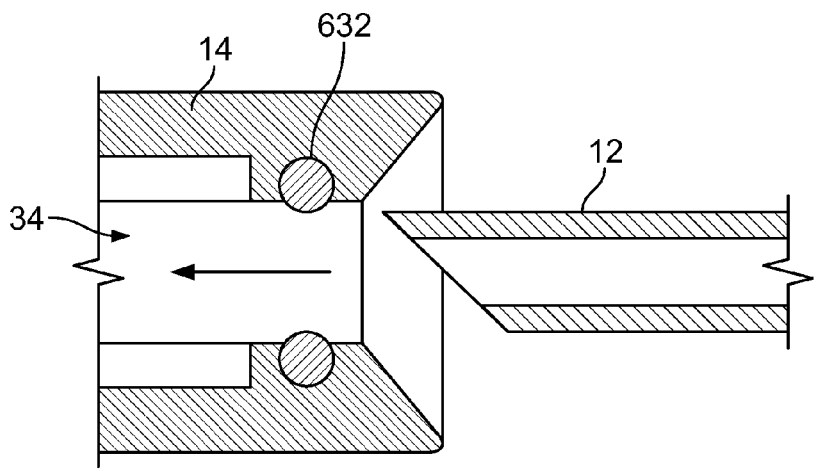
FIGS. 18a and 18b are close-up cross-sectional views of a variation of inserting the control shaft into an end effector.
Figure 18B:
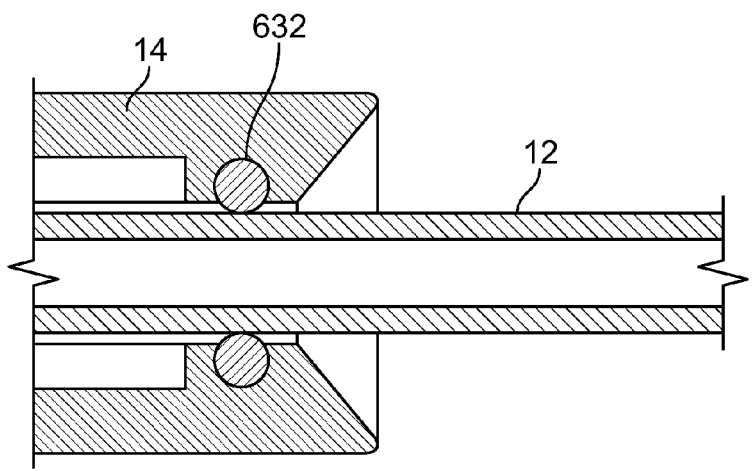

FIGS. 18a and 18b illustrate that the end effector 14 can have an end effector seal 632, such as a gasket, o-ring, along the inner circumference of the end effector 14 along the end effector channel 34. As shown by arrow, the control shaft 12 can be inserted into the end effector channel 34 past the end effector seal 632. The end effector seal 632 can form a fluid-tight seal between the inner circumference of the end effector 14 and the outer circumference of the control shaft 12. The end effector seal 632 can be tight enough and create enough frictional force against the control shaft 12, that the end effector seal 632 can fix the control shaft 12 to the end effector 14. The end effector 14 can then be detached from the introducer 8 and can remain fixed to the control shaft 12.

Figures 19A, 19B:
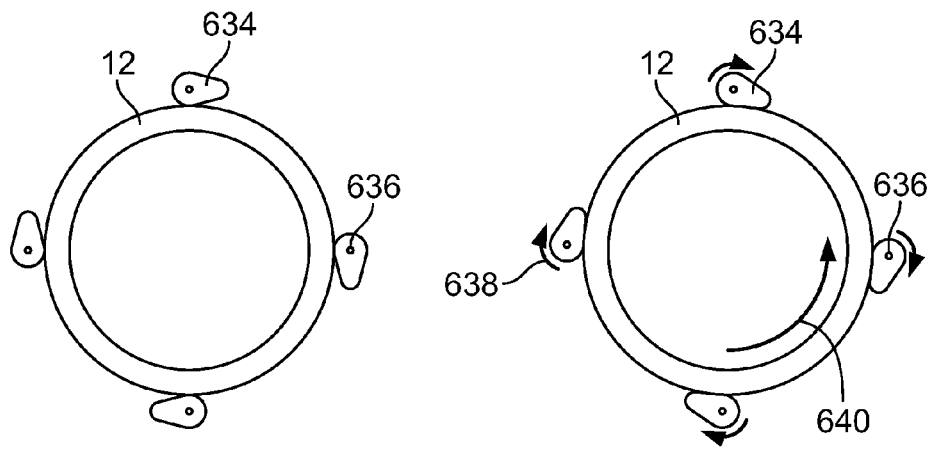
FIGS. 19a and 19b are transverse cross sections of a control shaft in a variation of a cam configuration in unlocked and locked configurations, respectively.

FIG. 19a illustrates that the end effector 14 can have one, two, three, four (as shown) or more circumferentially distributed locking cams 634. The locking cams 634 can each rotate about locking cam axles 636. The locking cams 634 can be used in place of or in addition to the slots and keys. The control shaft 12 can be slid into the end effector channel defined within the locking cams 634 when the locking cams 634 are in an unlocked configuration.

FIG. 19b illustrates that the control shaft 12 can be rotated, as shown by arrow 640. The rotation of the control shaft 12 can rotate, as shown by arrows 638, the cams 634. The cams 634 can be rotated until the cam lobes lock against the control shaft 12. The locking cams 634 can then lock to the control shaft 12, fixing and attaching the end effector 14 to the control shaft 12. The control shaft 12 can then be rotated in the opposite direction relative to the locking cams 634 to release and detach from the end effector 14.

Figure 20:
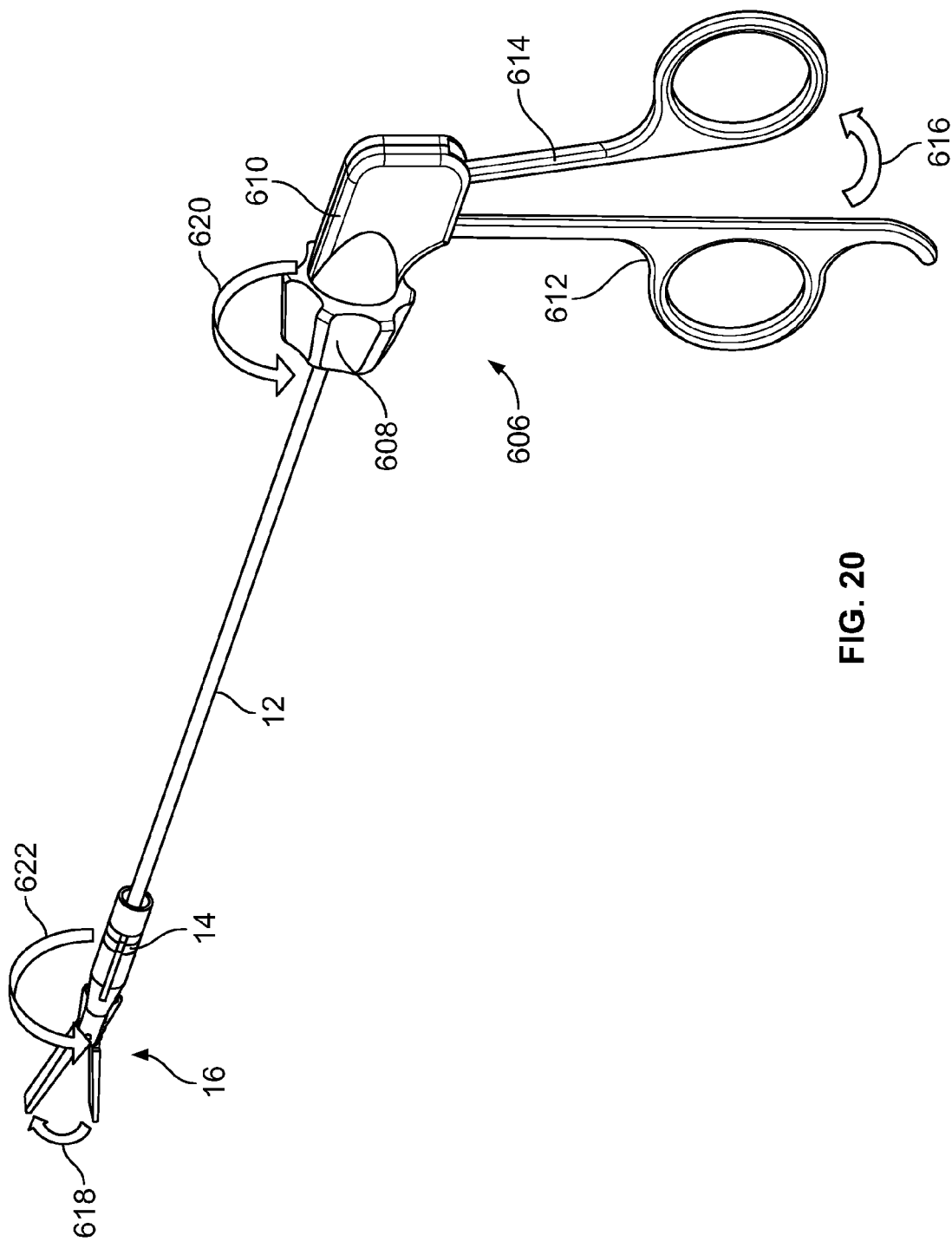
FIG. 20 illustrates a method for mechanical operation of the device.

FIG. 20 illustrates that the proximal end of the control shaft 12 can be attached a control shaft handle 606. The distal end of the control shaft handle 608 adjacent to the control shaft 12 can have a twist control knob 608. Rotating, as shown by arrow 620, the twist control knob 608 can calibrate and/or attach and lock, as shown by arrow 622, the end effector 14 to the control shaft 12 (e.g., and concurrently unlock and detach the end effector from the introducer 8), or detach and unlock the end effector 14 from the control shaft 12 (e.g., and concurrently attach and lock the end effector 14 to the introducer 8), and/or rotate the tool 16 during use.

The control shaft handle 606 can have a stock 610. The twist control knob 608 can be attached to the stock 610. The control shaft 12 can be attached to the stock 610. The inner sub-shafts 18b, such as catheters, power cords, and fiber optics, implants such as embolic coils and morselized bone, fluids, such as compressed air, carbon dioxide, and saline solution, or combinations thereof, can be inserted through the stock 610 and into the outer sub-shaft 18a.

A hand rest 612 can extend from the stock 610. The hand rest 612 can have a finger hole and an open finger rest. The hand rest 612 can be fixed to and/or integral with the stock 610.

A translation control trigger 614 can extend from the stock 610. The control trigger 614 can have a finger hole. The control trigger 614 can be rotatably attached to the stock 610. Rotating (e.g., pulling), as shown by arrow 616, the control trigger 614 can activate the tool 16, such as rotating the jaws, as shown by arrow 618, deploying fluid, delivering electricity, or combinations thereof.

FIG. 21a illustrates that the tool 16 can be scissors. The first jaw 92a can be fixed to the integral housing 28. The second jaw 92b can rotate with respect to the first jaw 92a. The insides of the jaws 92 can be sharpened and traumatic.

FIGS. 21b and 21c illustrate that the tool 16 can be a clip applier. The first jaw 92a and second jaw 92b can hold one or more clips 642. The jaws 92 can rotate inward, outward, extend, contract, or combinations thereof to deploy the clips 642.

FIGS. 21c through 21e illustrate that the tool 16 can be an electrosurgery or cautery tool. For example, the distal end of the tool can have an RF electrode 644. The electrode 644 can transmit non-RF energy. For example, the electrode 644 can be a cooling probe, an ultrasound probe, or combinations thereof.

Figure 22:
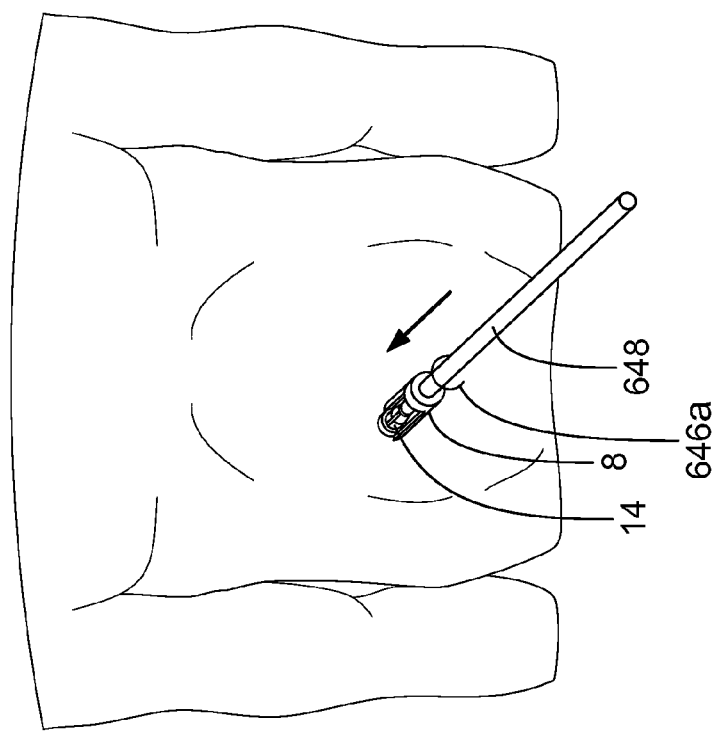
FIG. 22 illustrate a variation of a method for delivering the end effector and tool into the abdominal cavity.

FIG. 22 illustrates that an introducer 8 can be attached to an end effector 14, for example with a tool 16. The introducer 8 can be at the end of a delivery system 648 delivered through a first access site 646a past an abdominal wall W and into an abdominal cavity. The delivery system 648 can have one or more scopes, fluid lumen, and/or power cords. The first access site 646a can be at or directly adjacent to the umbilicus, navel or bellybutton.

FIGS. 22, 23a, 23b, 27b, and 28c illustrate that first, second, and third access sites 646a, 646b, and 646c, or combinations thereof can be created in the abdominal wall W. The access sites 646 can be incisions, punctures, or combinations thereof. Trocars or cannulas can be placed in one or more (e.g., all) of the access sites.

The first access site (e.g., the site in the umbilicus through which the introducer 8 can be inserted) 646a and/or the trocar in the first access sites 646a can have a first access site inner diameter from about 1 mm (0.04 in.) to about 30 mm (1.2 in.), more narrowly from about 5 mm (0.2 in.) to about 30 mm (1.2 in.), more narrowly from about 10 mm (0.40 in.) to about 20 mm (0.79 in.), for example about 12 mm (0.47 in.).

The second and third access sites 646b and 646c (e.g., the sites through which first and/or second control shafts 12 and 12' can be inserted) and/or trocar in the second and third access sites can have a supplemental access site inner diameter from about 0.1 cm to about 3 cm, more narrowly from about 1 mm (0.04 in.) to about 5 mm (0.2 in.), for example about 2 mm (0.08 in.) or about 3 mm (0.1 in.). For example, the trocar or introducer can be from about 4 French to about 20 French introducer (e.g., hemostasis) sheaths can be used, more narrowly from about 5 French to about 10 French, for example 6 French or 7 French. (6 French sheath=2 mm) (0.013 in/French).

The first access site 646a can be less than about 0.5 cm from the second access site. The second access site 646b can be more than about 0.5 cm from the first access site 646a. A third access site 646c can be less than about 0.5 cm from the second access 646b site and/or first access site 646a. The third access site 646c can be more than about 0.5 cm from the second access site 646b and/or the first access site 646c.

Figure 23A:
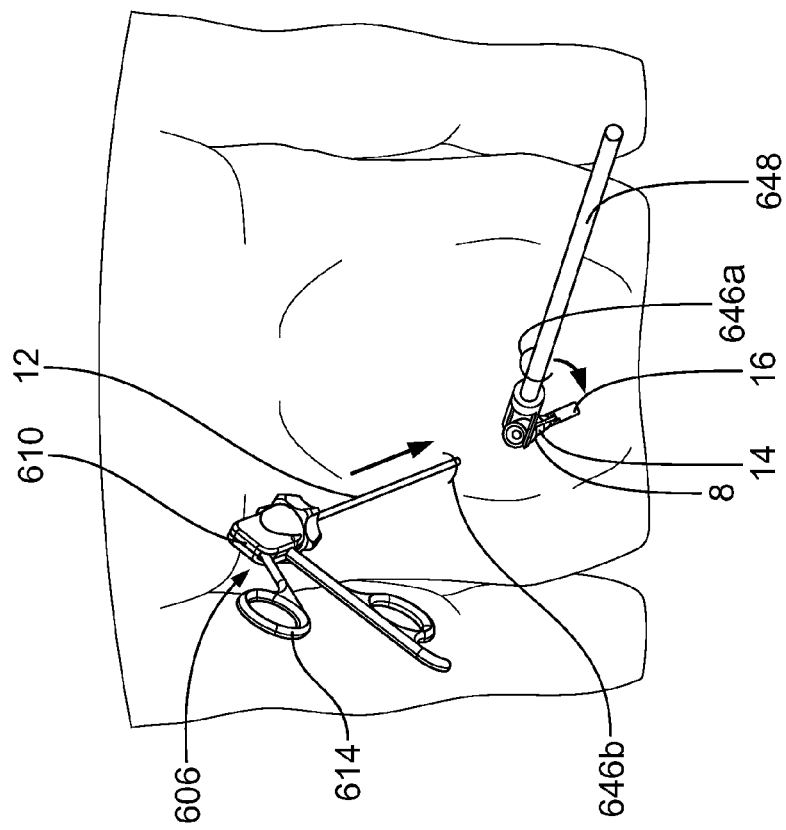
FIGS. 23a and 23b illustrate a variation a method of inserting the control shaft into the abdominal cavity and into the end effector.
Figure 23B:
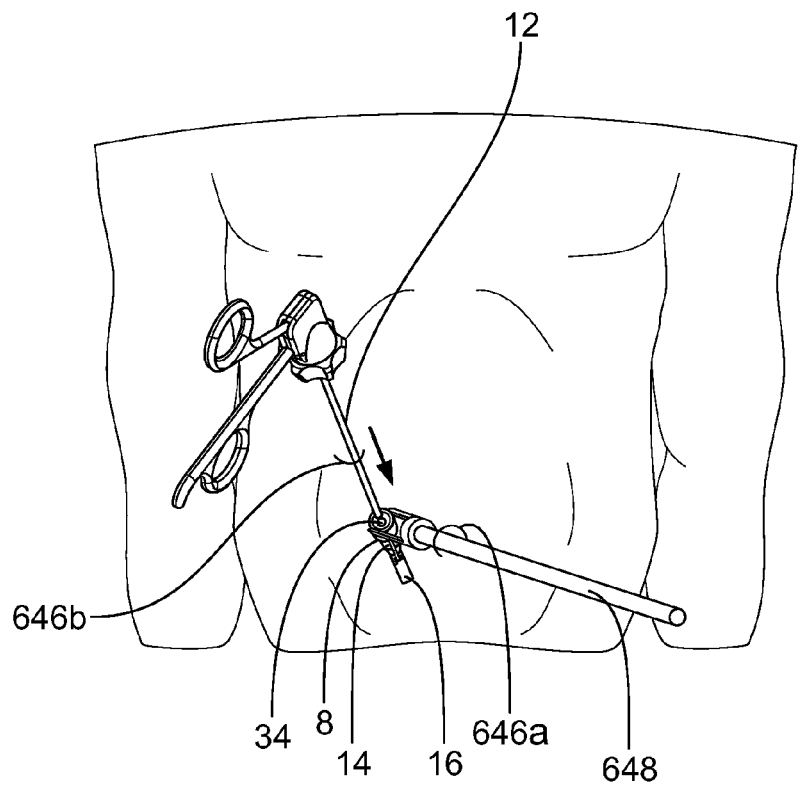

FIGS. 23a and 23b illustrate that the control shaft 12 can be inserted through the second access site 646b. The introducer 8 can rotate or articulate at the end of the delivery system 648, for example exposing the proximal end of the end effector 14. The control shaft can be moved toward the end effector channel 34, as shown in FIGS. 23b and 24.

Figure 24:
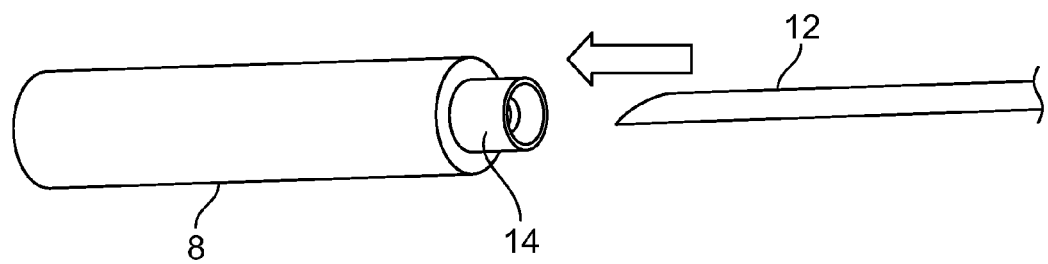
FIG. 24 is a close up view of a method for inserting the control shaft into the end effector.

FIG. 24 illustrates that at the target site, such as in an inflated abdominal cavity, the control shaft 12 can be slidably inserted into the end effector 14 channel when the end effector 14 is attached to the introducer 8.

Figure 25A:
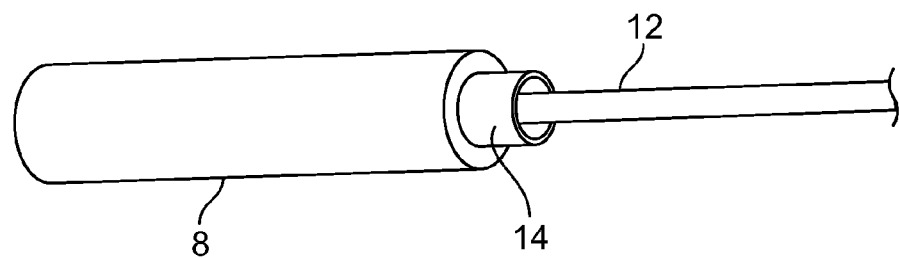
FIGS. 25a through 25n are various close-up views (with various elements shown in partial or complete see-through for illustrative purposes) of the end effector, introducer and control shaft in a configuration with the introducer attached to the end effector and the control shaft in the end effector channel but not attached to the end effector. In these views, the end effector is locked to the introducer.
Figure 25B:
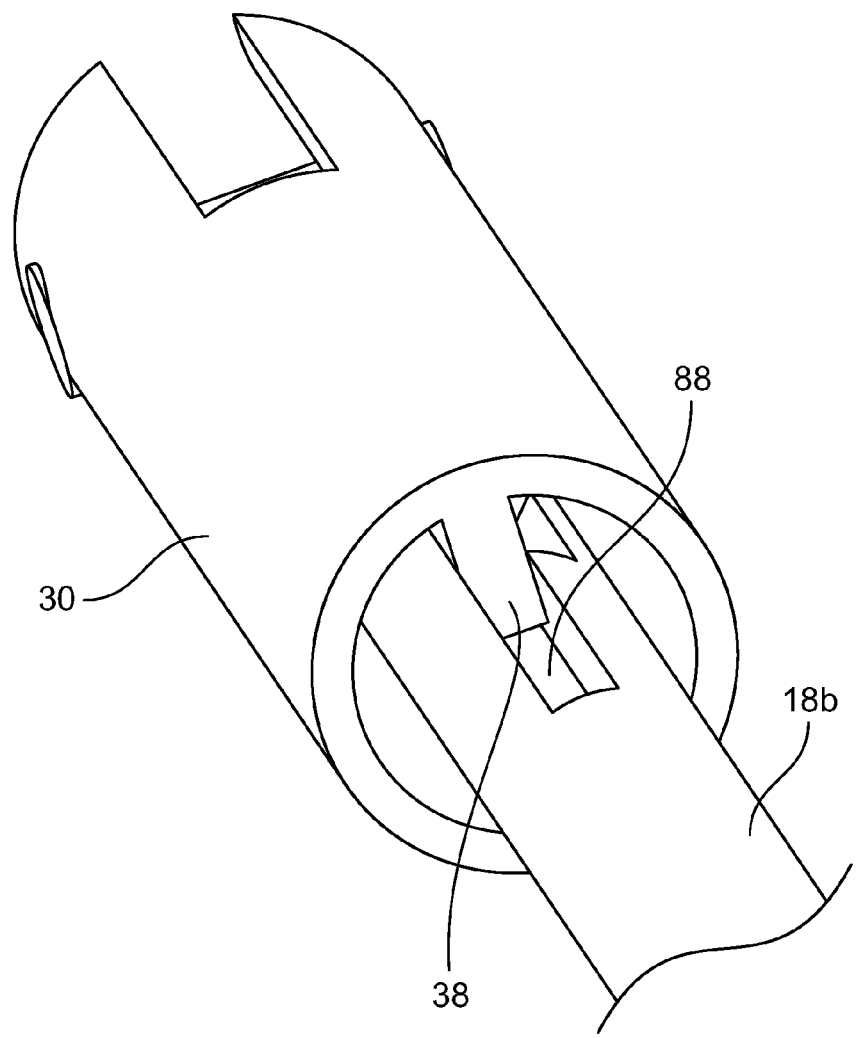
Figure 25M:
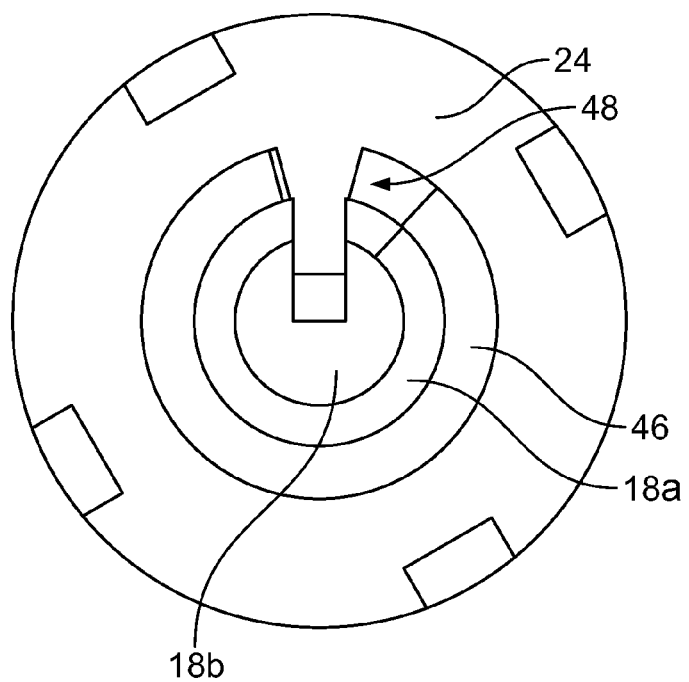
Figure 25N:
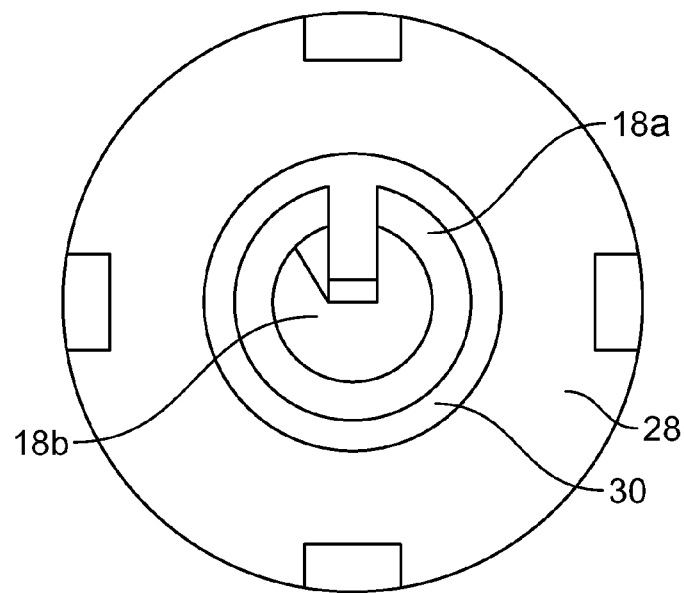

FIGS. 25a through 25n illustrates that the control shaft 12 can be slid into the end effector 14. The external receiving slots 20 can be misaligned. For example, the locking ring slots 58 can be non-colinear with the groove ring slots 70. The misaligned slots 58 and 70 can lock the introducer 8 to the end effector 14.

The internal keys can be collinear. The sub-shaft longitudinal slots 84 and 88 can slide over the internal keys. The actuator key 38 can intersect and be engaged by, and slide along the inner and outer sub-shaft longitudinal slots 84 and 88. The groove ring key 76 can slide along the outer sub-shaft longitudinal slot 88. For example, the groove ring key 76 can extend enough to engage and intersect the outer sub-shaft longitudinal slot 88 and not long enough to engage and intersect the inner sub-shaft longitudinal slot 84. The locking ring 24 can intersect and be engaged by, and slide along the inner and outer sub-shaft longitudinal slots 84 and 88.

Figure 26A:
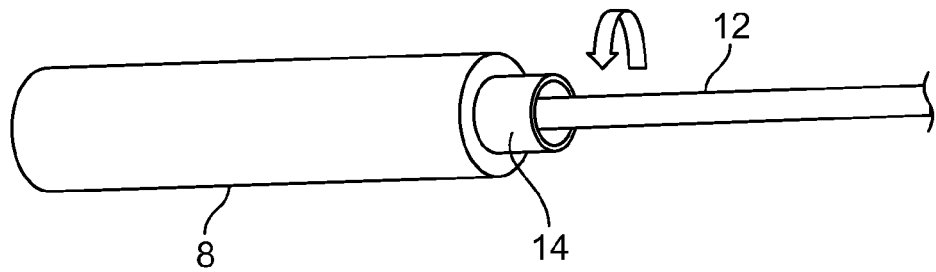
FIGS. 26a through 26p are various close-up views (with various elements shown in partial or complete see-through for illustrative purposes) of the end effector, introducer and control shaft in a configuration with the introducer detached from the end effector and the control shaft in the end effector channel and attached to the end effector. In these views, the end effector is unlocked from the introducer.
Figure 26B:
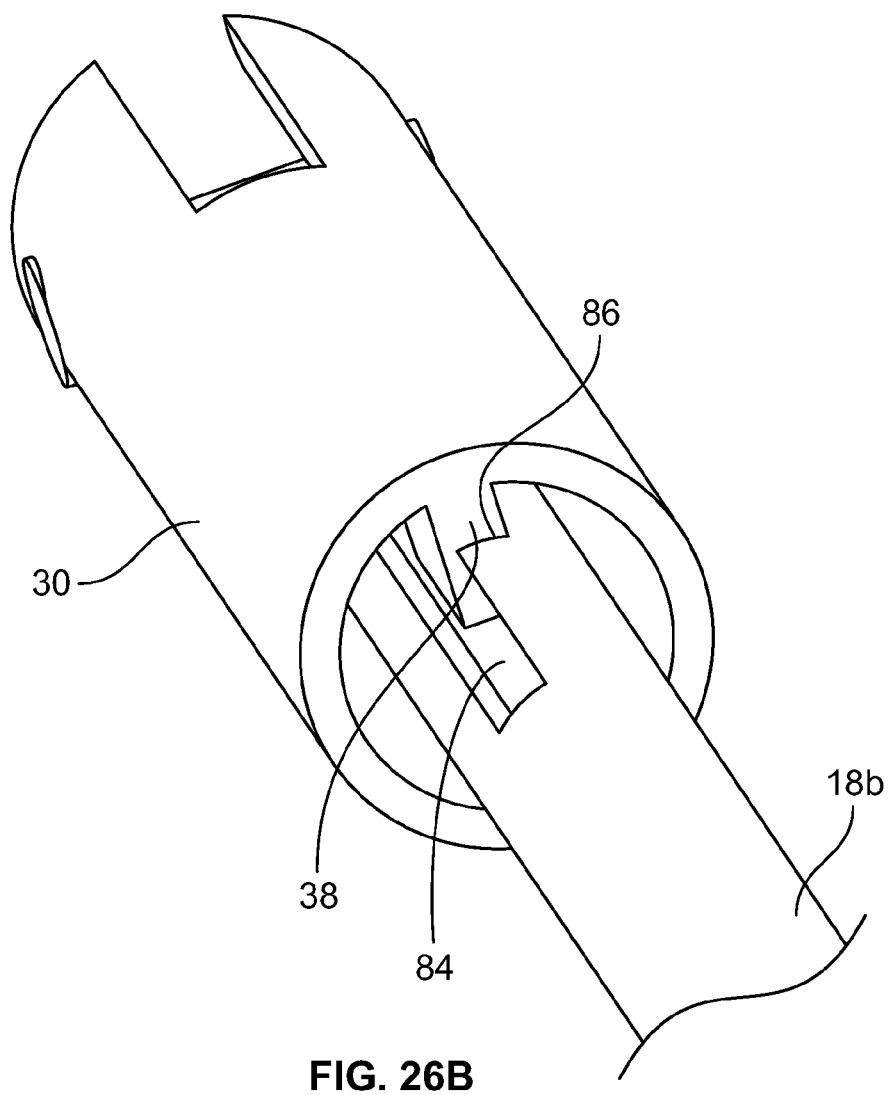
Figures 26C, 26D:
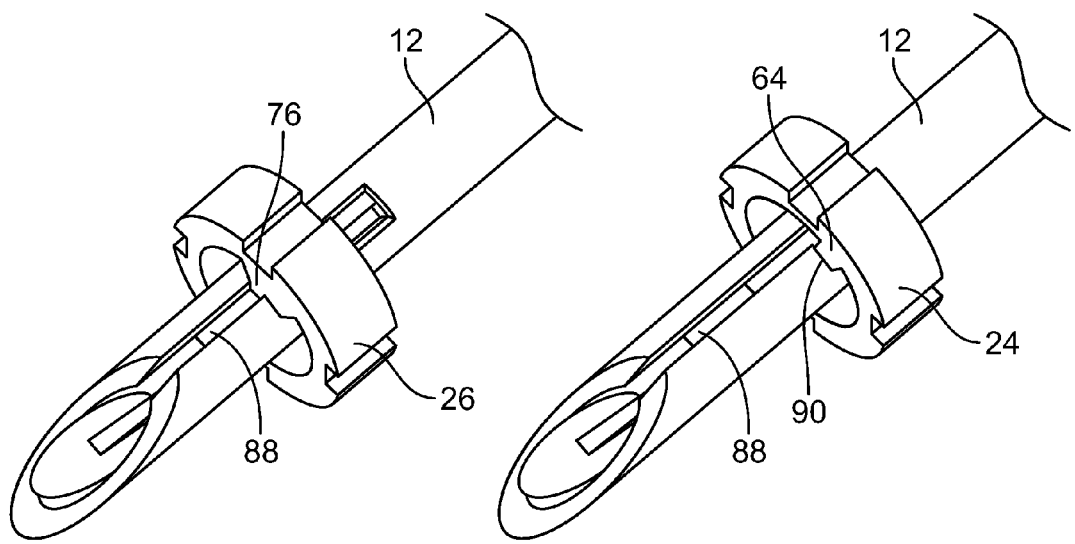
Figures 26E, 26F:
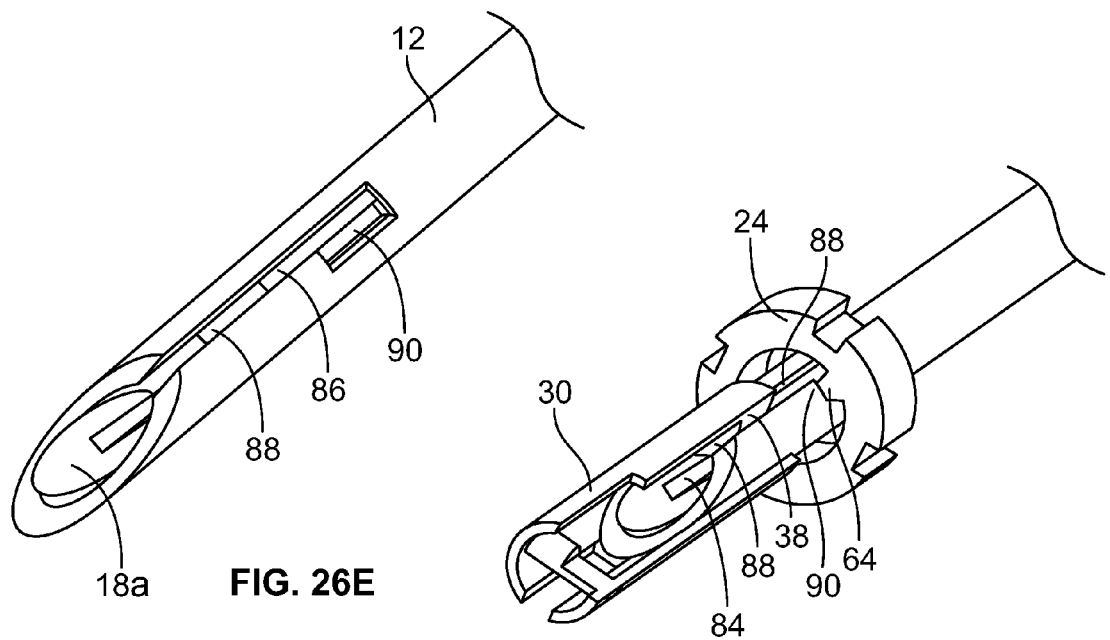
Figure 26K:
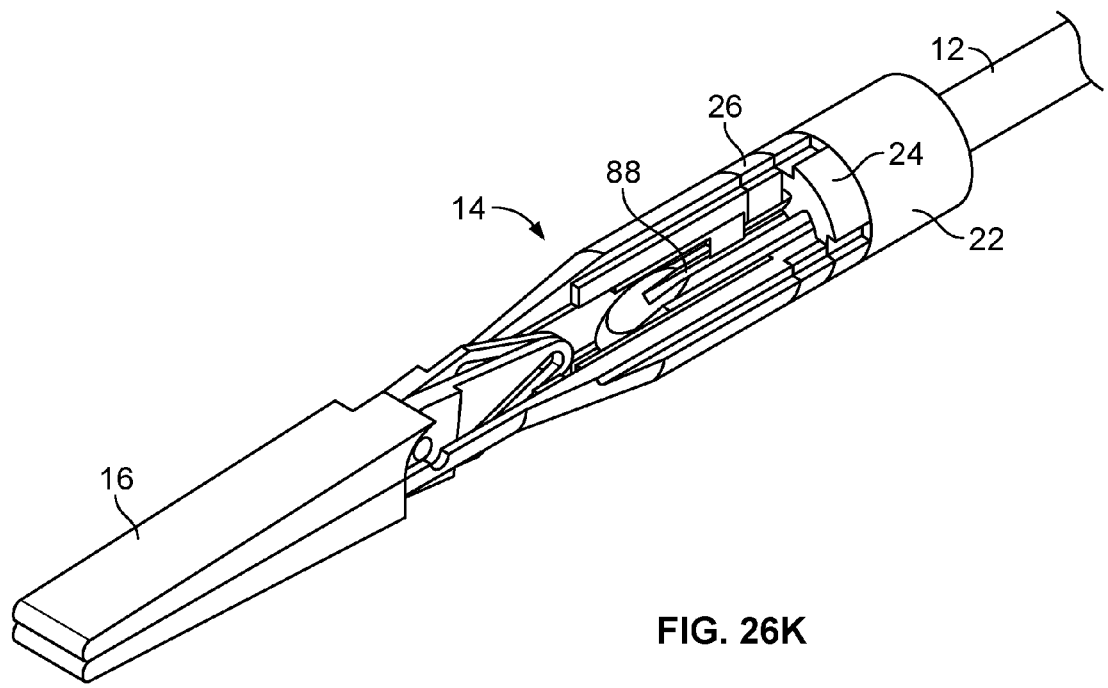
Figure 26L:
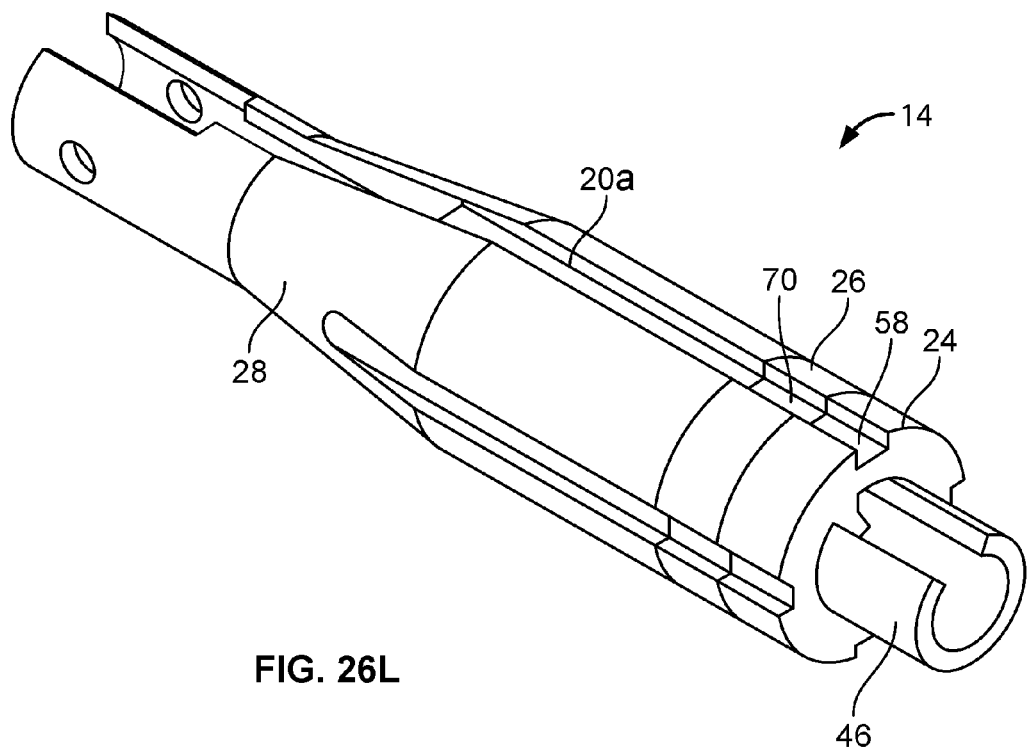
Figure 26M:
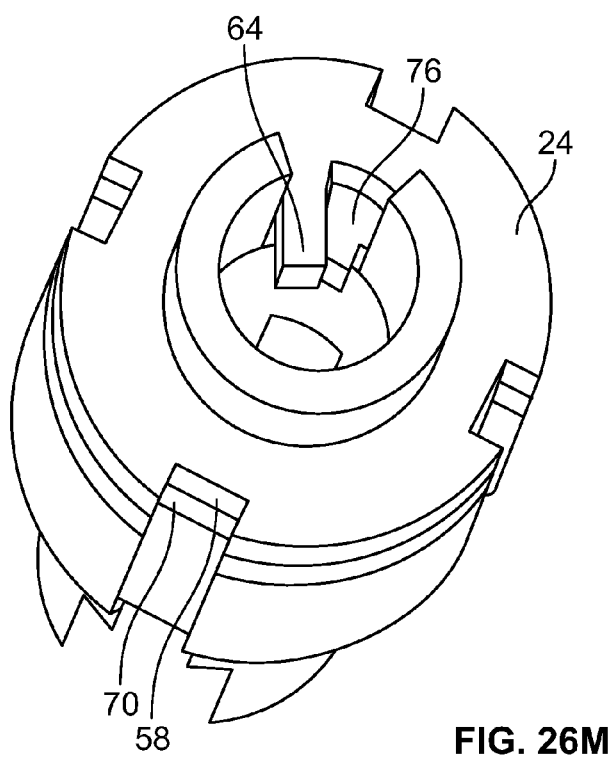
Figure 26N:
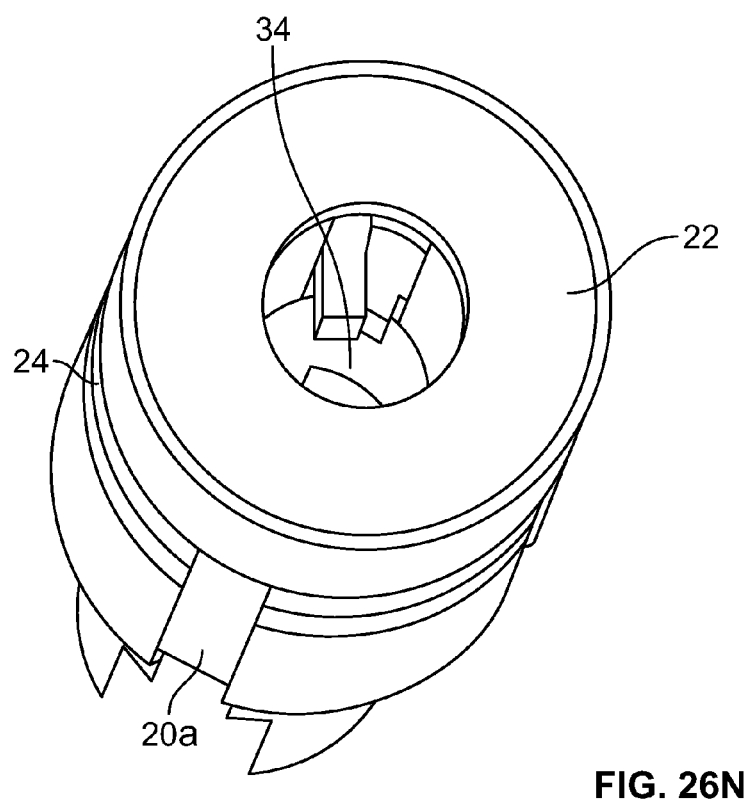
Figure 26O:
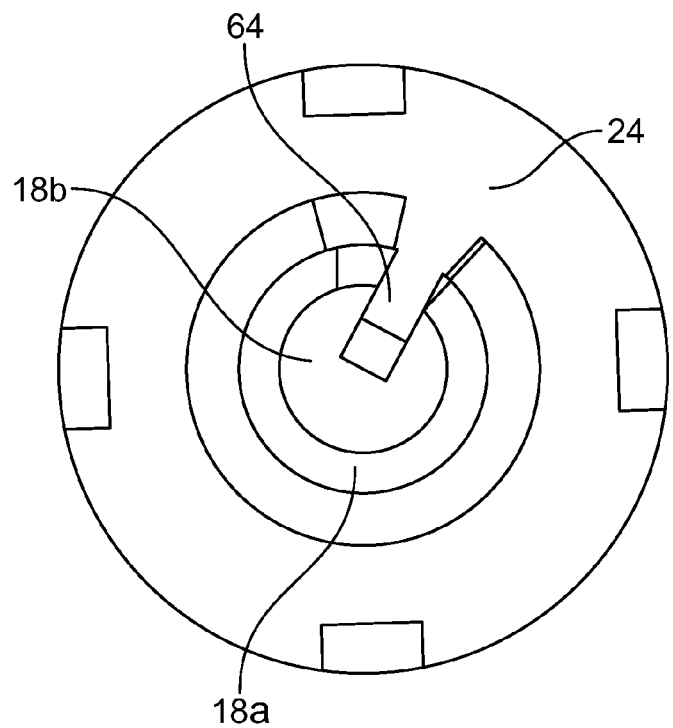
Figure 26P:
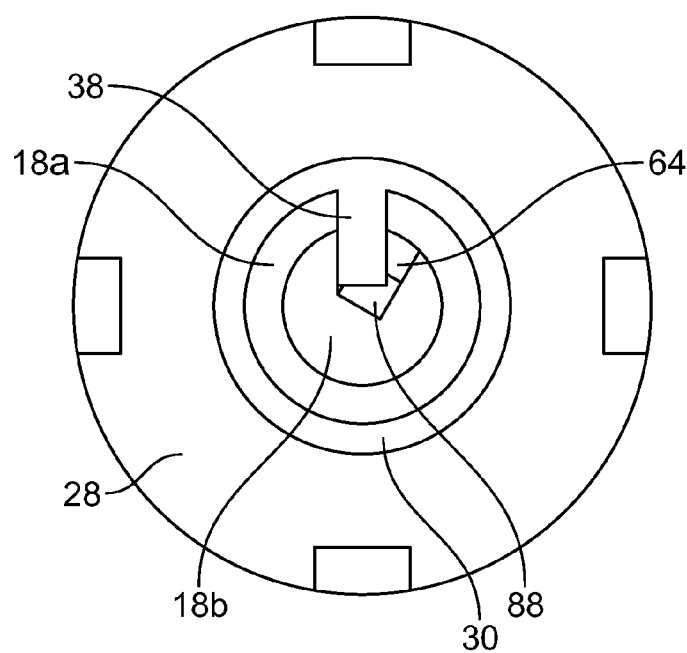

FIGS. 26a through 26p illustrate that the control shaft 12 can be rotated, as shown by arrow, with respect to the introducer 8 and/or the introducer 8 can be rotated with respect to the control shaft 12 (i.e., the former and latter can be same rotational result). The rotation of the control shaft 12 can be the rotation of the entire control shaft 12, or the rotation of the outer or inner sub-shaft 18a or 18b with respect to the other sub-shaft 18b or 18a. The rotation shown can detach the end effector 14 from the introducer 8 and simultaneously or concurrently attach the end effector 14 to control shaft 12.

The actuator key 38 can engage the inner sub-shaft longitudinal notch 90. During use, the actuator shaft 30 can be longitudinally fixed to the inner sub-shaft 18b. The control shaft inner sub-shaft 18b can be longitudinally translated with respect to the outer sub-shaft 18a to activate the tool 16.

The groove ring key 76 can remain in the outer sub-shaft longitudinal notch 88. The locking ring key 64 can rotate into the outer sub-shaft angular notch 90 and remain in the inner sub-shaft angular slot 84. The end effector 14 can be locked to the control shaft 12.

The receiving slots 20 can align and allow the introducer 8 to slide off the end effector 14. The locking ring slot 58 can be collinear with the groove ring slot 70. The introducer keys 600 can slide along the receiving slots 20.

Figure 27A:
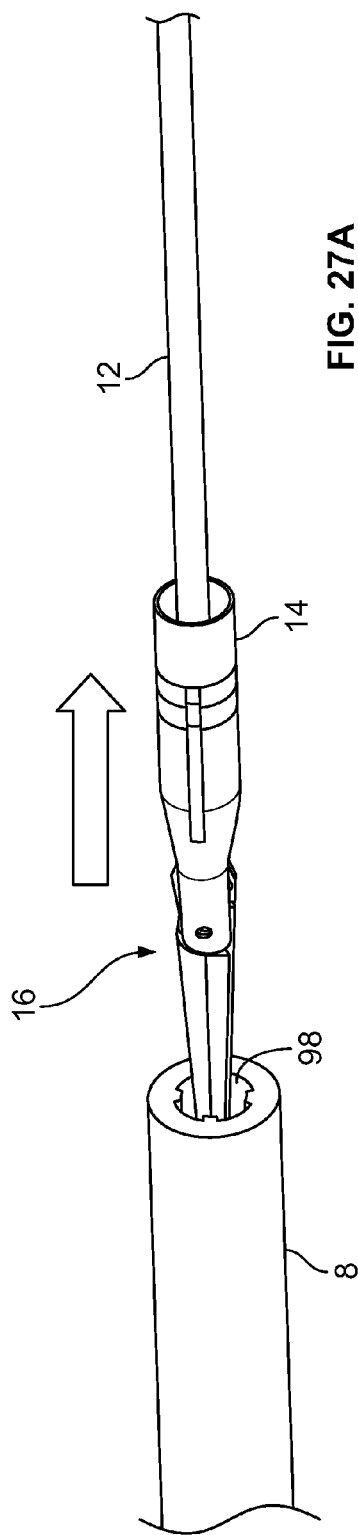
FIGS. 27a and 27b illustrate a variation of a method for removing the end effector and tool from the introducer.
Figure 27B:
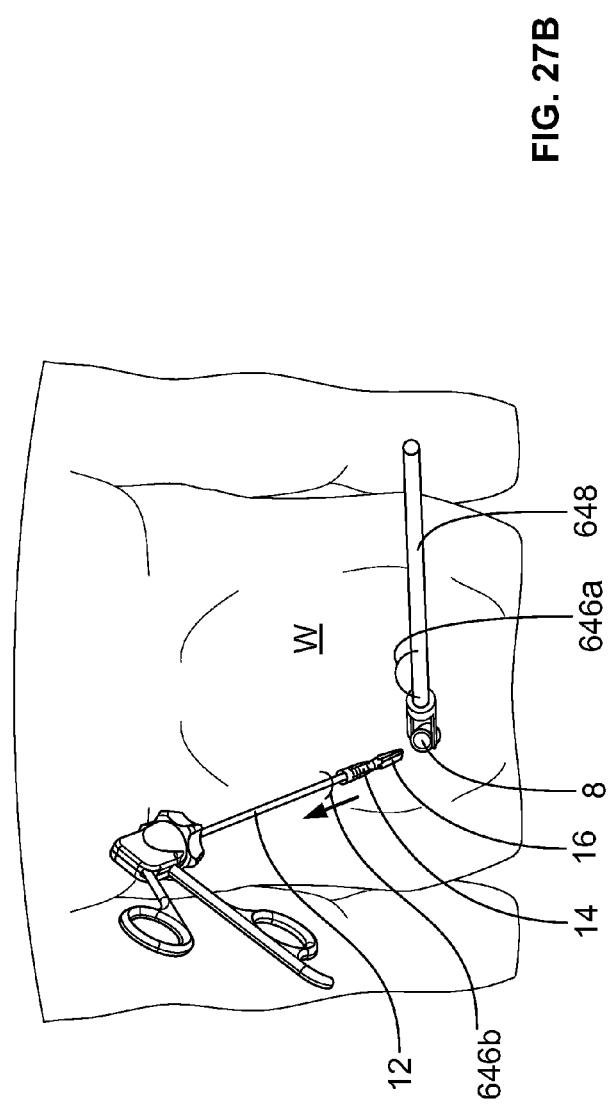

FIGS. 27a and 27b illustrates that the control shaft 12 can be translated, as shown by arrow, away from the introducer 8. The tool 16 can emerge and be removed from the introducer channel 98 along with the end effector 14.

Figure 28C:
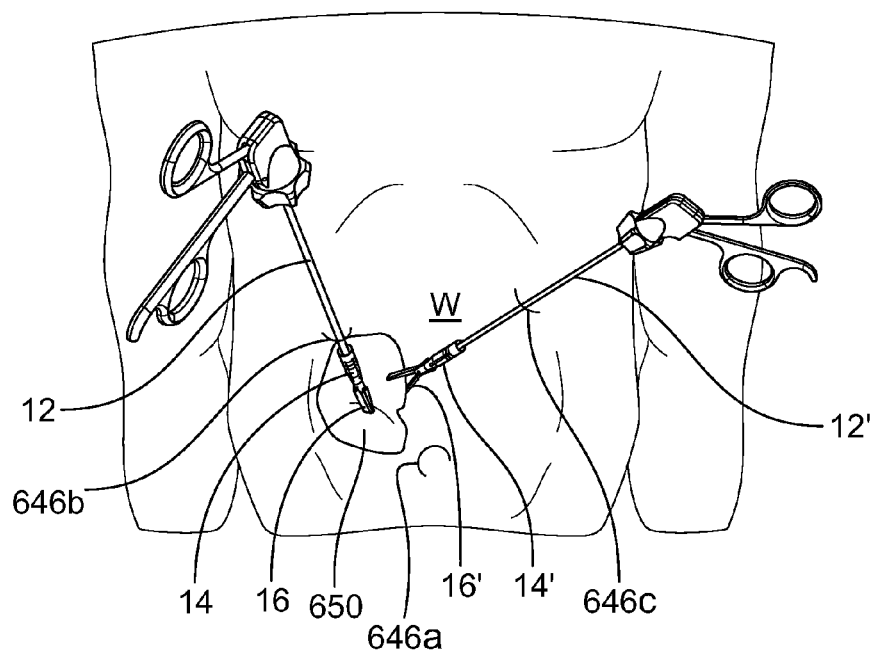
FIG. 28c demonstrates two assembled devices grasping tissue inside of a body cavity.

FIGS. 28a through 28c illustrates that the tool 16 can be opened, as shown by arrows 654, or otherwise articulated or used free of obstruction from the introducer 8. The actuator key 38 can be longitudinally interference fit within the inner sub-shaft angular notch 86. When the inner sub-shaft 18b is translated, as shown by arrow 652, with respect to the outer sub-shaft 18a, the tool can be opened or closed, as shown by arrows 654.

FIG. 28c illustrates that first and second control shafts 12 and 12' can be deployed into the abdominal cavity. The first and second control shafts 12 and 12' can be attached to first and second end effectors 14 and 14' and tools 16 and 16'. The first and second control shafts 12 and 12' can be inserted through second and third access sites 646b and 646c. The introducer 8 with the end effector 14 and the tool can be deployed through the first access site 646a, for example through the umbilicus. The tools 16 and 16' can be maneuvered and controlled in the target site by the control shafts 12 and 12'. The tools 16 and 16' can be used to concurrently or subsequently manipulate tissue or an organ 650.

The tools 16 and 16' and end effectors 14 and 14' can be removed from the abdominal cavity through the first access site 646a and the control shafts 12 and 12' can be removed through the second and third access site 646b and 646c, respectively. For example, the aforementioned method can be performed in reverse.

A retraction system within a patient's abdominal cavity can have a needle element 100 that can have a shaft of the needle 101 with a coaxial wire 102 that can be extended through the distal end of the needle shaft 101. The needle shaft 101 may be inserted into the abdominal cavity "AC" by puncturing the abdominal wall "W". The needle shaft 101 is sized small enough that it will not scar tissue when it is used to puncture that tissue, yet large enough to have sufficient size to house a coaxial wire 102 with a diameter capable of providing adequate strength to maintain the desired configurations described below. For example, an eighteen gauge needle shaft 101 has a low probability of scarring and is large enough to house a one millimeter coaxial wire 102. Those skilled in the art will recognize the needle shaft 101 gauges that will provide the adequate functionality.

The coaxial wire 102 can have two configurations. FIG. 1A depicts the wire 102 in the first configuration, when the wire 102 is straight. Wire 102 remains in this straight configuration while it remains largely enclosed by the needle shaft 101.

When the wire is extended through the distal end of the needle shaft 101, the wire can form a curved hook portion at the distal end of the wire 102. In the preferred embodiment, the end of the hook is blunt. The wire 102 may be made from a shape memory alloy or any other material rigid enough to hold the hooked shape throughout the retraction yet is pliable enough to retain a substantially straight shape when the wire 102 is not extended from the needle shaft 101. Materials that provide shape memory can be high tensile strength metallic materials and pre-formed polymeric materials.

The grasping tool 200 can have a curved anchoring portion on the proximal end 201 and a grasping mechanism 202 on the distal end. The curved end 201 may be anchored to the curved hook portion of the distal end of wire 102 when in the second configuration. In the preferred embodiment, the curved portion is non-circular. The grasping mechanism 202 may be one of several mechanisms known in the art, such as a simple hook or a grasping mechanism with two jaws actuated by a spring and detent. Those skilled in the art will recognize other grasping mechanisms. The grasping tool 200 may be inserted into the patient's abdominal cavity "AC" via a laparoscopic trocar 300.

Figure 29:
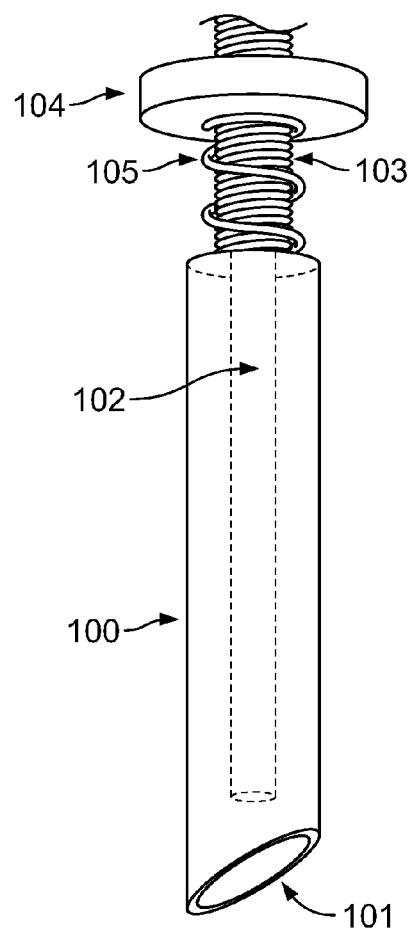
FIG. 29 illustrates a variation of the device where the trans-abdominal shaft comprises a suspension system.

The extension of the wire 102 may be adjusted as shown in FIG. 29. The proximal end of the needle element 100 is threaded 103. A thumb wheel 104 with threads that match the threads 103 can be used to adjust the extension of the coaxial wire element 102. If the grasping tool 200 needs to pull the tissue or organ towards the abdominal wall "W", the thumb wheel 104 is adjusted so that the wire 102 is extended less from the needle shaft 101. If the grasping tool 200 needs to shift the tissue or organ away from the abdominal wall "W", the thumb wheel 104 is adjusted so that the wire 102 is extended more from the needle shaft 101. The thumb wheel 104 may be spring loaded with spring 105 in order to assist the adjustment of the retraction. This allows the coaxial wire 102 to be extended a fixed amount. Once set, the surgeon's attention is no longer required in order to utilize the retraction system.

As shown in FIGS. 30 and 31, the needle element 100 inserted into the patient's abdominal cavity "AC" may be stabilized by a stabilization pad 400, in order to stabilize the needle element 100 while inserted into the patient's body. FIG. 30 shows a simple stabilization pad mounted to the patient's abdominal wall "W". The pad contains at least one hole 401 with a diameter at least as large as the outer diameter of the needle element 100. The needle element is inserted through the abdominal wall "W" through the hole 401 in the stabilization pad 400.

A variation of the stabilization pad is shown in FIG. 31. In addition to the hole 401, a cone 402 sits atop each hole 401. The cone 402 has at least one channel running the length of the cone. This channel has a diameter at least as large as the hole 401. When used with a needle element 100 with a threaded proximal end 103, the height of the cone 402 is set so that enough of the threaded end 103 is exposed to allow for sufficient adjustability of the extension of the coaxial wire 102. The cone 402 provides additional stability to the needle element 100. Those skilled in the art will recognize that shapes other than cones are capable of providing stability. A single stabilization 400 pad may have multiple holes 401 and cones 402.

To utilize the retraction system described above, the surgeons can introduce two or more trocars: for example, a first trocar for the endoscope and a second trocar to allow for the introduction of the surgical tools. The needle shaft 102 is inserted into the body cavity near the site for retraction, and the wire 102 is extended from the needle shaft 102. A grasping tool 200 is inserted into the body cavity. The curved anchoring end 201 is anchored to the wire 102 in its second configuration. The grasping mechanism 202 is used to perform the retraction by manipulating the tissue or organs. One or more stabilization pads 400 may be used to assist in the retraction. The needle elements 100 are placed into the holes 401 of the stabilization pads 400. Once the retraction system is set to the desired position, the retraction system may be left unattended.

The retraction is adjusted by manipulating the amount of the extension of the coaxial wire 102 and/or by using multiple needle elements 100 and grasping tools 200 to perform the retraction. Multiple needle sites may be placed at various points in the abdomen to provide various vectors of retraction, allowing the tissue or organs to be both pushed and pulled in order to clear the surgical path.

Figure 32:
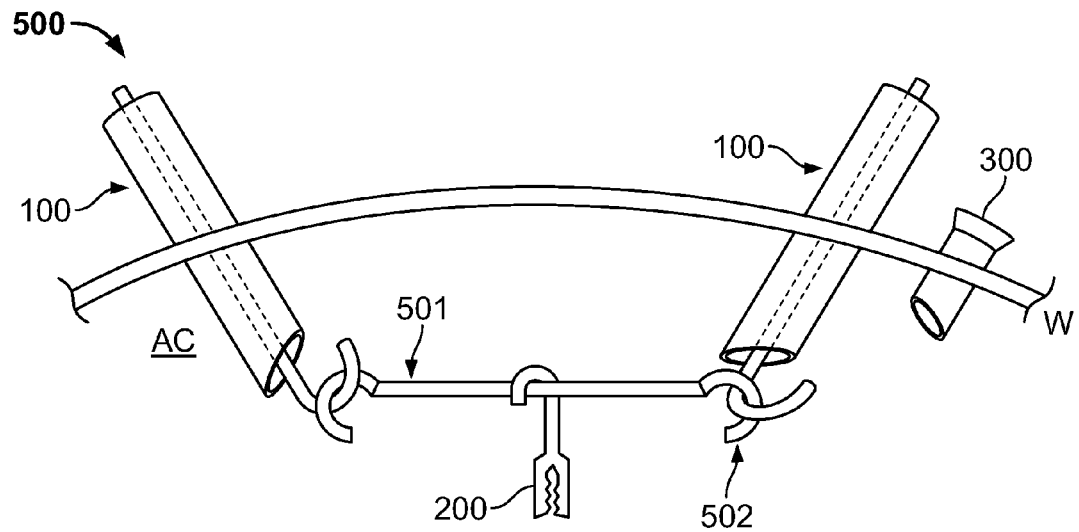

FIG. 32 is an example of the retraction system within a patient's abdominal cavity. The retraction system 500 can have at least two needle elements 100, at least one grasping tool 200, and a cable 501. The needle elements 100 and the grasping tool 200 are equivalent to the embodiments described above and are used in a similar manner. The cable 501 has curved portions 502 on each end of the cable. The cable 500 may be made of a flexible or pliable material, such as plastic or metal wire, to assist in positioning the cable. Those skilled in the art will recognize other materials that are capable of providing this functionality.

Figure 33:
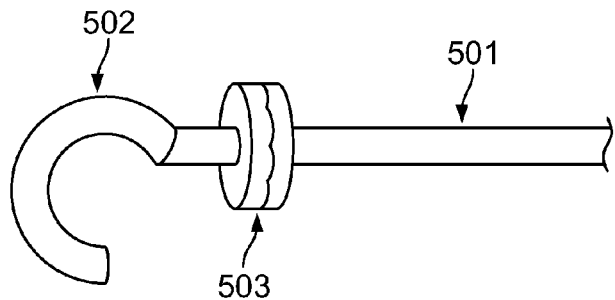
FIGS. 33 and 34 illustrate variations of the device as they are assembled across a body cavity wall.

As shown in FIG. 33, the cable 500 may include one or more flanged detents 503 that are used to adjust the length of the cable, thus allowing the surgeon to adjust the tension on the cable 500 when anchored to the needle elements 100.

To utilize the retraction system 500, the surgeons need to only introduce two trocars: one for the endoscope and a second to allow for the introduction of the surgical tools. At least two needle elements 100 are inserted into the body cavity on either side of the site for retraction, and the coaxial wires 102 are extended into the second configuration. The cable 501 is introduced into the abdominal cavity "AC" through the laparoscopic trocar 300. The curved portions 502 of the cable 501 are anchored to the curved hook portion of the coaxial wires 102 of the needle elements 100. At least one grasping tool 200 is introduced into the abdominal cavity "AC" through the trocar 300. Then the curved anchoring portion on the proximal end 201 of the grasping tool 200 is anchored to the cable 501, near the site of the retraction. The grasping mechanism 202 is used to perform the retraction by manipulating the tissue or organs. Once the retraction system 500 is set to the desired position, the system may be left unattended.

The retraction system 500 may be utilized with the same stabilization pads 400 shown in FIGS. 3 and 4. The retraction system 500 may utilize needle elements 100 as shown in FIG. 2 and needle elements 100 comprising coaxial wires 102 made from shape memory alloys.

The retraction of the tissue may be adjusted by adjusting the extension of the coaxial wires 102 as described above. This will affect the positioning of the grasping tools 200 and the retraction. One or more grasping tools 200 may be used per cable 501 to assist in the retraction. Three or more needle elements 100 may be used in the retraction system 500, with multiple cables 501 and multiple grasping tools 200 to provide various vectors for the retraction, allowing the tissue or organs to be both pushed and pulled to clear the surgical path.

Figure 34:
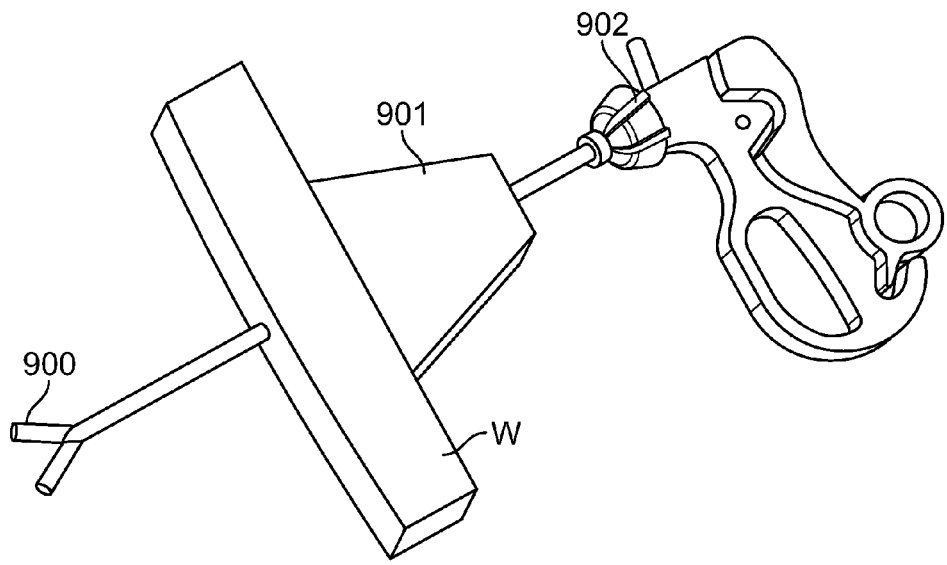

FIG. 34 is a schematic illustration of a multiple part surgical tool with the proximal handle and distal grasper connected to the trans-abdominal drive mechanism. The abdominal wall is represented by W.

The internal tool 900 is similar to standard laparoscopic grasping, cutting, dissecting, retracting and clipping devices in design and function. The tool is actuated by a central drive shaft. The internal tool 900 attaches to the distal attachment point of the trans-abdominal drive mechanism 901. The internal tool 900 is introduced into the body through the first port placed in the umbilicus. The trans-abdominal drive mechanism 901 is a combination of a needle, an attachment mechanism and a suspension system allowing for axial translation, rotational translation and angular translation around a central fulcrum located at the point of intersection with the abdominal wall W.

The trans-abdominal drive system 901 is placed at the abdominal wall. The trans-abdominal drive system 901 is comprised of central elements described in FIG. 1A and FIG. 2. Where the piercing mechanism 100 is comprised of a needle 101 and a wire 102. After the transabdominal drive system 901 is placed on the patient's skin, the abdominal wall W is pierced by needle 101. Next the wire 102 is introduced into the patient's body. The proximal end and distal end of the wire 102 are designed to couple with and lock to the internal grasper 900 and external handle 902. The external handle 902 is similar in function to standard laparoscopic tools. The distal end of the external handle 902 is designed to mate with the proximal end of the wire 102.

Figure 35:
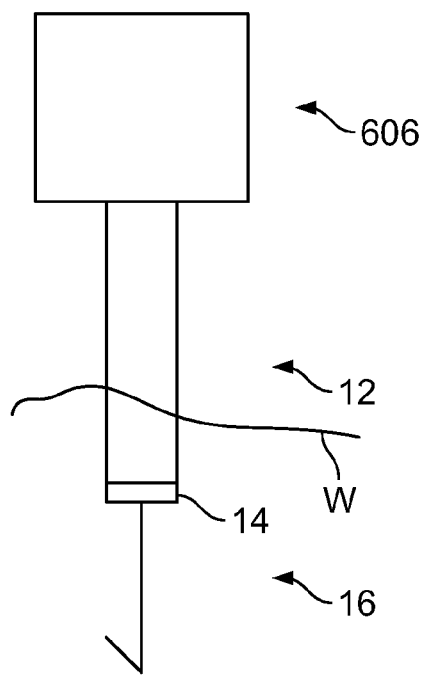
FIG. 35 is a schematic view of a variation of a method of using the device.

FIG. 35 illustrates that the trans abdominal drive system (TDS) forms a laparoscopic surgical tool. The system can have a connection member (e.g., end effector 14) for use between a proximal handle 606 and the distal tool 16. The TDS can be placed from the outside in or the inside out. The distal tool 16 may be attached to the end of an endoscope and attached to the end of the TDS.

The control shaft 12 can be placed across an abdominal wall W. A distal length of the control shaft 12, the end effector 14 and the tool 16 can be inside of the abdominal cavity. A proximal length of the control shaft 12 and the handle 606 can be outside of the abdominal cavity.

Figure 36A:
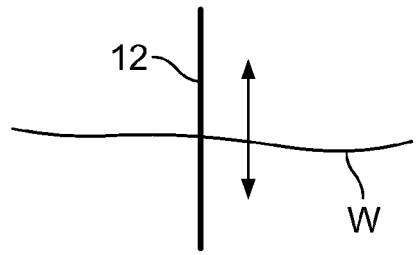
FIGS. 36a through 36c illustrate variations of manipulating the control shaft.
Figure 36B:
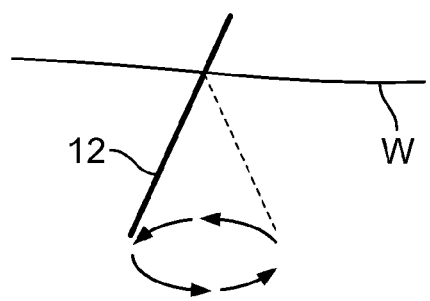
Figure 36C:
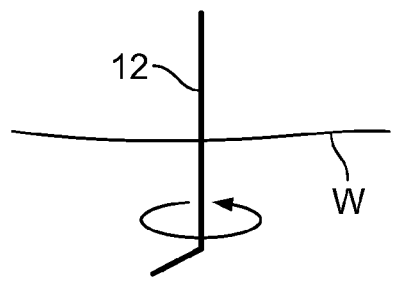

FIGS. 36a through 36c illustrate methods of manipulating the control shaft 12 inside of the abdominal cavity during use. FIG. 36a illustrates that the control shaft 12 can be oscillated partly or completely in and out, perpendicular to the abdominal wall W. FIG. 36b illustrates that the control shaft 12 can be rotated so the distal end of the control shaft 12 can create a partial or complete a circular or oval pattern. FIG. 36c illustrates that the control shaft 12 can be rotated about the longitudinal axis of the shaft 12. The control shaft 12 can be straight (as shown in FIGS. 36a and 36b) or have one or more components or features extending laterally from the shaft 12, as shown at the distal end of the control shaft 12 in FIG. 36c.

Figure 37A:
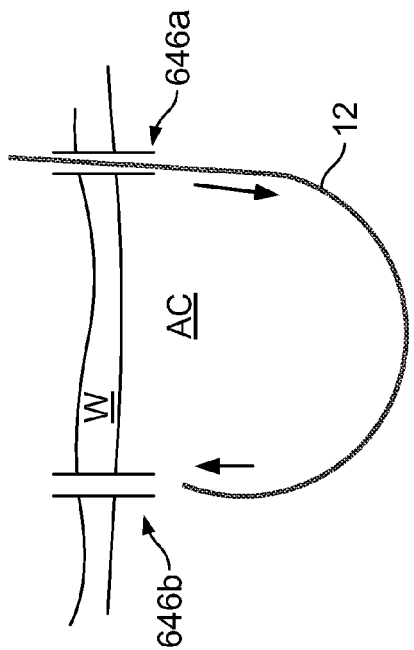
FIGS. 37a and 37b illustrate a variation of a method for deploying the control shaft 12.

FIG. 37a illustrates that the control shaft 12 can be deployed from the inside of the abdominal cavity to the outside (e.g., through the first access port of the umbilicus and then out of a second access port). The control shaft 12 may be attached to the end of an endoscope or laparoscope. The control shaft 12 can be delivered through the first access port 646a. The control shaft 12 can exit out of the second access port 646b.

Figure 37B:
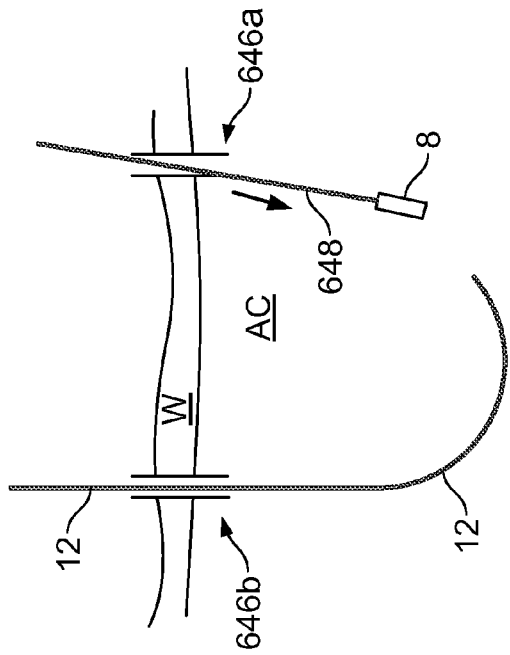

The outer handle 606 may attach to and detach from the control shaft 12. The actuate the tool 16 through a magnetic coupling and drives in the control shaft 12, for example forming all or part of the inner sub-shaft. FIG. 37b illustrates that once the control shaft 12 is deployed through the second access site 646b, the inside-out-deployed control shaft 12 can be combined with the end effector 14 and tool 16 delivered by an introducer 8, for example, through the first access site 646a.

Figure 38A:
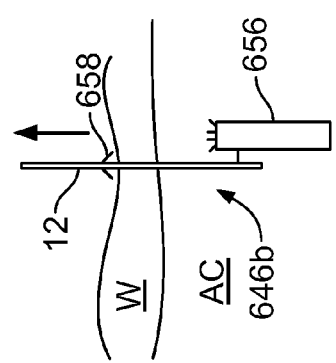
FIGS. 38a and 38b illustrate variations of deploying the control shaft through the abdominal wall.

FIG. 38a illustrates that the control shaft can be deployed from the inside of the abdominal cavity to the outside. The control shaft 12 can be bayoneted (e.g., attached on the lateral side to the other component's lateral side) or otherwise attached to an endoscope 656, for example with an integrated light source. The control shaft can have one or more harpoons 658, fish hooks, or other unidirectional piercing and fixation features or components, or combinations thereof. The harpoons 658 can pierce the abdominal wall W and prevent the length of the control shaft 12 outside of the abdominal wall from re-entering the abdominal cavity AC.

Figure 38B:
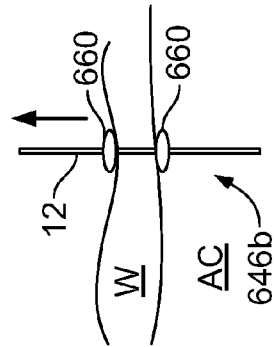

FIG. 38b illustrates that the control shaft 12 can have a magnetic coupling, for example magnets 660. The magnets 660 can be attached to the control shaft 12 on the inside and the outside of the abdominal wall W, for example, to anchor the control shaft 12 and minimize sliding of the control shaft 12 through the abdominal wall W.

FIGS. 39a through 39j illustrate that the control shaft 12 can be stabilized across the abdominal wall W with or without the use of an introducer sheath or trocar. For example, hooks, magnets, barbs, bent wires, expandable compression mechanisms and barbell shaped balloons can be employed for stabilization. Mechanical pencil drives or rack and pinion systems can be employed to drive the control shaft 12 or components of the control shaft 12 (e.g., a needle) axially and/or rotationally.

The control shaft 12, needle or other introducer can have a feature or element to stabilize the control shaft 12 across the abdominal wall W. For example, the control shaft 12, can have quills, detents on the needle, expandable feet or anchors that can contract longitudinally and extend in a radial fashion, a clamp to the side of the bed and opposing springs, bed clamp, a friction coupling (e.g., iris), porcupine quill, barbed arrows (e.g., one way phalanges), memory coils (coil occurs external and internal to abdominal wall), balloon dilation (e.g., hourglass or ratcheting), c-clamp shaped transabdominal component, internal/external hooks, internal/external magnets, ratchet (e.g., moved by thumbed wheel), chopper blades, e.g., a rubber stopper, spike brakes deployed in the subcutaneous space (or fat), or combinations thereof.

Figure 39B:
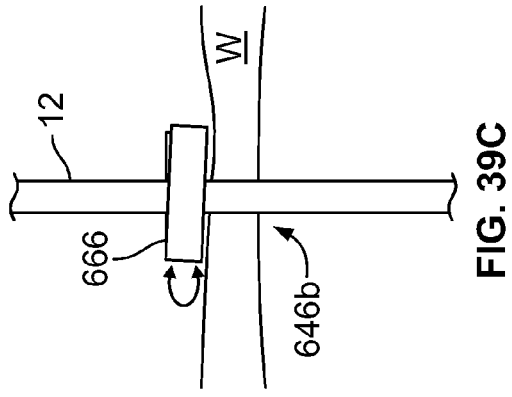
FIGS. 39a through 39j illustrate variations of the control shaft deployed through the abdominal wall.
Figure 39C:
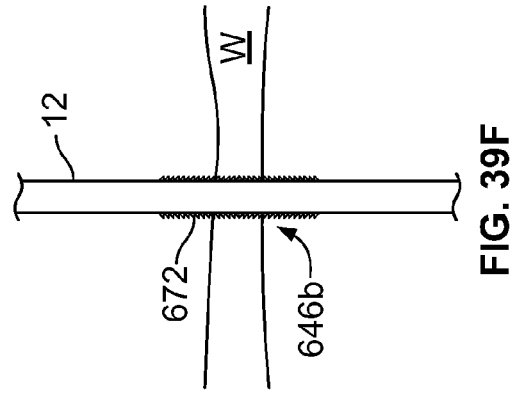
Figure 39E:
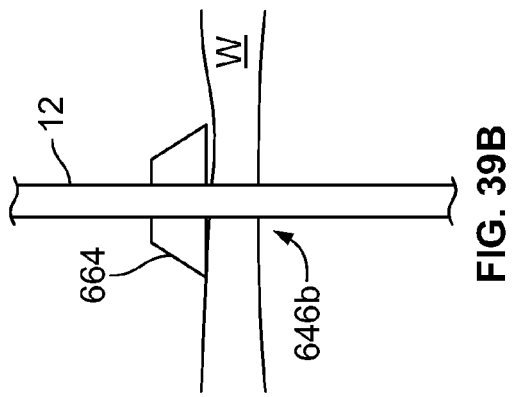
Figure 39F:
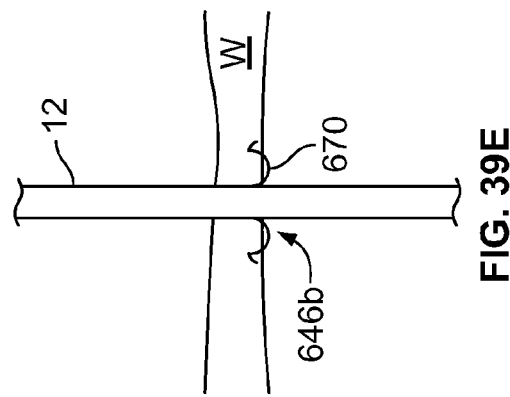
Figure 39A:
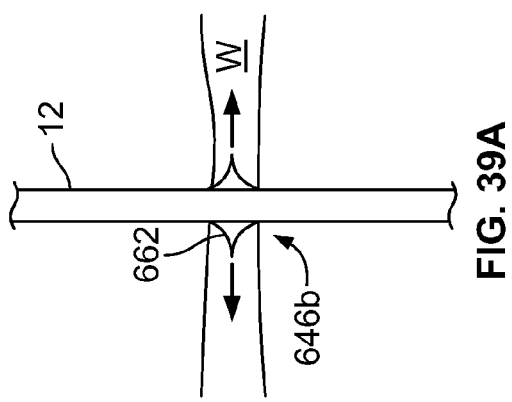
Figure 39D:
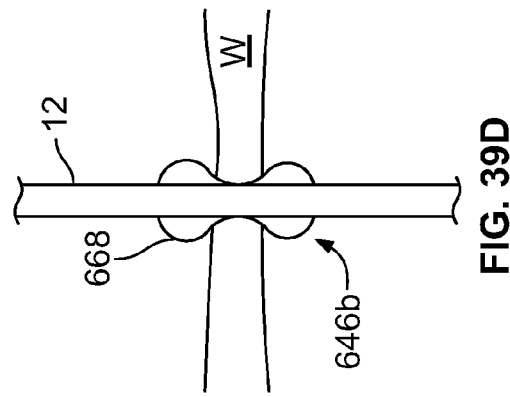

FIG. 39a illustrates that the control shaft 12 can have a radial expansion anchoring device 662 in or adjacent to the abdominal wall W. FIG. 39b illustrates that the control shaft 12 can have a stopper 664 or abutment adjacent to the abdominal wall W. FIG. 39c illustrates that the control shaft 12 can have a clip 666 that can be rotated closed on the control shaft 12 adjacent to the abdominal wall W. FIG. 39d illustrates that the control shaft 12 can have one or more hourglass-shaped inflatable bladders 668. FIG. 39e illustrates that the control shaft 12 can have fish hooks 670 that can embed into the abdominal wall W. FIG. 39f illustrates that the control shaft 12 can have opposing unidirectional high friction surface texturing 672.

Figure 39H:
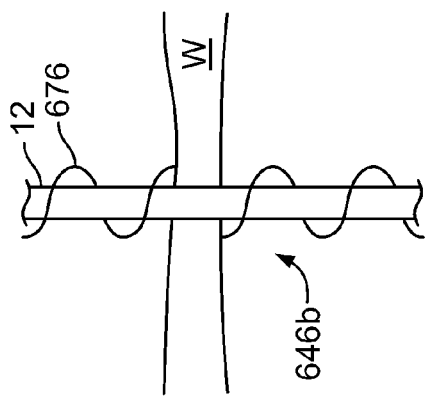
Figure 39J:
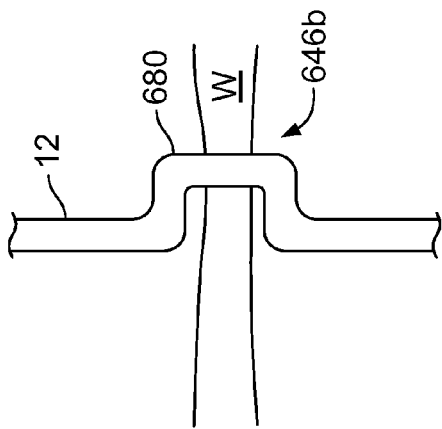
Figure 39G:
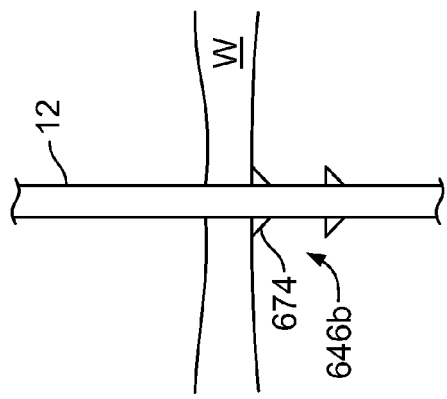

FIG. 39g illustrates that the control shaft 12 can have one, two or more unidirectional detents 674. One of the detents 674 can abut the abdominal wall W.

FIG. 39h illustrates that the control shaft 12 can have a helical screw, blade or spine 676. The helical spine 676 can extend from outer wall of the control shaft 12. The helical spine 676 can extend across the abdominal wall W.

Figure 39I:
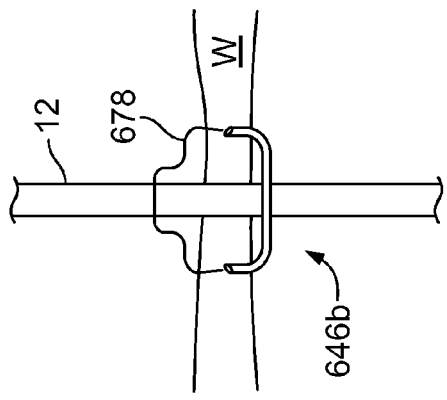

FIG. 39i illustrates that the control shaft 12 can have a male and female clamp 678 that can be assembled across the abdominal wall W. For example, the female portion of the clamp 678 can be on a first side of the abdominal wall W and the male portion of the clamp 678 can be on the second side of the abdominal wall W. The male and/or female portions of the clamp can pierce the abdominal wall and physically intersect or engage, and/or can be bound by oppositely polarized magnets in the portions of the clamp 678.

FIG. 39j illustrates that the control shaft 12 can have a bend 680 across the abdominal wall W. The bend 680 can include four symmetric right turns, which can hold the control shaft 12 fixed on the abdominal wall W.

Figure 40A:
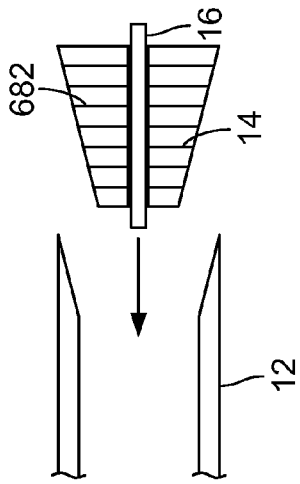
FIGS. 40a and 40b illustrate a variation of a method of attaching the tool to the control shaft.
Figure 40B:
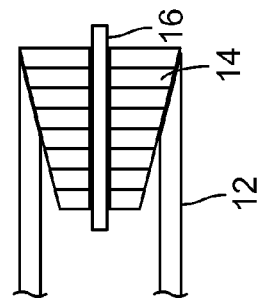

FIGS. 40a and 40b illustrate that the control shaft 12 and/or the end effector 14 can have a collet configuration. The end effector 14 can be used to attach the tool 16 to the distal end of the control shaft 12. A roller type clamp similar to the types used to clamp fluid lines in a hospital setting may be used to attach the distal end effecter to the distal end of the control shaft 12. The end effector 14 can have transverse ribs 682 and/or helical threads or screws.

Figure 41A:
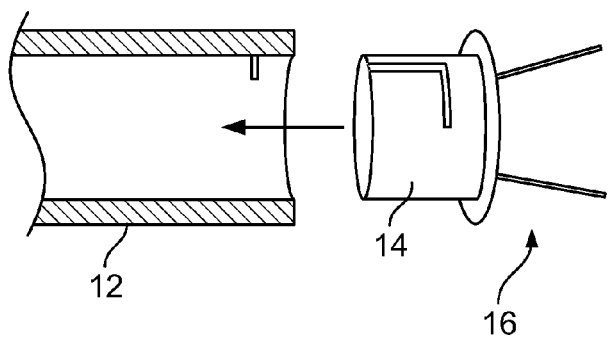
FIGS. 41a and 41c illustrate a variation of a method of attaching the tool to the control shaft.
Figure 41B:
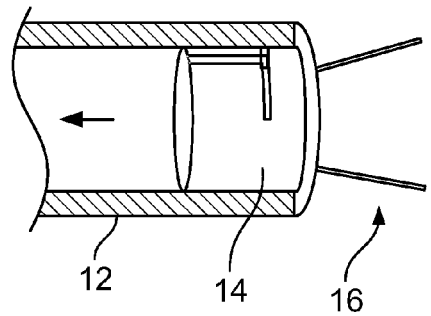
Figure 41C:
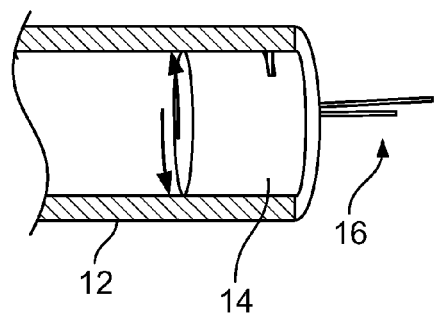
Figure 42:
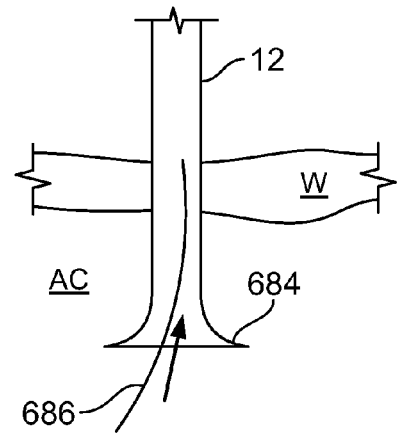
FIG. 42 illustrates a variation of a method of using a variation of the control shaft.

FIG. 41a through 41c illustrate that the end effector 14 can have a gated channel or a twist-lock similar to a pill bottle cap may be used to attach the proximal and distal elements or tools 16 to the control shaft 12. The end effector 14 can have a lock similar to the lock used on telescoping walking sticks to attach elements, such as tools 16, to the control shaft 12. End effectors 14 can have attachment elements, configurations or features that can include: hook and loop designs, detent-mating devices, tulip funnels 684 (e.g., the portion of the end effector 12 inside of the abdomen can radially expand or funnel for a transabdominal end effector, as shown in FIG. 42) which can allow for easy passage of wire 686, a toggle screw (e.g., cufflink action), screw deployment (e.g., EEA stapler), magnet fishing rod (e.g., introduced from outside) that can bring internal components out, a pill bottle cap or clicking pen lock, self-centering magnet coupled to a transabdominal perforating mechanism, a friction collet (smooth or threaded), a pinch cannula (e.g., ties, band, roller clamp, or combinations thereof), external suction through a transabdominal cannula, a ball and socket or a ball on the end of a wire, and combinations thereof.

One or more wires can pass through the control shaft 12, for example, to drive one or more actions, or deliver or receive data or power in the tools 16. Axial motion may be generated through the control shaft 12 by a telescoping linkage or a telescoping spirally wound element. The wires can extend through and/or be the inner sub-shaft 18b.

The control shaft 12 can be advanced into the target site by a spring-driven axially advancing mechanism. The control shaft 12 can be a 14 gauge needle. The control shaft 12 can be mechanically advanced or supported with one or more trans-abdominal members, hydraulic channels, suction bean bags (i.e., which can be malleable when inflated, and very stiff when deflated), rigidized wings, a collapsing scaffold (e.g., a longitudinally extendable wireframe or woven "finger trap"), tension on a wire which stiffens components on the wire, electromagnetics and combinations thereof.

One or more wires can be routed through one or more channels, lumens or holes in the control shaft 12, for example to drive the tool 16. The internal section could be supported by a telescoping mechanism. The laparoscopic tool can be thin and supported laterally by an adjacent needle. The abdominal wall tissue may be deflected up and inside the control shaft 12 to provide lateral support to the control shaft 12 or the adjacent needle.

The tool 16 can act as an EU marionette, an internal rack line to hook components to, one or more cannulas to drive flexible tools in one or more directions, internal black box where multiple wires feed into and actuate complex motions, or combinations thereof.

Hydraulic systems may be used to drive the tool 16, for example by routing the hydraulic lines through another the first access site or another access site or incision in the abdomen. The tool 16 can be powered by thin, hard polymer cables extending through the control shaft 12, one or more telescoping tools, a steerable wire, a party whistle extender, an auger shape drive shaft (e.g., turning a knob outside turns the auger blades, which drives a component inward), or combinations thereof.

Figure 43:
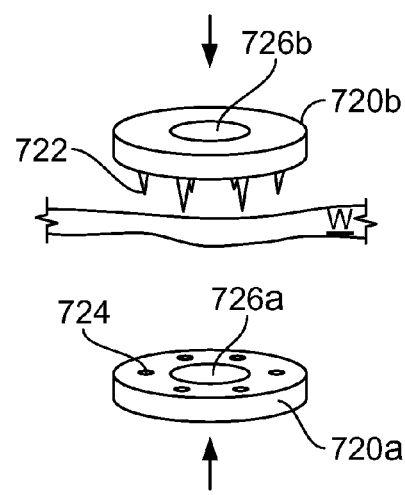
FIG. 43 illustrates a variation of a device and method for accessing the abdominal cavity.

FIG. 43 illustrates that the device can have internal and external plates 720a and 720b that can be connected to each other across the abdominal wall W by needles or anchors 722. The anchors 722 can extend from one or both plates 720 and be received by anchor ports 724 in the opposite plate 720. When the plates are attached, a port can be cut or punctured through the abdominal wall through a central port 726a and 726b through the middle of each plate 720a and 720b, respectively.

The control shaft 12 can be used transabdominally and can be 14 gauge or smaller (e.g., 1.63 mm or 0.064 in). The first access site or umbilical port can deliver a twenty five millimeter (25 mm) diameter device into the abdominal cavity. An external member, such as a handle, can actuate the motion of an internal member, such as a tool deployed into an abdominal cavity.

Figure 44:
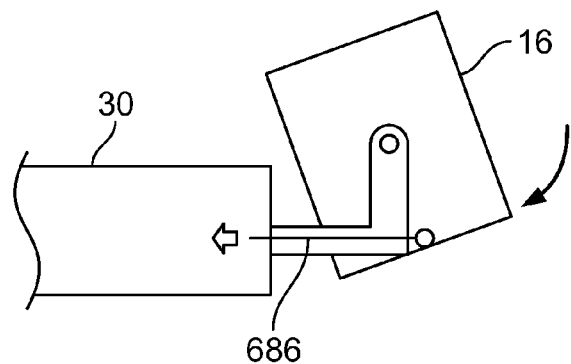
FIG. 44 illustrates a method for using the tool.

FIG. 44 illustrates a rotating grasper assembly at the distal end of the actuator shaft 30. By pulling the wire 686, as shown by arrow, the tool 16 held by the grasper can be oriented, as shown by arrow, in any direction inside the body.

Figure 45:
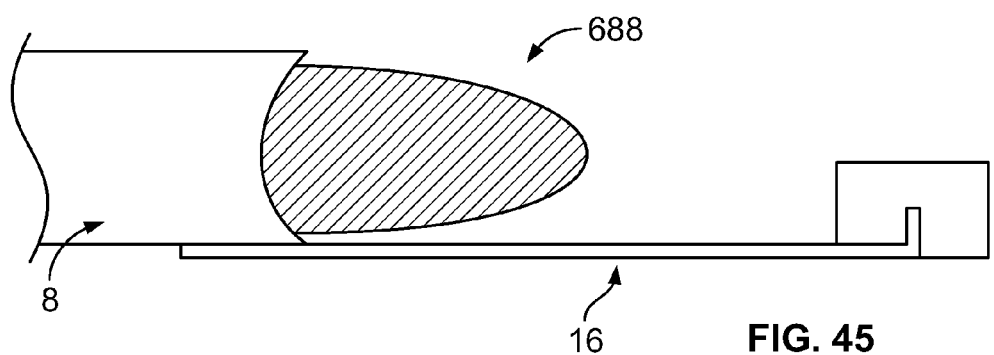
FIG. 45 illustrates a variation of the endoscopic tip.

FIG. 45 illustrates that the introducer 8 can have an endoscope, with an endoscope tip 688 emerging from the distal end of the introducer 8. The endoscope can allow the surgeon to see and introduce the distal tool 16 with a single instrument.

Figure 46:
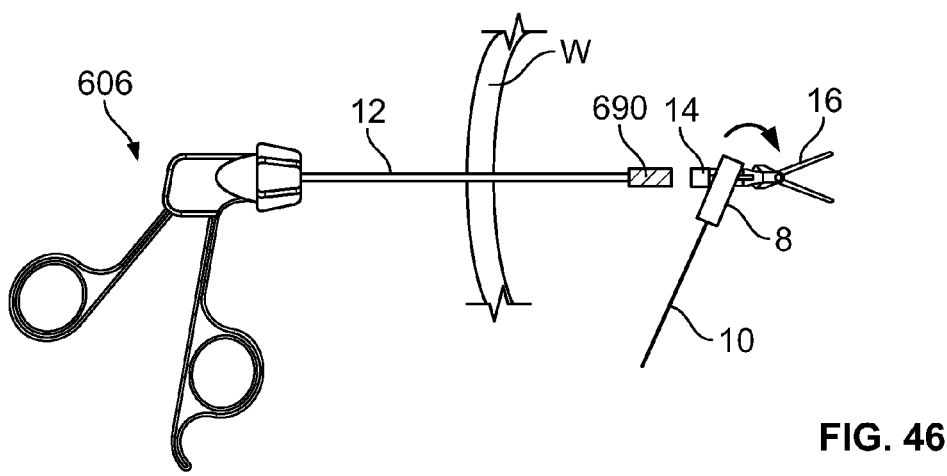
FIG. 46 illustrates a method for using a variation of the delivery system or introducer rod.

FIG. 46 illustrates that the end effector 14 can be rotatably attached to the introducer 8 and/or the introducer rod 10. The distal end of the control shaft 12 can have a threaded attachment 690. The end effector 14 can releasably engage with the threaded attachment 690. The control shaft 14 or needle shaft and the end effector 14 can be threaded in order to attach both pieces to each other.

In another variation or in addition to an otherwise disclosed variation, the end effector 14 can have a magnetic component, such as a permanent magnet. The tool 16 can have a magnet that is opposite polarized to the magnet in the end effector 14 or be made from a ferromagnetic material. The magnetic tool can attach to the magnetic end effector 14.

Figure 47:
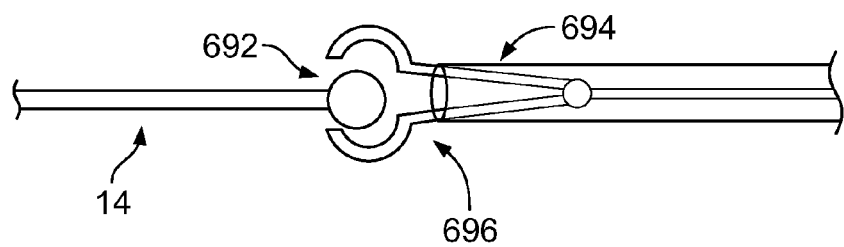
FIG. 47 illustrates a variation of the end effector attachment mechanism.

FIG. 47 illustrates the proximal end of the end effector 14 can have a ball end attachment 692. The distal end of the control shaft 12 can have a collet grasp 696. The control shaft 12 can have a hollow sleeve 694. The collet grasp 696 can be retracted into or extended out of the hollow sleeve 694. Linear motion of either the control shaft 12 or the end effector 14 can move the other element.

Figure 48:
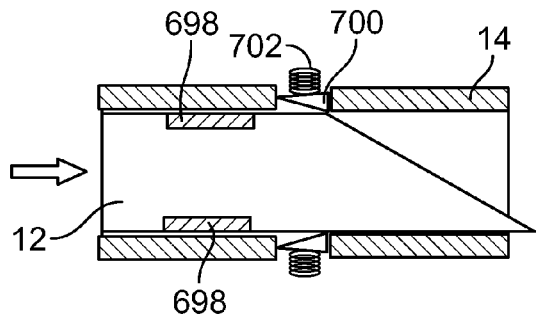
FIG. 48 through 52 illustrate variations of the end effector and the control shaft.

FIG. 48 illustrates that the distal end of the control shaft 12 can have control shaft recessions, grooves, divots or slots 698. The proximal end of the end effector 14 can have clasps 700 adjacent to compressed springs 702. When the control shaft 12 is inserted, as shown by arrow, far enough into the end effector 14, the springs 702 can push the clasps 700 into the slots 698, locking the control shaft 12 to the end effector 14. A very strong connection can be made once the clasps 700 lock into the slots 698.

Figure 49:
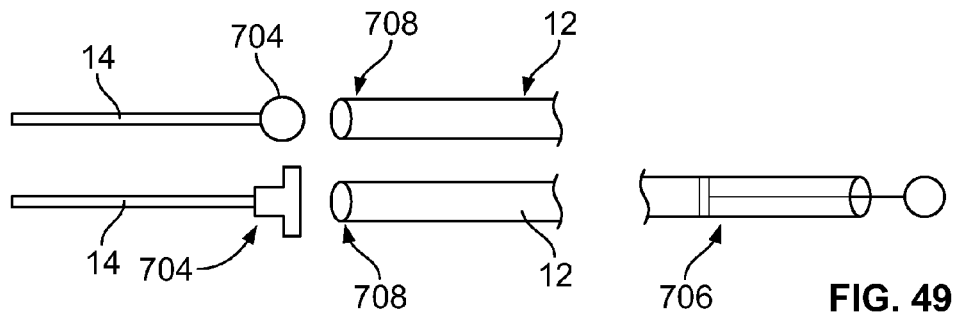

FIG. 49 illustrates variations of vacuum attachment configurations between the end effector 14 and the control shaft 12. The control shaft 12 can be a hollow tube that can carry a vacuum created by a pump or a syringe. 706. The proximal end of the end effector 14 can be configured as a plug 704. The distal vacuum end 708 of the control shaft 12 can be a soft seal or a hard end. The plug 704 can form a vacuum attachment with the distal vacuum end 708.

Figure 50:
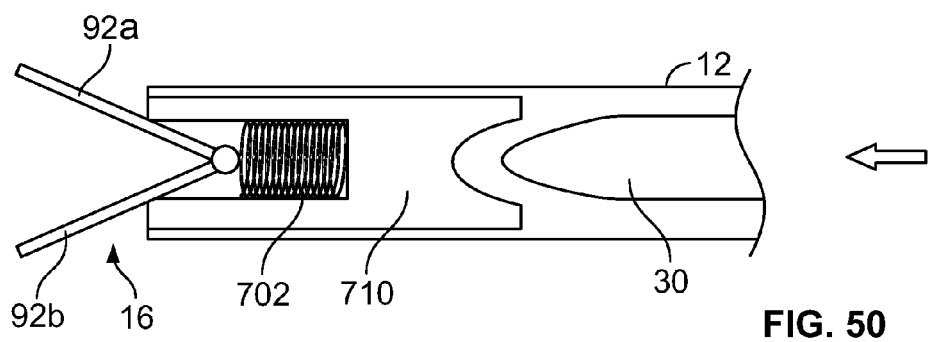

FIG. 50 illustrates that the tool 16 can be actuated by actuator shaft 30 or the inner sub-shaft 18b within the control shaft 18. The actuator shaft 30 can move distally, as shown by arrow, acting as a push rod actuator. The direct linear motion of the actuator shaft 30 can press the tool base 710 to closes the graspers or jaws 92, which can decrease frictional losses. The tool 16 can have a spring 702 to maintain the jaws in an opened (or closed) configuration when the jaws 92 are not activated.

Figure 51:
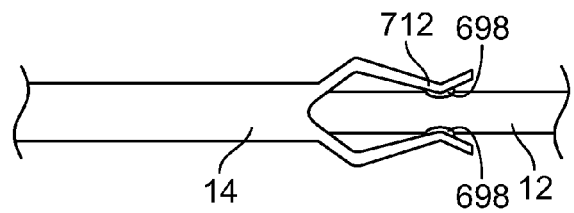

FIG. 51 illustrates that the control shaft 12 can have one or more slits or slots 698 that can each be configured to receive a spring clasp lock. 712. Each spring clasp lock 712 can resiliently deflect into the slots 698. When the spring clasp locks 712 align with the slots 698, the clasp locks 712 can engage and fix to the slots 698.

As the control shaft 12 enters the end effector channel on the end effector 14, the clasp locks 712 can deflect outwards until the clasp locks 712 lock into corresponding slots 698 in the control shaft 12 housing.

The control shaft 12 can have multiple layers. The body of the control shaft 12 can have a sleeve which can disengage the clasp locks 712, as well as an internal sub-shaft or push rod actuator.

Figure 52:
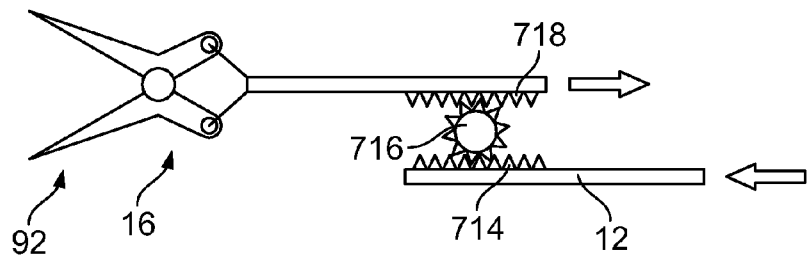

FIG. 52 illustrates that the device can have a rack and pinion actuated tool 16. The distal end of the control shaft 12 can have or be connected to a push rack 714. The push rack 714 can be geared to a pinion gear 716. The pinion gear 716 can be geared to a pull rack 718. The pull rack 718 can be directly attached to the tool 16.

Linear translation of the push rod or control shaft 12 can activate the push rack 714, causing the pinion gear 716 to rotate and activate the pull rack 718. This creates a pulling motion that can open or close the graspers or jaws 92. The system can have a spring that can return the mechanism to an open state automatically. Linear motion of the rack 714 and 718 can cause rotation of the pinion 716 attached to the graspers. A wire can be used to pull the spring-hinged jaws 92 closed.

During use, the abdomen can be inflated with carbon dioxide to allow the surgeon more room to work with and maneuver laparoscopic tools. The control shaft 12 can be 14 gauge. The control shaft 12 can penetrate the skin of the abdomen, for example, leaving no scar (e.g., 14 gauge needles are considered to not leave a scar).

A rotating grasper or introducer rod with a rotating connection to the introducer can be used to handle, maneuver and deliver the tool into the abdominal cavity. The surgeon can use a drawstring to tighten or loosen the grasper, as well as an actuating mechanism to rotate the grasper.

The introducer rod and the tool can be inserted through a first access site at the umbilicus. The surgeon can use an endoscope to locate the end of the control shaft 12 within the abdomen and attach the tool to the control shaft.

The control shaft 12 can have two slits configured to allow a tool to attach to the distal end of the control shaft 12. The tool can have spring-like locks that can insert into the two slits of the control shaft 14. The tool can be attached to the control shaft in the abdominal cavity.

Once the tool is attached to the control shaft, the surgeon can use the control shaft 12 and the tool 16 as a laparoscopic tool. The control shaft can have an actuating rod (e.g., the inner sub-shaft) that can actuate the tool 16. For example, the actuating rod can slide a rack-and-pinion mechanism to open and close a grasper tool. The grasper tool can be spring-loaded so the inner sub-shaft can close the grasper when actuated.

Once the surgeon is finished with the tool, the surgeon can activate a sleeve within a needle (for example, in FIG. 51) that can release the spring locks from the slits on the control shaft 12. A rotation grasper can then remove the tool through the first access site.

Any or all elements of the device and/or other devices or apparatuses described herein can be made from, for example, a single or multiple stainless steel alloys, nickel titanium alloys (e.g., Nitinol), cobalt-chrome alloys (e.g., ELGILOY® from Elgin Specialty Metals, Elgin, Ill.; CONICHROME® from Carpenter Metals Corp., Wyomissing, Pa.), nickel cobalt alloys (e.g., MP35N® from Magellan Industrial Trading Company, Inc., Westport, Conn.), molybdenum alloys (e.g., molybdenum TZM alloy, for example as disclosed in International Pub. No. WO 03/082363 A2, published 9 Oct. 2003, which is herein incorporated by reference in its entirety), tungsten-rhenium alloys, for example, as disclosed in International Pub. No. WO 03/082363, polymers such as polyethylene teraphathalate (PET), polyester (e.g., DACRON® from E. I. Du Pont de Nemours and Company, Wilmington, Del.), poly ester amide (PEA), polypropylene, aromatic polyesters, such as liquid crystal polymers (e.g., Vectran, from Kuraray Co., Ltd., Tokyo, Japan), ultra high molecular weight polyethylene (i.e., extended chain, high-modulus or high performance polyethylene) fiber and/or yarn (e.g., SPECTRA® Fiber and SPECTRA® Guard, from Honeywell International, Inc., Morris Township, N.J., or DYNEEMA® from Royal DSM N.V., Heerlen, the Netherlands), polytetrafluoroethylene (PTFE), expanded PTFE (ePTFE), polyether ketone (PEK), polyether ether ketone (PEEK), poly ether ketone ketone (PEKK) (also poly aryl ether ketone ketone), nylon, polyether-block co-polyamide polymers (e.g., PEBAX® from ATOFINA, Paris, France), aliphatic polyether polyurethanes (e.g., TECOFLEX® from Thermedics Polymer Products, Wilmington, Mass.), polyvinyl chloride (PVC), polyurethane, thermoplastic, fluorinated ethylene propylene (FEP), absorbable or resorbable polymers such as polyglycolic acid (PGA), poly-L-glycolic acid (PLGA), polylactic acid (PLA), poly-L-lactic acid (PLLA), polycaprolactone (PCL), polyethyl acrylate (PEA), polydioxanone (PDS), and pseudo-polyamino tyrosine-based acids, extruded collagen, silicone, zinc, echogenic, radioactive, radiopaque materials, a biomaterial (e.g., cadaver tissue, collagen, allograft, autograft, xenograft, bone cement, morselized bone, osteogenic powder, beads of bone) any of the other materials listed herein or combinations thereof. Examples of radiopaque materials are barium sulfate, zinc oxide, titanium, stainless steel, nickel-titanium alloys, tantalum and gold.

While the retraction systems, in accordance with the present disclosure, have been described as being used in connection with surgical procedures performed within the abdominal cavity, it is envisioned that the retraction systems disclosed may be used in other surgical procedures. It is understood that various modifications may be made to the embodiments of the presently disclosed retraction system. Therefore, the above description should not be construed as limiting, but merely illustrative of the variations described herein.

We claim:

1. A method for surgery in a body comprising:
   attaching a tool to a distal end of an introducer outside of the body, wherein the tool has a tool longitudinal axis; inserting a distal end of a control element into the body through a second access site; inserting the introducer distal end into the body through a first access site until the tool is disposed adjacent the control element distal end; and
   rotating a shaft element of the control element, thereby rotating one or more elements on the tool in a second direction relative to a non-rotating portion of the tool to simultaneously both lock the tool inside of the body to the control element distal end and unlock the tool from the introducer distal end.

2. The method of claim 1, wherein attaching a tool to a distal end of an introducer comprises rotating one or more of the one or more elements in a first direction opposite the second direction relative to the non-rotating portion outside of the body to lock the introducer distal end to the tool.

3. The method of claim 1, wherein the second access site is smaller than the first access site.

4. The method of claim 1, further comprising;
   performing a treatment with the tool at a target site in the body;
   reattaching the tool to the introducer distal end; and
   removing the introducer distal end and tool through the first access site.

5. The method of claim 4, further comprising removing the control element through the second access site.

6. The method of claim 4, wherein reattaching the introducer to the tool comprises rotating a shaft element of the control element, thereby rotating one or more of the one or more elements on the tool to lock the tool to the introducer distal end and unlock the tool from the control element.

7. The method of claim 1, wherein inserting the introducer distal end through the first access site comprises inserting the introducer distal end and the tool through the first access site.

8. The method of claim 1, wherein the introducer is separate from the tool after the tool is attached to the control element.

9. The method of claim 1, wherein inserting the introducer distal end into the body through the first access site comprises inserting an effector through the first access site.

10. The method of claim 1, further comprising sliding the introducer distal end off the tool after rotating the shaft element to lock the tool inside of the body to the control element and unlock the tool from the introducer distal end.

11. The method of claim 1, further comprising:
performing a procedure inside the body with the tool;
positioning the distal end of the introducer adjacent the tool; and
rotating the shaft element in a second direction opposite the first direction to simultaneously unlock the tool from the control element distal end and lock the tool to the introducer distal end.

12. A device for surgery comprising:
an introducer;
a working tool;
an effector comprising a rotating-locking element comprising a first connector and a second connector rotatably mounted relative to a non-rotating portion of the effector, and wherein the effector is attached to the working tool; and
a control element;
wherein the rotating-locking element is rotatable between a first position wherein the first connector locks the effector to the introducer, and a second position, wherein rotation of the rotating-locking element to the second position simultaneously both causes the second connector to lock the effector to the control element and causes the first connector to unlock the effector from the introducer.

13. The device of claim 12, wherein the introducer is separate from the tool after the tool is attached to the control element.

14. The device of claim 12, wherein the control element comprises a shaft.

15. The device of claim 12, wherein the working tool comprises a grasper.

16. The device of claim 12, wherein the control element has a smaller diameter than a diameter of the effector.

17. The device of claim 12, wherein the control element comprises a first shaft and a second shaft coaxial with the first shaft.

18. The device of claim 17, wherein the first shaft is configured to activate the working tool when the first shaft slides with respect to the second shaft.

19. The device of claim 12, wherein, in the second position, the effector is rotationally fixed to the control element.

20. A device for surgery comprising:
an introducer rod or delivery system comprising an introducer distal end for introduction into a target site;
an end effector including a working tool, and a rotating-locking element comprising a first connector and a second connector, and wherein the end effector is attached to the working tool; and
a control element comprising a control shaft including a distal end for introduction into the target site;
wherein the rotating-locking element is rotatable in a first direction relative to the end effector such that the first connector locks the end effector to the introducer distal end outside of a target site such that the introducer can deliver the end effector into the target site, and wherein the rotating-locking element is rotatable in a second direction to simultaneously both cause the second connector to lock the end effector to the distal end of the control shaft of the control element in the target site and cause the first connector to unlock the end effector from the introducer distal end.

21. The device of claim 20, wherein the introducer is separable from the end effector after the end effector is attached to the control shaft of the control element.

22. The device of claim 20, wherein the working tool comprises a grasper.

23. The device of claim 20, wherein the control shaft of the control element has a smaller diameter than a diameter of the end effector.

24. The device of claim 20, wherein the control shaft of the control element comprises a first shaft and a second shaft coaxial with the first shaft.

25. The device of claim 24, wherein the first shaft is configured to activate the working tool when the first shaft slides with respect to the second shaft once the end effector is locked to the control shaft distal end.

26. The device of claim 24, wherein the first connector comprises receiving slots on a housing of the end effector that may be aligned with locking ring slots on the rotating-locking element to allow the introducer distal end to be releasably attached to the end effector, the rotating-locking element being rotatable to misalign the locking ring slots from the receiving slots to lock the introducer distal end to the end effector.

27. The device of claim 26, wherein the control shaft is configured to be slidably inserted into the end effector channel when the end effector is attached to the introducer distal end, and wherein the control shaft is rotatable with respect to the introducer to cause the rotating-locking element to rotate in the second direction to simultaneously both unlock the end effector from the introducer distal end and lock the end effector to the control shaft.

28. The device of claim 27, wherein the end effector comprises an actuator shaft coupled to the working tool such that, when the control shaft is rotated to attach the end effector to the control shaft distal end, an actuator key on the actuator shaft of the end effector engages an inner shaft longitudinal notch on the control shaft such that the actuator shaft is longitudinally fixed to the first shaft and the first shaft can be longitudinally translated with respect to the second shaft to activate the working tool.

29. The device of claim 27, wherein the second connector comprises a locking ring key that is rotated into an outer shaft angular notch when the control shaft is rotated to attach the end effector the control shaft distal end such that the end effector is locked to the control shaft.

30. The device of claim 29, wherein the locking ring key is configured to rotate within an axle slot within the housing, limiting rotation of the rotating-locking element with respect to the housing.

* * * * *